(12) United States Patent
Dunphy et al.

(10) Patent No.: US 7,098,007 B2
(45) Date of Patent: Aug. 29, 2006

(54) CLONING AND FUNCTIONAL ASSAYS OF XENOPUS ATR

(75) Inventors: William Dunphy, Altadena, CA (US); Akiko Kymagai, Altadena, CA (US); Zijian Guo, San Diego, CA (US)

(73) Assignee: California Institute of Technology, Pasadena, CA (US)

( * ) Notice: Subject to any disclaimer, the term of this patent is extended or adjusted under 35 U.S.C. 154(b) by 266 days.

(21) Appl. No.: 10/227,610

(22) Filed: Aug. 22, 2002

(65) Prior Publication Data

US 2003/0108916 A1 Jun. 12, 2003

Related U.S. Application Data

(60) Provisional application No. 60/314,215, filed on Aug. 22, 2001.

(51) Int. Cl.
| | | |
|---|---|---|
| *C12P 21/00* | (2006.01) | |
| *C12N 15/63* | (2006.01) | |
| *C12N 15/85* | (2006.01) | |
| *C07H 15/11* | (2006.01) | |

(52) U.S. Cl. .................. 435/70.1; 435/320.1; 435/325; 536/23.1

(58) Field of Classification Search ............... 536/23.1; 435/320.1, 325, 70.1
See application file for complete search history.

(56) References Cited

U.S. PATENT DOCUMENTS 6,307,015 B1  10/2001  Elledge et al.

FOREIGN PATENT DOCUMENTS

| WO | WO 97/09433 | 3/1997 |
| WO | WO 02/33115 | 4/2001 |
| WO | WO 01/83703 | 11/2001 |

OTHER PUBLICATIONS

Hekmat-Nejad et al (Current Biology, Nov. 2000, vol. 10, p. 1565-1573).*
Gene bank accession No. AF223644. Nov. 28, 2000.*
Gene bank accession No. AF320125 Dec. 13, 2000.*
Gene bank accession No. HSU76308 Jan. 9, 1997.*
Banin, S. et al. Enhanced Phosphorylation of p53 by ATM in Response to DNA Damage. Science 281, 1674-1677 (1998).
Bentley, N.J. et al. The *Schizosaccharomyces pombe* rad3 checkpoint gene. EMBO J. 15, 6641-6651 (1996).
Blasina, A. et al. Caffeine inhibits the checkpoint kinase ATM. Current Biol. 9, 1135-1138 (1999).
Brown, A.L. et al. A human Cds1-related kinase that functions downstream of ATM protein in the cellular response to DNA damage. PNAS 96, 3745-3750 (Mar. 1999).
Brown, E.J. and Baltimore, D. ATR disruption leads to chromosomal fragmentation and early embryonic lethality. Genes Dev. 14, 397-402 (2000).
Canman, C.E. et al. Activation of the ATM Kinase by Ionizing Radiation and Phosphorylation of p53. Science 281, 1677-1679 (1998).
Canman, C.E. Replication checkpoint: Preventing mitotic catastrophe. Curr. Biol. 11, R121-R124 (2001).
Chan, T.A. et al. 14-3-3σ is required to prevent mitotic catastrophe after DNA damage. Nature 401, 616-620 (1999).
Chaturvedi, P. et al. Mammalian Chk2 is a downstream effector of the ATM-dependent DNA damage checkpoint pathway. Oncogene 18, 4047-4054 (1999).
Cimprich, K.A. et al. cDNA cloning and gene mapping of a candidate human cell cycle checkpoint protein. PNAS 93, 2850-2855 (Apr. 1996).
Cliby, W.A. et al. Overexpression of a kinase-inactive ATR protein causes sensitivity to DNA-damaging agents and defects in cell cycle checkpoints. EMBO J. 17, 159-169 (1998).
Cortez, D. et al. Requirement of ATM-Dependent Phosphoylation of Brca1 in the DNA Damage Response to Double-Strand Breaks. Science 286, 1162-1166 (1999).
de Klein, A. et al. Targeted disruption of the cell-cycle checkpoint gene ATR leads to early embryonic lethality in mice. Curr. Biol. 10, 479-482 (2000).
Durocher, D. and Jackson, S.P. DNA-PK, ATM and ATR as sensors of DNA damage: variations on a theme? Curr. Opin. Cell Biol. 13, 225-231 (2001).
Elledge, S.J. Cell Cycle Checkpoints: Preventing an Identity Crisis. Science 274, 1664-1672 (1996).
Gatei, M. et al. ATM-dependent phosphorylation of nibrin in response to radiation exposure. Nat. Genetics 25, 115-119 (May 2000).
Guo, Z. et al. Requirement for Atr in phosphorylation of Chk1 and cell cycle regulation in response to DNA replication blocks and UV-damaged DNA in Xenopus egg extracts. Genes Dev. 14, 2745-2756 (2000).
Guo, Z. and Dunphy, W.G. Response of Xenopus Cds1 in Cell-free Extracts to DNA Templates with Double-stranded Ends. Mol. Cell. Biol. 11, 1535-1546 (May 2000).
Hall-Jackson, C.A. et al. ATR is a caffeine-sensitive, DNA-activated protein kinase with a substrate specificity distinct from DNA-PK. Oncogene 18, 6707-6713 (1999).

(Continued)

*Primary Examiner*—Celine Qian
(74) *Attorney, Agent, or Firm*—Fish & Neave IP Group; Ropes & Gray LLP

(57) ABSTRACT

The present invention provides compositions of ATR nucleic acids and proteins, as well as methods of using said compositions in screening assays. The invention further provides antibodies and transgenic animals based on the ATR compositions.

11 Claims, 11 Drawing Sheets

OTHER PUBLICATIONS

Hirao, A. et al. DNA D amage-Induced Activation of p53 by the Checkpoint Kinase Chk2. Science 287, 1824-1827 (2000).

Hoekstra, M.F. Responses to DNA damage and regulation of cell cycle checkpoints by the ATM protein kinase family. Curr. Opin. Genetics and Development 7, 170-175 (1997).

Keegan, K.S. et al. The Atr and Atm protein kinases associate with different sites along meiotically pairing chromosomes. Genes & Development 10, 2423-2437 (1996).

Kim, S.-T. et al. Substrate Specificities and Identification of Putative Substrates of ATM Kinase Family Members. J. Biol. Chem. 274, 37538-37543 (Dec. 31, 1999).

Kumagai, A. et al. The Xenopus Chk1 Protein Kinase Mediates a Caffeine-sensitive Pathway of Checkpoint Control in Cell-free Extracts. J. Cell. Biol. 142, 1559-1569 (Sep. 21, 1998).

Lavin, M.F. and Shiloh, Y. The Genetic Defect in Ataxia-Telangiectasia. Annu. Rev. Immunol. 15, 177-202 (1997).

Liu, Q. et al. Chk1 is an essential kinase that is regulated by Atr and required for the G2/M DNA damage checkpoint. Genes & Development 14, 1448-1459 (2000).

Matsuoka, S. et al. Linkage of ATM to Cell Cycle Regulation by the Chk2 Protein Kinase. Science 282, 1893-1897 (1998).

O'Connell, M.J. et al. The G2-phase DNA-damage checkpoint. Trends Cell Biol. 10, 296-303 (Jul. 2000).

Sanchez, Y. et al. Regulation of RAD53 by the ATM-Like Kinases MEC1 and TEL1 in Yeast Cell Cycle Checkpoint Pathways. Science 271, 357-360 (1996).

Sarkaria, J.N. et al. Inhibition of ATM and ATR Kinase Activities by the Radiosensitizing Agent, Caffeine, Cancer Res. 59, 4375-4382 (Sep. 1, 1999).

Scully, R. et al. DNA polymerase stalling, sister chromatid recombination and the BRCA genes. Oncogene 19, 6176-6183 (2000).

Shiloh, Y. ATM and ATR: networking cellular responses to DNA damage. Curr. Opin. Genetics and Development 11, 71-77 (2001).

Smith, G.C.M. and Jackson, S.P. The DNA-dependent protein kinase. Genes & Development 13, 916-934 (1999).

Smith, G.C.M. et al. Purification and DNA binding properties of the ataxia-telangiectasia gene product ATM. PNAS 96, 11134-11139 (Sep. 1999).

Suzuki, K. et al. Recruitment of ATM Protein to Double Strand DNA Irradiated with Ionizing Radiation. J. Biol. Chem. 274, 25571-25575 (1999).

Takai, H. et al. Aberrant cell cycle checkpoint function and early embryonic death in Chk1 mice. Genes & Development 14, 1439-1447 (2000).

Tominaga, K. et al. Role of Human Cds1 (Chk2) Kinase in DNA Damage Checkpoint and its Regulation by p53. J. Biol. Chem. 274, 31463-31467 (Oct. 29, 1999).

Walworth, N.C. Cell-cycle checkpoint kinases: checking in on the cell cycle. Curr. Opin. Cell Biol. 12, 697-704 (2000).

Zhou, B.-B.S. and Elledge, S.J. The DNA damage response: putting checkpoints in perspective. Nature 408, 433-439 (Nov. 23, 2000).

* cited by examiner

Fig. 1

SEQUENCE LISTING

```
<160> NUMBER OF SEQ ID NOS: 5

<210> SEQ ID NO 1
<211> LENGTH: 7965
<212> TYPE: DNA
<213> ORGANISM: Xenopus laevis
<220> FEATURE:
<221> NAME/KEY: CDS
<222> LOCATION: (1)..(7965)
<223> OTHER INFORMATION:

<400> SEQUENCE: 1 atg gct act gac ccc ggt ctt gaa atg gcc tct atg atc ccg gcc ttg      48
Met Ala Thr Asp Pro Gly Leu Glu Met Ala Ser Met Ile Pro Ala Leu
1               5                   10                  15 cgt gaa ctt gcc agt gcc ggg gca gag gaa tat aac aca act gtt cag      96
Arg Glu Leu Ala Ser Ala Gly Ala Glu Glu Tyr Asn Thr Thr Val Gln
            20                  25                  30 aaa cca aga caa atc ctt tgc cag ttt ata gac cgg att ctg aca gat     144
Lys Pro Arg Gln Ile Leu Cys Gln Phe Ile Asp Arg Ile Leu Thr Asp
        35                  40                  45 gtg gac gtt gtt gct gtg gag ctt tca aag aat act gat tct cag cca     192
Val Asp Val Val Ala Val Glu Leu Ser Lys Asn Thr Asp Ser Gln Pro
    50                  55                  60 agt tct gtg atg ttg ctg gat ttt att caa cac att atg aaa tct acc     240
Ser Ser Val Met Leu Leu Asp Phe Ile Gln His Ile Met Lys Ser Thr
65                  70                  75                  80 cca tta atg ttt ctc agt gca aat aac ggt gat cag tct gct gaa acc     288
Pro Leu Met Phe Leu Ser Ala Asn Asn Gly Asp Gln Ser Ala Glu Thr
                85                  90                  95 aat cag aac tgt gtt gca ttt agc aac tgg atc att tcc cgg ctc tta     336
Asn Gln Asn Cys Val Ala Phe Ser Asn Trp Ile Ile Ser Arg Leu Leu
            100                 105                 110
```

```
                                                          -continued cgc att ggg gct acg cca agc tgc aaa gct ttg cat aga aaa atc gct    384
Arg Ile Gly Ala Thr Pro Ser Cys Lys Ala Leu His Arg Lys Ile Ala
        115                 120                 125 gaa gtc atc cgc tcc ctg ctt ttt ctt ttc aaa aac aag agt tcc ttt    432
Glu Val Ile Arg Ser Leu Leu Phe Leu Phe Lys Asn Lys Ser Ser Phe
130                 135                 140 cta ttt ggt gtt ttt act aaa gat tta tta cat ctc ttt gaa gat ctt    480
Leu Phe Gly Val Phe Thr Lys Asp Leu Leu His Leu Phe Glu Asp Leu
145                 150                 155                 160 atc tac ata cat gaa caa aac atg gag aaa tcc gta gtt tgg cct gtg    528
Ile Tyr Ile His Glu Gln Asn Met Glu Lys Ser Val Val Trp Pro Val
                165                 170                 175 acc att tct aga ttt tta agc aat gca tca gaa aac caa act tgc tta    576
Thr Ile Ser Arg Phe Leu Ser Asn Ala Ser Glu Asn Gln Thr Cys Leu
            180                 185                 190 aga tgc act caa ttt cag ttg ttg aac atg cag aac att gag cct tta    624
Arg Cys Thr Gln Phe Gln Leu Leu Asn Met Gln Asn Ile Glu Pro Leu
        195                 200                 205 gaa tcc act ctg cta atg gtt ttg atg gat aac gaa cat gat att tct    672
Glu Ser Thr Leu Leu Met Val Leu Met Asp Asn Glu His Asp Ile Ser
    210                 215                 220 cca gtg ttt ttc caa agg cag aac ctc ctc ctc tgg ggc att ggg tgc    720
Pro Val Phe Phe Gln Arg Gln Asn Leu Leu Leu Trp Gly Ile Gly Cys
225                 230                 235                 240 tcc ctc ttg gac tat gga agt aca tca ctg aag ata cag gca ttg cat    768
Ser Leu Leu Asp Tyr Gly Ser Thr Ser Leu Lys Ile Gln Ala Leu His
                245                 250                 255 ttt tta aga caa cta ata aaa tta ggt ggt cca cca gaa cag ggt gca    816
Phe Leu Arg Gln Leu Ile Lys Leu Gly Gly Pro Pro Glu Gln Gly Ala
            260                 265                 270 tat ttt ttc ttc att gtg ttt ttt ggg ata cta act tgt ata aaa gac    864
Tyr Phe Phe Phe Ile Val Phe Phe Gly Ile Leu Thr Cys Ile Lys Asp
        275                 280                 285 atg gat tta gaa gaa gtg tct ctt tat gag atg cca ctg ttg aaa ttg    912
Met Asp Leu Glu Glu Val Ser Leu Tyr Glu Met Pro Leu Leu Lys Leu
    290                 295                 300 gta aag gtt ttg ttc cca ttt gaa tca aaa tct tac cta aac att gaa    960
Val Lys Val Leu Phe Pro Phe Glu Ser Lys Ser Tyr Leu Asn Ile Glu
305                 310                 315                 320 cct gtc tat ctg aat atg ttg ctg gag aaa ctt gct gct ctc ttt gat   1008
Pro Val Tyr Leu Asn Met Leu Leu Glu Lys Leu Ala Ala Leu Phe Asp
                325                 330                 335 gga ggt atc ttg agt aat att cag tca gct ccc ttg aaa gaa gct ctt   1056
Gly Gly Ile Leu Ser Asn Ile Gln Ser Ala Pro Leu Lys Glu Ala Leu
            340                 345                 350 tgc tat atg gtc cat tac ttc ctt agc att gtg cct ccg ggc tat gaa   1104
Cys Tyr Met Val His Tyr Phe Leu Ser Ile Val Pro Pro Gly Tyr Glu
        355                 360                 365 tct gcc aaa gaa gtc cga gag gca cat gtt cgc tgc atc tgt aga gct   1152
Ser Ala Lys Glu Val Arg Glu Ala His Val Arg Cys Ile Cys Arg Ala
    370                 375                 380 ttt gtt gat gtc ctt gga ctt cag agc aag caa gaa tac ttg gtc tgc   1200
Phe Val Asp Val Leu Gly Leu Gln Ser Lys Gln Glu Tyr Leu Val Cys
385                 390                 395                 400 ccc ctt cat gaa gca tta aga ata gaa aac ctg gtg ttc atg cag cag   1248
Pro Leu His Glu Ala Leu Arg Ile Glu Asn Leu Val Phe Met Gln Gln
                405                 410                 415 cag cgc atg cag ccc cta agc aca gac tca gag ggt ggt ggg agc agc   1296
Gln Arg Met Gln Pro Leu Ser Thr Asp Ser Glu Gly Gly Gly Ser Ser
            420                 425                 430
```

|   |   |   |   |   |   |   |   |   |   |   |   |   |   |   |   |      |
|---|---|---|---|---|---|---|---|---|---|---|---|---|---|---|---|------|
| agc | agc | gat | gaa | gtg | caa | gag | aaa | cga | cca | cgt | ttg | agt | cta | act | gca | 1344 |
| Ser | Ser | Asp | Glu | Val | Gln | Glu | Lys | Arg | Pro | Arg | Leu | Ser | Leu | Thr | Ala |      |
|     |     |     | 435 |     |     |     | 440 |     |     |     |     | 445 |     |     |     |      |
| aag | cct | cta | aga | aga | aac | aca | cca | tca | gtg | cct | gct | cct | gtg | gat | atg | 1392 |
| Lys | Pro | Leu | Arg | Arg | Asn | Thr | Pro | Ser | Val | Pro | Ala | Pro | Val | Asp | Met |      |
|     | 450 |     |     |     |     | 455 |     |     |     |     | 460 |     |     |     |     |      |
| aag | aca | aag | agc | ata | cta | tgg | aaa | gca | gtg | agt | gcg | aaa | ttc | tcc | tct | 1440 |
| Lys | Thr | Lys | Ser | Ile | Leu | Trp | Lys | Ala | Val | Ser | Ala | Lys | Phe | Ser | Ser |      |
| 465 |     |     |     |     | 470 |     |     |     |     | 475 |     |     |     |     | 480 |      |
| att | ttg | tgc | aaa | ctg | gaa | ggt | gac | gaa | gtt | aca | gat | gaa | gag | atg | gtt | 1488 |
| Ile | Leu | Cys | Lys | Leu | Glu | Gly | Asp | Glu | Val | Thr | Asp | Glu | Glu | Met | Val |      |
|     |     |     |     | 485 |     |     |     |     | 490 |     |     |     |     | 495 |     |      |
| tct | tta | ttg | gag | ggt | ctt | aat | aca | act | gta | cgt | gtt | gct | gct | ctc | aat | 1536 |
| Ser | Leu | Leu | Glu | Gly | Leu | Asn | Thr | Thr | Val | Arg | Val | Ala | Ala | Leu | Asn |      |
|     |     |     | 500 |     |     |     |     | 505 |     |     |     |     | 510 |     |     |      |
| aca | gtt | cat | atc | ttc | act | aat | gat | tcc | aca | gat | act | gat | cag | tta | gta | 1584 |
| Thr | Val | His | Ile | Phe | Thr | Asn | Asp | Ser | Thr | Asp | Thr | Asp | Gln | Leu | Val |      |
|     |     | 515 |     |     |     |     | 520 |     |     |     |     | 525 |     |     |     |      |
| tct | gac | ttg | agc | aat | act | tct | ggc | att | cag | tcg | gta | gaa | ata | gta | cct | 1632 |
| Ser | Asp | Leu | Ser | Asn | Thr | Ser | Gly | Ile | Gln | Ser | Val | Glu | Ile | Val | Pro |      |
|     | 530 |     |     |     |     | 535 |     |     |     |     | 540 |     |     |     |     |      |
| cac | gtt | ttc | tgg | ctc | agt | cca | gag | gat | att | cta | aaa | ata | ctt | aaa | att | 1680 |
| His | Val | Phe | Trp | Leu | Ser | Pro | Glu | Asp | Ile | Leu | Lys | Ile | Leu | Lys | Ile |      |
| 545 |     |     |     |     | 550 |     |     |     |     | 555 |     |     |     |     | 560 |      |
| tgt | aga | aag | gtt | ctt | gat | tct | gca | cac | cag | aga | gcc | aat | ata | aat | gac | 1728 |
| Cys | Arg | Lys | Val | Leu | Asp | Ser | Ala | His | Gln | Arg | Ala | Asn | Ile | Asn | Asp |      |
|     |     |     |     | 565 |     |     |     |     | 570 |     |     |     |     | 575 |     |      |
| att | ctg | atg | aag | ata | ata | aaa | ata | ttt | gat | gca | ata | ctc | tac | att | cat | 1776 |
| Ile | Leu | Met | Lys | Ile | Ile | Lys | Ile | Phe | Asp | Ala | Ile | Leu | Tyr | Ile | His |      |
|     |     |     | 580 |     |     |     |     | 585 |     |     |     |     | 590 |     |     |      |
| gca | gga | aac | aga | tta | aat | gac | caa | act | ctt | aag | gat | ttg | tgc | agc | atg | 1824 |
| Ala | Gly | Asn | Arg | Leu | Asn | Asp | Gln | Thr | Leu | Lys | Asp | Leu | Cys | Ser | Met |      |
|     | 595 |     |     |     |     | 600 |     |     |     |     | 605 |     |     |     |     |      |
| atc | tca | tta | ccc | tgg | ctt | cag | aat | cat | tca | aat | cat | gct | tcc | ttt | aaa | 1872 |
| Ile | Ser | Leu | Pro | Trp | Leu | Gln | Asn | His | Ser | Asn | His | Ala | Ser | Phe | Lys |      |
| 610 |     |     |     |     | 615 |     |     |     |     | 620 |     |     |     |     |     |      |
| gtg | gca | tca | ttt | gac | cca | aca | ttg | atg | acc | ata | agt | gag | cgg | att | ggc | 1920 |
| Val | Ala | Ser | Phe | Asp | Pro | Thr | Leu | Met | Thr | Ile | Ser | Glu | Arg | Ile | Gly |      |
| 625 |     |     |     |     | 630 |     |     |     |     | 635 |     |     |     |     | 640 |      |
| caa | cat | tac | tca | cct | gaa | att | cag | tct | caa | ctt | gtt | ttc | ctc | ctg | tgc | 1968 |
| Gln | His | Tyr | Ser | Pro | Glu | Ile | Gln | Ser | Gln | Leu | Val | Phe | Leu | Leu | Cys |      |
|     |     |     |     | 645 |     |     |     |     | 650 |     |     |     |     | 655 |     |      |
| ctg | ttt | cca | aaa | atg | tta | tgc | cct | gag | tgg | aga | tta | gct | gtg | tac | caa | 2016 |
| Leu | Phe | Pro | Lys | Met | Leu | Cys | Pro | Glu | Trp | Arg | Leu | Ala | Val | Tyr | Gln |      |
|     |     |     | 660 |     |     |     |     | 665 |     |     |     |     | 670 |     |     |      |
| tgg | gca | ttg | gat | agc | cca | cat | gag | att | gtt | cgt | gcc | cgt | tgc | atc | aaa | 2064 |
| Trp | Ala | Leu | Asp | Ser | Pro | His | Glu | Ile | Val | Arg | Ala | Arg | Cys | Ile | Lys |      |
|     | 675 |     |     |     |     | 680 |     |     |     |     | 685 |     |     |     |     |      |
| gga | ttc | cct | gtt | ctt | ctg | tgc | aat | gtt | agc | cag | cag | ggg | tat | ggt | cca | 2112 |
| Gly | Phe | Pro | Val | Leu | Leu | Cys | Asn | Val | Ser | Gln | Gln | Gly | Tyr | Gly | Pro |      |
|     | 690 |     |     |     |     | 695 |     |     |     |     | 700 |     |     |     |     |      |
| att | ccc | aag | att | tta | atc | gac | tgt | ttg | aat | gat | gcc | tct | gag | ctg | gtg | 2160 |
| Ile | Pro | Lys | Ile | Leu | Ile | Asp | Cys | Leu | Asn | Asp | Ala | Ser | Glu | Leu | Val |      |
| 705 |     |     |     |     | 710 |     |     |     |     | 715 |     |     |     |     | 720 |      |
| aag | aag | gag | tta | gcc | aac | tca | gtg | ggt | atg | ttt | gcc | tcc | ggc | ctt | gct | 2208 |
| Lys | Lys | Glu | Leu | Ala | Asn | Ser | Val | Gly | Met | Phe | Ala | Ser | Gly | Leu | Ala |      |
|     |     |     |     | 725 |     |     |     |     | 730 |     |     |     |     | 735 |     |      |
| tgc | ggt | ttt | gag | ctg | caa | tat | tcc | cca | acg | gca | cct | act | gca | gca | gaa | 2256 |
| Cys | Gly | Phe | Glu | Leu | Gln | Tyr | Ser | Pro | Thr | Ala | Pro | Thr | Ala | Ala | Glu |      |

```
                        740                 745                 750
tct gag ttc ctt tgt agc agc ctg aca gtt act gct tta ccc tca tcg      2304
Ser Glu Phe Leu Cys Ser Ser Leu Thr Val Thr Ala Leu Pro Ser Ser
        755                 760                 765 aaa ctt tct cgt atg acc gcc tct gca tta aaa cca ttc ctg gca ctg      2352
Lys Leu Ser Arg Met Thr Ala Ser Ala Leu Lys Pro Phe Leu Ala Leu
    770                 775                 780 ctt aat cga aac atg cca agc tcc gtc aaa atg gca ttt att gaa aat      2400
Leu Asn Arg Asn Met Pro Ser Ser Val Lys Met Ala Phe Ile Glu Asn
785                 790                 795                 800 atg ccc atg ctg ttt gct cac ctc tct ctt gag aaa gat gat ttg gat      2448
Met Pro Met Leu Phe Ala His Leu Ser Leu Glu Lys Asp Asp Leu Asp
                805                 810                 815 tcc cga act gtg att gaa tca ttg tta aac cta atg gag gac cca gac      2496
Ser Arg Thr Val Ile Glu Ser Leu Leu Asn Leu Met Glu Asp Pro Asp
            820                 825                 830 aag gat gta agg aca gct ttc agt ggg aac atc aaa cac ctg ttg gcg      2544
Lys Asp Val Arg Thr Ala Phe Ser Gly Asn Ile Lys His Leu Leu Ala
        835                 840                 845 tgt gca gac tgt gag gac gga tat cta aag gag att gta gtc tca agg      2592
Cys Ala Asp Cys Glu Asp Gly Tyr Leu Lys Glu Ile Val Val Ser Arg
    850                 855                 860 atg aaa aaa gca tat aca gat gcc aag atg tcg cgt gac aat gag atg      2640
Met Lys Lys Ala Tyr Thr Asp Ala Lys Met Ser Arg Asp Asn Glu Met
865                 870                 875                 880 aag gac act ctc att ctt aca act ggg gat ata gga agg gca gca aaa      2688
Lys Asp Thr Leu Ile Leu Thr Thr Gly Asp Ile Gly Arg Ala Ala Lys
                885                 890                 895 gga gag ttg gta cca ttt gca ctg ttg cat ctg ctg cat tgc ctg ctg      2736
Gly Glu Leu Val Pro Phe Ala Leu Leu His Leu Leu His Cys Leu Leu
            900                 905                 910 tct aaa tcc cca tgt gtg gca ggt gct tct tac aca gaa atc cga tct      2784
Ser Lys Ser Pro Cys Val Ala Gly Ala Ser Tyr Thr Glu Ile Arg Ser
        915                 920                 925 ctt gca gca gca aag tcc acc agt ctg cat atc ttt ttt agc cag tac      2832
Leu Ala Ala Ala Lys Ser Thr Ser Leu His Ile Phe Phe Ser Gln Tyr
    930                 935                 940 aag aaa ccg att tgt cag ttc ctt ata gaa tcg ctt cac tca agc cag      2880
Lys Lys Pro Ile Cys Gln Phe Leu Ile Glu Ser Leu His Ser Ser Gln
945                 950                 955                 960 gca gcc ctt ctg acc aac aca cct ggc cgc agc agt gaa atg cag aag      2928
Ala Ala Leu Leu Thr Asn Thr Pro Gly Arg Ser Ser Glu Met Gln Lys
                965                 970                 975 cag gag gca aca cat cat agg gaa gct gca ctt gac atc tta tcc gaa      2976
Gln Glu Ala Thr His His Arg Glu Ala Ala Leu Asp Ile Leu Ser Glu
            980                 985                 990 ata gca aat gta ttt gat ttc cca  gac tta aac cgc ttt  tta acg agg    3024
Ile Ala Asn Val Phe Asp Phe Pro  Asp Leu Asn Arg Phe  Leu Thr Arg
        995                 1000                1005 act ttg  caa ctt ttg ctt cca  tat ctt gct gcc aaa  gct agt cca       3069
Thr Leu  Gln Leu Leu Leu Pro  Tyr Leu Ala Ala Lys  Ala Ser Pro
    1010                1015                1020 aca gcc tct act ctg ata aga  acg att gcc aaa caa  ctt aat gtg        3114
Thr Ala Ser Thr Leu Ile Arg  Thr Ile Ala Lys Gln  Leu Asn Val
    1025                1030                1035 aat cga  agg gag atc ctg atc  aat aac ttc aag tat  ata ttc tct       3159
Asn Arg  Arg Glu Ile Leu Ile  Asn Asn Phe Lys Tyr  Ile Phe Ser
    1040                1045                1050 cac ttg  gtt tgt tct tgc aca  aaa gat gag ctg gaa  aag tcg ctt       3204
```

```
                His Leu Val Cys Ser Cys Thr Lys Asp Glu Leu Glu Lys Ser Leu
                    1055                1060                1065 cat tac cta aag aat gaa aca gaa att gag ctg ggt agt tta ctg           3249
His Tyr Leu Lys Asn Glu Thr Glu Ile Glu Leu Gly Ser Leu Leu
    1070                1075                1080 aga cag gac tac cag gga ctg cac aat gaa cta ctt ttg cgc ctg           3294
Arg Gln Asp Tyr Gln Gly Leu His Asn Glu Leu Leu Leu Arg Leu
    1085                1090                1095 ggt gag cac tat cag cag gtc ttt agt ggg ctg tcc ata tta gca           3339
Gly Glu His Tyr Gln Gln Val Phe Ser Gly Leu Ser Ile Leu Ala
    1100                1105                1110 aca tat gca tcc aac gat gat cca tat cag gga cct agg aat ttt           3384
Thr Tyr Ala Ser Asn Asp Asp Pro Tyr Gln Gly Pro Arg Asn Phe
    1115                1120                1125 gca aag cca gaa ata atg gca gat tat ttg caa cca aag ctt tta           3429
Ala Lys Pro Glu Ile Met Ala Asp Tyr Leu Gln Pro Lys Leu Leu
    1130                1135                1140 gga att ttg gct ttc ttt aat atg cac ctg ttg agc tcc agc att           3474
Gly Ile Leu Ala Phe Phe Asn Met His Leu Leu Ser Ser Ser Ile
    1145                1150                1155 ggc att gaa gac aag aaa atg gcc ttg aac agt ctg gtt tct tta           3519
Gly Ile Glu Asp Lys Lys Met Ala Leu Asn Ser Leu Val Ser Leu
    1160                1165                1170 atg aaa ctg atg gga cca aag cat ata agt tcc gtt agg gtc aag           3564
Met Lys Leu Met Gly Pro Lys His Ile Ser Ser Val Arg Val Lys
    1175                1180                1185 atg atg acg acc ttg aga act ggc cta cgt tat aaa gag gaa ttt           3609
Met Met Thr Thr Leu Arg Thr Gly Leu Arg Tyr Lys Glu Glu Phe
    1190                1195                1200 ccg ggg ctt tgc tgc agt gca tgg gac ttg ttt gtt cgc tgc ctg           3654
Pro Gly Leu Cys Cys Ser Ala Trp Asp Leu Phe Val Arg Cys Leu
    1205                1210                1215 gat caa gcc tat ctg ggc ccg ctc ctc agt cat gtg att gtt gca           3699
Asp Gln Ala Tyr Leu Gly Pro Leu Leu Ser His Val Ile Val Ala
    1220                1225                1230 ctg ttg cct ctg ttg cac atc cag cct aaa gaa act gtt gct gtg           3744
Leu Leu Pro Leu Leu His Ile Gln Pro Lys Glu Thr Val Ala Val
    1235                1240                1245 ttc cgc tat ctc ata gta gag aac agg gat gct gtt cag gat ttc           3789
Phe Arg Tyr Leu Ile Val Glu Asn Arg Asp Ala Val Gln Asp Phe
    1250                1255                1260 ctt cat gaa ata tat ttt ctg cct gat cat cca gaa ttg aaa gaa           3834
Leu His Glu Ile Tyr Phe Leu Pro Asp His Pro Glu Leu Lys Glu
    1265                1270                1275 atc cag aag gtt cta caa gaa tac agg aaa gaa acc acc aaa agc           3879
Ile Gln Lys Val Leu Gln Glu Tyr Arg Lys Glu Thr Thr Lys Ser
    1280                1285                1290 aca gat ctg cag aca gcc atg cag ctg tct att cga gcc att cag           3924
Thr Asp Leu Gln Thr Ala Met Gln Leu Ser Ile Arg Ala Ile Gln
    1295                1300                1305 cat gaa aat gtg gat gtt cgc atg cat gcc ctt act agt ctg aaa           3969
His Glu Asn Val Asp Val Arg Met His Ala Leu Thr Ser Leu Lys
    1310                1315                1320 gaa aca ctc tac aag aac cag gct aaa ctg ttg cag tat tca aca           4014
Glu Thr Leu Tyr Lys Asn Gln Ala Lys Leu Leu Gln Tyr Ser Thr
    1325                1330                1335 gac agt gaa act gta gaa cca gtt atc tcc cag ctg gta aca gtt           4059
Asp Ser Glu Thr Val Glu Pro Val Ile Ser Gln Leu Val Thr Val
    1340                1345                1350
```

```
ctc tta att gga tgc caa gat gcc aat cca caa gcc cgt cta ttt      4104
Leu Leu Ile Gly Cys Gln Asp Ala Asn Pro Gln Ala Arg Leu Phe
    1355                1360                1365 tgt ggt gaa tgc ctt ggc caa ctt gga gcc att gat cct ggg aga      4149
Cys Gly Glu Cys Leu Gly Gln Leu Gly Ala Ile Asp Pro Gly Arg
1370                1375                1380 ttg gat ttc tca ccc agt gaa aca caa ggg aaa ggt ttt act ttt      4194
Leu Asp Phe Ser Pro Ser Glu Thr Gln Gly Lys Gly Phe Thr Phe
            1385                1390                1395 gtt tca gga gtt gaa gat tca gac ttt gcc tat gag ttg ctc aca      4239
Val Ser Gly Val Glu Asp Ser Asp Phe Ala Tyr Glu Leu Leu Thr
        1400                1405                1410 gag caa act aga gca ttt ctt gcc tat gct gat aat gtc cgc gcc      4284
Glu Gln Thr Arg Ala Phe Leu Ala Tyr Ala Asp Asn Val Arg Ala
    1415                1420                1425 cag gac tct gct gcc tat gct ata cag gag ctc ctc tct atc ttc      4329
Gln Asp Ser Ala Ala Tyr Ala Ile Gln Glu Leu Leu Ser Ile Phe
1430                1435                1440 gag tgc aaa gaa gga agg act gat tgt cct ggg cgt agg ctg tgg      4374
Glu Cys Lys Glu Gly Arg Thr Asp Cys Pro Gly Arg Arg Leu Trp
            1445                1450                1455 agg aga ttc cca gaa cat gtt caa gaa ata ttg gag cca cat ctt      4419
Arg Arg Phe Pro Glu His Val Gln Glu Ile Leu Glu Pro His Leu
        1460                1465                1470 aat act aga tac aag agt tcc aga aag gct gta aac tgg tcc aga      4464
Asn Thr Arg Tyr Lys Ser Ser Arg Lys Ala Val Asn Trp Ser Arg
    1475                1480                1485 gtg aaa aag ccc att tat ttg agc aag tta gga aat aac ttt gca      4509
Val Lys Lys Pro Ile Tyr Leu Ser Lys Leu Gly Asn Asn Phe Ala
1490                1495                1500 gac tgg tca gca aca tgg gca ggt tac ctc ata act aag gtt cga      4554
Asp Trp Ser Ala Thr Trp Ala Gly Tyr Leu Ile Thr Lys Val Arg
            1505                1510                1515 cat gag ctt gcc agg aga gtt ttc agc tgt tgt agt ata atg atg      4599
His Glu Leu Ala Arg Arg Val Phe Ser Cys Cys Ser Ile Met Met
        1520                1525                1530 aag cat gac ttc aaa gtg acc att tat ctg ctc cca cat att ttg      4644
Lys His Asp Phe Lys Val Thr Ile Tyr Leu Leu Pro His Ile Leu
    1535                1540                1545 gtc tat gtt ttg ttg gga tgt aac aaa gaa gat cag caa gag gta      4689
Val Tyr Val Leu Leu Gly Cys Asn Lys Glu Asp Gln Gln Glu Val
1550                1555                1560 tat gca gaa att atg gca gtg tta aag cat gaa gat cca cta atg      4734
Tyr Ala Glu Ile Met Ala Val Leu Lys His Glu Asp Pro Leu Met
            1565                1570                1575 cgt cgg tta cag gac agc gcc tca gat ctg agt cag ctc agc acc      4779
Arg Arg Leu Gln Asp Ser Ala Ser Asp Leu Ser Gln Leu Ser Thr
        1580                1585                1590 caa aca gtc ttt tca atg ctt gat cat ctt act cag tgg gca cgg      4824
Gln Thr Val Phe Ser Met Leu Asp His Leu Thr Gln Trp Ala Arg
    1595                1600                1605 gag aaa ttc cag gca cta aat gct gag aaa aca aat ccc aaa cca      4869
Glu Lys Phe Gln Ala Leu Asn Ala Glu Lys Thr Asn Pro Lys Pro
1610                1615                1620 gga acc aga ggg gaa cca aag gca gtg tct aat gaa gac tat gga      4914
Gly Thr Arg Gly Glu Pro Lys Ala Val Ser Asn Glu Asp Tyr Gly
            1625                1630                1635 gag tat cag aat gta aca agg ttt tta gat ctt ata ccg cag gat      4959
Glu Tyr Gln Asn Val Thr Arg Phe Leu Asp Leu Ile Pro Gln Asp
        1640                1645                1650
```

```
act ttg gct gtt gct tcc ttt cgt tcc aaa gct tat act aga gct    5004
Thr Leu Ala Val Ala Ser Phe Arg Ser Lys Ala Tyr Thr Arg Ala
    1655                1660                1665 ctc atg cat ttt gaa tcc ttt ata atg gaa aag aaa caa gaa att    5049
Leu Met His Phe Glu Ser Phe Ile Met Glu Lys Lys Gln Glu Ile
    1670                1675                1680 cag gag cac ctt gga ttt ctt cag aaa ctg tat gct gct atg cat    5094
Gln Glu His Leu Gly Phe Leu Gln Lys Leu Tyr Ala Ala Met His
    1685                1690                1695 gag cca gat gga gta gct ggg gta agc gcc att cgc aag aaa gaa    5139
Glu Pro Asp Gly Val Ala Gly Val Ser Ala Ile Arg Lys Lys Glu
    1700                1705                1710 gct tct ctg aaa gaa cag atc ttg gag cat gaa agt att ggt ctg    5184
Ala Ser Leu Lys Glu Gln Ile Leu Glu His Glu Ser Ile Gly Leu
    1715                1720                1725 ttg aga gat gcc act gct tgc tat gat aga gct att cag cta aag    5229
Leu Arg Asp Ala Thr Ala Cys Tyr Asp Arg Ala Ile Gln Leu Lys
    1730                1735                1740 cct gag gag ata att cac tat cat ggg gta gtg aaa tct atg ctt    5274
Pro Glu Glu Ile Ile His Tyr His Gly Val Val Lys Ser Met Leu
    1745                1750                1755 ggt ctt ggc cag ttg tct act gta att acg caa gtt aac gga att    5319
Gly Leu Gly Gln Leu Ser Thr Val Ile Thr Gln Val Asn Gly Ile
    1760                1765                1770 ttg aat agc agg tcg gaa tgg aca gct gaa cta aac aca tac aga    5364
Leu Asn Ser Arg Ser Glu Trp Thr Ala Glu Leu Asn Thr Tyr Arg
    1775                1780                1785 gta gaa gca gca tgg aaa ctc tca cag tgg gat tta gtg gag gaa    5409
Val Glu Ala Ala Trp Lys Leu Ser Gln Trp Asp Leu Val Glu Glu
    1790                1795                1800 tac tta tct gca gac aga aaa tct acc aca tgg agc att agg ctg    5454
Tyr Leu Ser Ala Asp Arg Lys Ser Thr Thr Trp Ser Ile Arg Leu
    1805                1810                1815 ggg caa ctc ctg ctt tca gct aaa aag ggg gag aga gat atg ttt    5499
Gly Gln Leu Leu Leu Ser Ala Lys Lys Gly Glu Arg Asp Met Phe
    1820                1825                1830 tat gaa acg ctc aaa gta gtc cga gcc gaa caa att gtt cca ctg    5544
Tyr Glu Thr Leu Lys Val Val Arg Ala Glu Gln Ile Val Pro Leu
    1835                1840                1845 tct gct gcc agc ttt gag agg ggc tcc tac caa cga gga tat gag    5589
Ser Ala Ala Ser Phe Glu Arg Gly Ser Tyr Gln Arg Gly Tyr Glu
    1850                1855                1860 tac ata gta agg ttg cac atg tta tgt gag ttg gag cac agt gta    5634
Tyr Ile Val Arg Leu His Met Leu Cys Glu Leu Glu His Ser Val
    1865                1870                1875 aaa atg ttt ctt cag aaa cct tct gtt gag cct gca gta gac tct    5679
Lys Met Phe Leu Gln Lys Pro Ser Val Glu Pro Ala Val Asp Ser
    1880                1885                1890 tta aac ttg cca gca cgg cta gaa atg aca cag aat tcc tac aga    5724
Leu Asn Leu Pro Ala Arg Leu Glu Met Thr Gln Asn Ser Tyr Arg
    1895                1900                1905 gca aga gag ccc att ttg gca gtt cgc agg gca cta caa aca atc    5769
Ala Arg Glu Pro Ile Leu Ala Val Arg Arg Ala Leu Gln Thr Ile
    1910                1915                1920 aac aaa agg cct aat cat gca gat atg att ggt gag tgt tgg ctg    5814
Asn Lys Arg Pro Asn His Ala Asp Met Ile Gly Glu Cys Trp Leu
    1925                1930                1935 caa agt gct cga gtt gcg cgt aag gct ggg cat cac cag act gct    5859
Gln Ser Ala Arg Val Ala Arg Lys Ala Gly His His Gln Thr Ala
```

-continued

|  | 1940 |  |  |  | 1945 |  |  |  | 1950 |  |  |  |  |
|---|---|---|---|---|---|---|---|---|---|---|---|---|---|
| tac<br>Tyr | aat<br>Asn<br>1955 | gct<br>Ala | ctg<br>Leu | ctt<br>Leu | aat<br>Asn<br>1960 | gct<br>Ala | ggg<br>Gly | gag<br>Glu | tcc<br>Ser | aga<br>Arg | ttg<br>Leu<br>1965 | tct<br>Ser | gag<br>Glu | ctc<br>Leu | 5904 |
| aat<br>Asn | gtt<br>Val<br>1970 | gaa<br>Glu | cgg<br>Arg | gcg<br>Ala | aag<br>Lys<br>1975 | tgg<br>Trp | ctc<br>Leu | tgg<br>Trp | tcc<br>Ser | aag<br>Lys | ggt<br>Gly<br>1980 | gat<br>Asp | gta<br>Val | cat<br>His | 5949 |
| caa<br>Gln | gct<br>Ala<br>1985 | ctc<br>Leu | att<br>Ile | gtt<br>Val | ctc<br>Leu<br>1990 | cag<br>Gln | aag<br>Lys | gga<br>Gly | gca<br>Ala | gaa<br>Glu | ctg<br>Leu<br>1995 | ttc<br>Phe | ctg<br>Leu | tca<br>Ser | 5994 |
| agt<br>Ser | acc<br>Thr<br>2000 | agc<br>Ser | gct<br>Ala | cca<br>Pro | cca<br>Pro<br>2005 | gaa<br>Glu | cag<br>Gln | cag<br>Gln | ctt<br>Leu | atc<br>Ile | cat<br>His<br>2010 | ggc<br>Gly | aga<br>Arg | gcc<br>Ala | 6039 |
| atg<br>Met | ctg<br>Leu<br>2015 | ctg<br>Leu | gtg<br>Val | ggc<br>Gly | cgt<br>Arg<br>2020 | ttg<br>Leu | atg<br>Met | gaa<br>Glu | gag<br>Glu | act<br>Thr | gcc<br>Ala<br>2025 | aac<br>Asn | ttt<br>Phe | gaa<br>Glu | 6084 |
| agc<br>Ser | aac<br>Asn<br>2030 | gct<br>Ala | gtg<br>Val | atg<br>Met | aag<br>Lys<br>2035 | aaa<br>Lys | tat<br>Tyr | aaa<br>Lys | gat<br>Asp | gta<br>Val | aca<br>Thr<br>2040 | gca<br>Ala | ctg<br>Leu | ttg<br>Leu | 6129 |
| cct<br>Pro | gaa<br>Glu<br>2045 | tgg<br>Trp | gaa<br>Glu | gat<br>Asp | ggc<br>Gly<br>2050 | cat<br>His | ttt<br>Phe | tat<br>Tyr | ctt<br>Leu | gcc<br>Ala | aag<br>Lys<br>2055 | tac<br>Tyr | tat<br>Tyr | gac<br>Asp | 6174 |
| aaa<br>Lys | ctc<br>Leu<br>2060 | atg<br>Met | cca<br>Pro | atg<br>Met | gtt<br>Val<br>2065 | act<br>Thr | gat<br>Asp | aac<br>Asn | aag<br>Lys | atg<br>Met | gag<br>Glu<br>2070 | aag<br>Lys | caa<br>Gln | gga<br>Gly | 6219 |
| gac<br>Asp | ttg<br>Leu<br>2075 | ata<br>Ile | cga<br>Arg | tat<br>Tyr | ata<br>Ile<br>2080 | gta<br>Val | ctt<br>Leu | ccc<br>Pro | ttt<br>Phe | gga<br>Gly | agg<br>Arg<br>2085 | tct<br>Ser | tta<br>Leu | cag<br>Gln | 6264 |
| ttc<br>Phe | gga<br>Gly<br>2090 | aac<br>Asn | caa<br>Gln | tat<br>Tyr | att<br>Ile<br>2095 | tat<br>Tyr | caa<br>Gln | tcg<br>Ser | atg<br>Met | cca<br>Pro | cgt<br>Arg<br>2100 | atg<br>Met | ctt<br>Leu | tca<br>Ser | 6309 |
| ctt<br>Leu | tgg<br>Trp<br>2105 | ctg<br>Leu | gat<br>Asp | ttt<br>Phe | gga<br>Gly<br>2110 | gct<br>Ala | aaa<br>Lys | gtt<br>Val | tat<br>Tyr | gaa<br>Glu | tgg<br>Trp<br>2115 | gaa<br>Glu | aaa<br>Lys | gct<br>Ala | 6354 |
| ggt<br>Gly | cgt<br>Arg<br>2120 | gct<br>Ala | gac<br>Asp | aga<br>Arg | tta<br>Leu<br>2125 | caa<br>Gln | atg<br>Met | aaa<br>Lys | aat<br>Asn | gaa<br>Glu | ttg<br>Leu<br>2130 | atg<br>Met | aaa<br>Lys | ata<br>Ile | 6399 |
| aat<br>Asn | aag<br>Lys<br>2135 | gtc<br>Val | ata<br>Ile | tct<br>Ser | gac<br>Asp<br>2140 | cat<br>His | aaa<br>Lys | aac<br>Asn | cag<br>Gln | ctt<br>Leu | gct<br>Ala<br>2145 | cct<br>Pro | tat<br>Tyr | cag<br>Gln | 6444 |
| ttc<br>Phe | ctt<br>Leu<br>2150 | aca<br>Thr | gct<br>Ala | ttc<br>Phe | tca<br>Ser<br>2155 | cag<br>Gln | cta<br>Leu | atc<br>Ile | tcc<br>Ser | aga<br>Arg | ata<br>Ile<br>2160 | tgt<br>Cys | cac<br>His | tct<br>Ser | 6489 |
| cat<br>His | gat<br>Asp<br>2165 | gag<br>Glu | gtg<br>Val | ttt<br>Phe | gct<br>Ala<br>2170 | gtg<br>Val | ttg<br>Leu | atg<br>Met | gaa<br>Glu | att<br>Ile | gtg<br>Val<br>2175 | gct<br>Ala | aag<br>Lys | gtg<br>Val | 6534 |
| ttt<br>Phe | gtg<br>Val<br>2180 | gca<br>Ala | tac<br>Tyr | ccc<br>Pro | cag<br>Gln<br>2185 | cag<br>Gln | gca<br>Ala | atg<br>Met | tgg<br>Trp | atg<br>Met | atg<br>Met<br>2190 | act<br>Thr | gct<br>Ala | gtg<br>Val | 6579 |
| tct<br>Ser | aag<br>Lys<br>2195 | tca<br>Ser | tca<br>Ser | tat<br>Tyr | cca<br>Pro<br>2200 | atg<br>Met | cgt<br>Arg | gta<br>Val | aac<br>Asn | aga<br>Arg | tgc<br>Cys<br>2205 | aaa<br>Lys | gag<br>Glu | ata<br>Ile | 6624 |
| ctc<br>Leu | gag<br>Glu<br>2210 | aag<br>Lys | gcc<br>Ala | ata<br>Ile | cat<br>His<br>2215 | atg<br>Met | aag<br>Lys | cca<br>Pro | tcc<br>Ser | cta<br>Leu | gga<br>Gly<br>2220 | aaa<br>Lys | ttt<br>Phe | att<br>Ile | 6669 |
| gga<br>Gly | gat<br>Asp<br>2225 | gca<br>Ala | act<br>Thr | cgc<br>Arg | ctc<br>Leu<br>2230 | act<br>Thr | gat<br>Asp | aaa<br>Lys | cta<br>Leu | cta<br>Leu | gag<br>Glu<br>2235 | ctc<br>Leu | tgc<br>Cys | aat<br>Asn | 6714 |
| aag<br>Lys | ccg<br>Pro | gtg<br>Val | gat<br>Asp | gga<br>Gly | aat<br>Asn | act<br>Thr | agc<br>Ser | acc<br>Thr | ctc<br>Leu | agt<br>Ser | atg<br>Met | aat<br>Asn | atc<br>Ile | cac<br>His | 6759 |

| | | | | | | | | | | | | |
|---|---|---|---|---|---|---|---|---|---|---|---|---|
|Lys|Pro|Val|Asp|Gly|Asn|Thr|Ser|Thr|Leu|Ser|Met|Asn Ile His|
| |2240| | | |2245| | | |2250| | | |

| | | | | | | | | | | | | | |
|---|---|---|---|---|---|---|---|---|---|---|---|---|---|
|ttc|aaa|atg|ctg|aag|aaa|cta|gta|gaa|gaa|aca|aca|ttt agt gaa|6804|
|Phe|Lys|Met|Leu|Lys|Lys|Leu|Val|Glu|Glu|Thr|Thr|Phe Ser Glu| |
| |2255| | | |2260| | | |2265| | | | |

| | | | | | | | | | | | | | |
|---|---|---|---|---|---|---|---|---|---|---|---|---|---|
|atc|ctt|att|cct|cta|cag|tcc|gtg|atg|att|ccc|acc|cta ccg tct|6849|
|Ile|Leu|Ile|Pro|Leu|Gln|Ser|Val|Met|Ile|Pro|Thr|Leu Pro Ser| |
| |2270| | | |2275| | | |2280| | | | |

| | | | | | | | | | | | | | |
|---|---|---|---|---|---|---|---|---|---|---|---|---|---|
|act|gca|ggg|aag|cgt|gac|cat|gct|gat|cat|gat|cca|ttc cct ggc|6894|
|Thr|Ala|Gly|Lys|Arg|Asp|His|Ala|Asp|His|Asp|Pro|Phe Pro Gly| |
| |2285| | | |2290| | | |2295| | | | |

| | | | | | | | | | | | | | |
|---|---|---|---|---|---|---|---|---|---|---|---|---|---|
|cac|tgg|gct|tac|ctc|tca|ggc|ttt|gat|gac|gcg|gta|gag att ctg|6939|
|His|Trp|Ala|Tyr|Leu|Ser|Gly|Phe|Asp|Asp|Ala|Val|Glu Ile Leu| |
| |2300| | | |2305| | | |2310| | | | |

| | | | | | | | | | | | | | |
|---|---|---|---|---|---|---|---|---|---|---|---|---|---|
|cct|tct|ctc|cag|aaa|cca|aag|aaa|att|tct|cta|aag|gga tca gac|6984|
|Pro|Ser|Leu|Gln|Lys|Pro|Lys|Lys|Ile|Ser|Leu|Lys|Gly Ser Asp| |
| |2315| | | |2320| | | |2325| | | | |

| | | | | | | | | | | | | | |
|---|---|---|---|---|---|---|---|---|---|---|---|---|---|
|ggt|aaa|tca|tac|att|atg|atg|tgt|aaa|cca|aaa|gat|gat ctt aga|7029|
|Gly|Lys|Ser|Tyr|Ile|Met|Met|Cys|Lys|Pro|Lys|Asp|Asp Leu Arg| |
| |2330| | | |2335| | | |2340| | | | |

| | | | | | | | | | | | | | |
|---|---|---|---|---|---|---|---|---|---|---|---|---|---|
|aag|gac|tgc|cgg|ctg|atg|gaa|ttt|aac|tct|tta|atc|aac aag tgt|7074|
|Lys|Asp|Cys|Arg|Leu|Met|Glu|Phe|Asn|Ser|Leu|Ile|Asn Lys Cys| |
| |2345| | | |2350| | | |2355| | | | |

| | | | | | | | | | | | | | |
|---|---|---|---|---|---|---|---|---|---|---|---|---|---|
|tta|cgc|aaa|ggt|gca|gaa|tca|cga|agg|aga|gag|ctt|cat att cga|7119|
|Leu|Arg|Lys|Gly|Ala|Glu|Ser|Arg|Arg|Arg|Glu|Leu|His Ile Arg| |
| |2360| | | |2365| | | |2370| | | | |

| | | | | | | | | | | | | | |
|---|---|---|---|---|---|---|---|---|---|---|---|---|---|
|acc|tat|gct|gtc|att|cca|ctg|aat|gac|gaa|tgc|ggc|atc ata gag|7164|
|Thr|Tyr|Ala|Val|Ile|Pro|Leu|Asn|Asp|Glu|Cys|Gly|Ile Ile Glu| |
| |2375| | | |2380| | | |2385| | | | |

| | | | | | | | | | | | | | |
|---|---|---|---|---|---|---|---|---|---|---|---|---|---|
|tgg|gtg|aat|aat|act|gca|gga|ttc|cgg|aac|ata|ttg|atc aag ctg|7209|
|Trp|Val|Asn|Asn|Thr|Ala|Gly|Phe|Arg|Asn|Ile|Leu|Ile Lys Leu| |
| |2390| | | |2395| | | |2400| | | | |

| | | | | | | | | | | | | | |
|---|---|---|---|---|---|---|---|---|---|---|---|---|---|
|tac|aag|gaa|aaa|ggc|att|tac|atg|ggt|gga|aag|gaa|ttg cgg cag|7254|
|Tyr|Lys|Glu|Lys|Gly|Ile|Tyr|Met|Gly|Gly|Lys|Glu|Leu Arg Gln| |
| |2405| | | |2410| | | |2415| | | | |

| | | | | | | | | | | | | | |
|---|---|---|---|---|---|---|---|---|---|---|---|---|---|
|tgt|atg|ctt|ccc|aag|agc|gca|cca|cta|caa|gaa|aag|ctg aaa gtc|7299|
|Cys|Met|Leu|Pro|Lys|Ser|Ala|Pro|Leu|Gln|Glu|Lys|Leu Lys Val| |
| |2420| | | |2425| | | |2430| | | | |

| | | | | | | | | | | | | | |
|---|---|---|---|---|---|---|---|---|---|---|---|---|---|
|ttt|aag|gag|gcc|cta|ctg|cct|cgt|cac|ccc|cca|ttg|ttc cat gaa|7344|
|Phe|Lys|Glu|Ala|Leu|Leu|Pro|Arg|His|Pro|Pro|Leu|Phe His Glu| |
| |2435| | | |2440| | | |2445| | | | |

| | | | | | | | | | | | | | |
|---|---|---|---|---|---|---|---|---|---|---|---|---|---|
|tgg|ttt|tta|aga|aca|ttt|cct|gat|cct|act|tct|tgg|tat aac agc|7389|
|Trp|Phe|Leu|Arg|Thr|Phe|Pro|Asp|Pro|Thr|Ser|Trp|Tyr Asn Ser| |
| |2450| | | |2455| | | |2460| | | | |

| | | | | | | | | | | | | | |
|---|---|---|---|---|---|---|---|---|---|---|---|---|---|
|aga|tca|gcc|tat|tgc|cgt|tcc|act|gct|gtg|atg|tct|atg gta ggt|7434|
|Arg|Ser|Ala|Tyr|Cys|Arg|Ser|Thr|Ala|Val|Met|Ser|Met Val Gly| |
| |2465| | | |2470| | | |2475| | | | |

| | | | | | | | | | | | | | |
|---|---|---|---|---|---|---|---|---|---|---|---|---|---|
|tac|ata|ctg|ggc|cta|ggg|gac|cgc|cat|gga|gaa|aac|att ctt ttt|7479|
|Tyr|Ile|Leu|Gly|Leu|Gly|Asp|Arg|His|Gly|Glu|Asn|Ile Leu Phe| |
| |2480| | | |2485| | | |2490| | | | |

| | | | | | | | | | | | | | |
|---|---|---|---|---|---|---|---|---|---|---|---|---|---|
|gac|tcg|ctt|act|ggg|gaa|tgt|gtc|cat|gtg|gat|ttt|aac tgc ctc|7524|
|Asp|Ser|Leu|Thr|Gly|Glu|Cys|Val|His|Val|Asp|Phe|Asn Cys Leu| |
| |2495| | | |2500| | | |2505| | | | |

| | | | | | | | | | | | | | |
|---|---|---|---|---|---|---|---|---|---|---|---|---|---|
|ttc|aac|aag|ggt|gaa|aca|ttt|gaa|gtt|cca|gag|att|gtc ccc ttc|7569|
|Phe|Asn|Lys|Gly|Glu|Thr|Phe|Glu|Val|Pro|Glu|Ile|Val Pro Phe| |
| |2510| | | |2515| | | |2520| | | | |

| | | | | | | | | | | | | | |
|---|---|---|---|---|---|---|---|---|---|---|---|---|---|
|cga|cta|aca|cat|aac|atg|gtc|aat|ggt|atg|ggc|ccc|atg ggg acg|7614|
|Arg|Leu|Thr|His|Asn|Met|Val|Asn|Gly|Met|Gly|Pro|Met Gly Thr| |
| |2525| | | |2530| | | |2535| | | | |

```
gag gga ctt ttt cga cgt gca tgt gag gtc atc atg agg tta atg    7659
Glu Gly Leu Phe Arg Arg Ala Cys Glu Val Ile Met Arg Leu Met
    2540            2545                2550 aga gaa cag agg gag tca ctt atg agt gtg ctg aaa ccc ttt tta    7704
Arg Glu Gln Arg Glu Ser Leu Met Ser Val Leu Lys Pro Phe Leu
    2555            2560                2565 cat gat cct ttg gtg gaa tgg agt aaa cca gca aga ggg agt agt    7749
His Asp Pro Leu Val Glu Trp Ser Lys Pro Ala Arg Gly Ser Ser
    2570            2575                2580 aaa ggt caa gtc aac gag aca gga gaa gtg atg aat gaa aag gcc    7794
Lys Gly Gln Val Asn Glu Thr Gly Glu Val Met Asn Glu Lys Ala
    2585            2590                2595 aaa aca cat gtg ctt gac ata gag cag agg cta caa ggt gtg att    7839
Lys Thr His Val Leu Asp Ile Glu Gln Arg Leu Gln Gly Val Ile
    2600            2605                2610 aag acc agg aat cgt gta aag gga ctt ccg ctg tcc att gaa gga    7884
Lys Thr Arg Asn Arg Val Lys Gly Leu Pro Leu Ser Ile Glu Gly
    2615            2620                2625 cat gtc cat tac ctg atc caa gaa gcc aca gat gag aac ctt ctc    7929
His Val His Tyr Leu Ile Gln Glu Ala Thr Asp Glu Asn Leu Leu
    2630            2635                2640 agc cag atg tac ttg ggg tgg gct ccg tat atg tga                7965
Ser Gln Met Tyr Leu Gly Trp Ala Pro Tyr Met
    2645            2650

<210> SEQ ID NO 2
<211> LENGTH: 2654
<212> TYPE: PRT
<213> ORGANISM: Xenopus laevis

<400> SEQUENCE: 2

Met Ala Thr Asp Pro Gly Leu Glu Met Ala Ser Met Ile Pro Ala Leu
1               5                   10                  15

Arg Glu Leu Ala Ser Ala Gly Ala Glu Glu Tyr Asn Thr Thr Val Gln
            20                  25                  30

Lys Pro Arg Gln Ile Leu Cys Gln Phe Ile Asp Arg Ile Leu Thr Asp
        35                  40                  45

Val Asp Val Val Ala Val Glu Leu Ser Lys Asn Thr Asp Ser Gln Pro
    50                  55                  60

Ser Ser Val Met Leu Leu Asp Phe Ile Gln His Ile Met Lys Ser Thr
65                  70                  75                  80

Pro Leu Met Phe Leu Ser Ala Asn Asn Gly Asp Gln Ser Ala Glu Thr
                85                  90                  95

Asn Gln Asn Cys Val Ala Phe Ser Asn Trp Ile Ile Ser Arg Leu Leu
            100                 105                 110

Arg Ile Gly Ala Thr Pro Ser Cys Lys Ala Leu His Arg Lys Ile Ala
        115                 120                 125

Glu Val Ile Arg Ser Leu Leu Phe Leu Phe Lys Asn Lys Ser Ser Phe
    130                 135                 140

Leu Phe Gly Val Phe Thr Lys Asp Leu Leu His Leu Phe Glu Asp Leu
145                 150                 155                 160

Ile Tyr Ile His Glu Gln Asn Met Glu Lys Ser Val Val Trp Pro Val
                165                 170                 175

Thr Ile Ser Arg Phe Leu Ser Asn Ala Ser Glu Asn Gln Thr Cys Leu
            180                 185                 190

Arg Cys Thr Gln Phe Gln Leu Leu Asn Met Gln Asn Ile Glu Pro Leu
        195                 200                 205
```

```
Glu Ser Thr Leu Leu Met Val Leu Met Asp Asn Glu His Asp Ile Ser
        210                 215                 220

Pro Val Phe Phe Gln Arg Gln Asn Leu Leu Leu Trp Gly Ile Gly Cys
225                 230                 235                 240

Ser Leu Leu Asp Tyr Gly Ser Thr Ser Leu Lys Ile Gln Ala Leu His
                245                 250                 255

Phe Leu Arg Gln Leu Ile Lys Leu Gly Gly Pro Pro Glu Gln Gly Ala
            260                 265                 270

Tyr Phe Phe Ile Val Phe Phe Gly Ile Leu Thr Cys Ile Lys Asp
        275                 280                 285

Met Asp Leu Glu Glu Val Ser Leu Tyr Glu Met Pro Leu Leu Lys Leu
        290                 295                 300

Val Lys Val Leu Phe Pro Phe Glu Ser Lys Ser Tyr Leu Asn Ile Glu
305                 310                 315                 320

Pro Val Tyr Leu Asn Met Leu Leu Glu Lys Leu Ala Ala Leu Phe Asp
                325                 330                 335

Gly Gly Ile Leu Ser Asn Ile Gln Ser Ala Pro Leu Lys Glu Ala Leu
            340                 345                 350

Cys Tyr Met Val His Tyr Phe Leu Ser Ile Val Pro Pro Gly Tyr Glu
        355                 360                 365

Ser Ala Lys Glu Val Arg Glu Ala His Val Arg Cys Ile Cys Arg Ala
370                 375                 380

Phe Val Asp Val Leu Gly Leu Gln Ser Lys Gln Glu Tyr Leu Val Cys
385                 390                 395                 400

Pro Leu His Glu Ala Leu Arg Ile Glu Asn Leu Val Phe Met Gln Gln
                405                 410                 415

Gln Arg Met Gln Pro Leu Ser Thr Asp Ser Glu Gly Gly Gly Ser Ser
            420                 425                 430

Ser Ser Asp Glu Val Gln Glu Lys Arg Pro Arg Leu Ser Leu Thr Ala
        435                 440                 445

Lys Pro Leu Arg Arg Asn Thr Pro Ser Val Pro Ala Pro Val Asp Met
450                 455                 460

Lys Thr Lys Ser Ile Leu Trp Lys Ala Val Ala Lys Phe Ser Ser
465                 470                 475                 480

Ile Leu Cys Lys Leu Glu Gly Asp Glu Val Thr Asp Glu Glu Met Val
                485                 490                 495

Ser Leu Leu Glu Gly Leu Asn Thr Thr Val Arg Val Ala Ala Leu Asn
            500                 505                 510

Thr Val His Ile Phe Thr Asn Asp Ser Thr Asp Thr Asp Gln Leu Val
        515                 520                 525

Ser Asp Leu Ser Asn Thr Ser Gly Ile Gln Ser Val Glu Ile Val Pro
530                 535                 540

His Val Phe Trp Leu Ser Pro Glu Asp Ile Leu Lys Ile Leu Lys Ile
545                 550                 555                 560

Cys Arg Lys Val Leu Asp Ser Ala His Gln Arg Ala Asn Ile Asn Asp
                565                 570                 575

Ile Leu Met Lys Ile Ile Lys Ile Phe Asp Ala Ile Leu Tyr Ile His
            580                 585                 590

Ala Gly Asn Arg Leu Asn Asp Gln Thr Leu Lys Asp Leu Cys Ser Met
        595                 600                 605

Ile Ser Leu Pro Trp Leu Gln Asn His Ser Asn His Ala Ser Phe Lys
610                 615                 620

Val Ala Ser Phe Asp Pro Thr Leu Met Thr Ile Ser Glu Arg Ile Gly
```

-continued

```
                625                 630                 635                 640
Gln His Tyr Ser Pro Glu Ile Gln Ser Gln Leu Val Phe Leu Leu Cys
                    645                 650                 655

Leu Phe Pro Lys Met Leu Cys Pro Glu Trp Arg Leu Ala Val Tyr Gln
                660                 665                 670

Trp Ala Leu Asp Ser Pro His Glu Ile Val Arg Ala Arg Cys Ile Lys
            675                 680                 685

Gly Phe Pro Val Leu Leu Cys Asn Val Ser Gln Gln Gly Tyr Gly Pro
        690                 695                 700

Ile Pro Lys Ile Leu Ile Asp Cys Leu Asn Asp Ala Ser Glu Leu Val
705                 710                 715                 720

Lys Lys Glu Leu Ala Asn Ser Val Gly Met Phe Ala Ser Gly Leu Ala
                725                 730                 735

Cys Gly Phe Glu Leu Gln Tyr Ser Pro Thr Ala Pro Thr Ala Ala Glu
                740                 745                 750

Ser Glu Phe Leu Cys Ser Ser Leu Thr Val Thr Ala Leu Pro Ser Ser
                755                 760                 765

Lys Leu Ser Arg Met Thr Ala Ser Ala Leu Lys Pro Phe Leu Ala Leu
            770                 775                 780

Leu Asn Arg Asn Met Pro Ser Ser Val Lys Met Ala Phe Ile Glu Asn
785                 790                 795                 800

Met Pro Met Leu Phe Ala His Leu Ser Leu Glu Lys Asp Asp Leu Asp
                    805                 810                 815

Ser Arg Thr Val Ile Glu Ser Leu Leu Asn Leu Met Glu Asp Pro Asp
                820                 825                 830

Lys Asp Val Arg Thr Ala Phe Ser Gly Asn Ile Lys His Leu Leu Ala
            835                 840                 845

Cys Ala Asp Cys Glu Asp Gly Tyr Leu Lys Glu Ile Val Val Ser Arg
        850                 855                 860

Met Lys Lys Ala Tyr Thr Asp Ala Lys Met Ser Arg Asp Asn Glu Met
865                 870                 875                 880

Lys Asp Thr Leu Ile Leu Thr Thr Gly Asp Ile Gly Arg Ala Ala Lys
                    885                 890                 895

Gly Glu Leu Val Pro Phe Ala Leu Leu His Leu His Cys Leu Leu
                900                 905                 910

Ser Lys Ser Pro Cys Val Ala Gly Ala Ser Tyr Thr Glu Ile Arg Ser
            915                 920                 925

Leu Ala Ala Ala Lys Ser Thr Ser Leu His Ile Phe Phe Ser Gln Tyr
        930                 935                 940

Lys Lys Pro Ile Cys Gln Phe Leu Ile Glu Ser Leu His Ser Ser Gln
945                 950                 955                 960

Ala Ala Leu Leu Thr Asn Thr Pro Gly Arg Ser Ser Glu Met Gln Lys
                965                 970                 975

Gln Glu Ala Thr His His Arg Glu Ala Ala Leu Asp Ile Leu Ser Glu
            980                 985                 990

Ile Ala Asn Val Phe Asp Phe Pro  Asp Leu Asn Arg Phe  Leu Thr Arg
        995                 1000                 1005

Thr Leu  Gln Leu Leu Leu Pro  Tyr Leu Ala Ala Lys  Ala Ser Pro
    1010                 1015                 1020

Thr Ala  Ser Thr Leu Ile Arg  Thr Ile Ala Lys Gln  Leu Asn Val
    1025                 1030                 1035

Asn Arg  Arg Glu Ile Leu Ile  Asn Asn Phe Lys Tyr  Ile Phe Ser
    1040                 1045                 1050
```

-continued

```
His Leu Val Cys Ser Cys Thr Lys Asp Glu Leu Glu Lys Ser Leu
1055                1060                1065
His Tyr Leu Lys Asn Glu Thr Glu Ile Glu Leu Gly Ser Leu Leu
1070                1075                1080
Arg Gln Asp Tyr Gln Gly Leu His Asn Glu Leu Leu Leu Arg Leu
1085                1090                1095
Gly Glu His Tyr Gln Gln Val Phe Ser Gly Leu Ser Ile Leu Ala
1100                1105                1110
Thr Tyr Ala Ser Asn Asp Asp Pro Tyr Gln Gly Pro Arg Asn Phe
1115                1120                1125
Ala Lys Pro Glu Ile Met Ala Asp Tyr Leu Gln Pro Lys Leu Leu
1130                1135                1140
Gly Ile Leu Ala Phe Phe Asn Met His Leu Leu Ser Ser Ser Ile
1145                1150                1155
Gly Ile Glu Asp Lys Lys Met Ala Leu Asn Ser Leu Val Ser Leu
1160                1165                1170
Met Lys Leu Met Gly Pro Lys His Ile Ser Ser Val Arg Val Lys
1175                1180                1185
Met Met Thr Thr Leu Arg Thr Gly Leu Arg Tyr Lys Glu Glu Phe
1190                1195                1200
Pro Gly Leu Cys Cys Ser Ala Trp Asp Leu Phe Val Arg Cys Leu
1205                1210                1215
Asp Gln Ala Tyr Leu Gly Pro Leu Leu Ser His Val Ile Val Ala
1220                1225                1230
Leu Leu Pro Leu Leu His Ile Gln Pro Lys Glu Thr Val Ala Val
1235                1240                1245
Phe Arg Tyr Leu Ile Val Glu Asn Arg Asp Ala Val Gln Asp Phe
1250                1255                1260
Leu His Glu Ile Tyr Phe Leu Pro Asp His Pro Glu Leu Lys Glu
1265                1270                1275
Ile Gln Lys Val Leu Gln Glu Tyr Arg Lys Glu Thr Thr Lys Ser
1280                1285                1290
Thr Asp Leu Gln Thr Ala Met Gln Leu Ser Ile Arg Ala Ile Gln
1295                1300                1305
His Glu Asn Val Asp Val Arg Met His Ala Leu Thr Ser Leu Lys
1310                1315                1320
Glu Thr Leu Tyr Lys Asn Gln Ala Lys Leu Leu Gln Tyr Ser Thr
1325                1330                1335
Asp Ser Glu Thr Val Glu Pro Val Ile Ser Gln Leu Val Thr Val
1340                1345                1350
Leu Leu Ile Gly Cys Gln Asp Ala Asn Pro Gln Ala Arg Leu Phe
1355                1360                1365
Cys Gly Glu Cys Leu Gly Gln Leu Gly Ala Ile Asp Pro Gly Arg
1370                1375                1380
Leu Asp Phe Ser Pro Ser Glu Thr Gln Gly Lys Gly Phe Thr Phe
1385                1390                1395
Val Ser Gly Val Glu Asp Ser Asp Phe Ala Tyr Glu Leu Leu Thr
1400                1405                1410
Glu Gln Thr Arg Ala Phe Leu Ala Tyr Ala Asp Asn Val Arg Ala
1415                1420                1425
Gln Asp Ser Ala Ala Tyr Ala Ile Gln Glu Leu Leu Ser Ile Phe
1430                1435                1440
```

```
Glu Cys Lys Glu Gly Arg Thr Asp Cys Pro Gly Arg Arg Leu Trp
1445                1450                1455

Arg Arg Phe Pro Glu His Val Gln Glu Ile Leu Glu Pro His Leu
    1460            1465                1470

Asn Thr Arg Tyr Lys Ser Ser Arg Lys Ala Val Asn Trp Ser Arg
1475                1480                1485

Val Lys Lys Pro Ile Tyr Leu Ser Lys Leu Gly Asn Asn Phe Ala
1490                1495                1500

Asp Trp Ser Ala Thr Trp Ala Gly Tyr Leu Ile Thr Lys Val Arg
1505                1510                1515

His Glu Leu Ala Arg Arg Val Phe Ser Cys Cys Ser Ile Met Met
1520                1525                1530

Lys His Asp Phe Lys Val Thr Ile Tyr Leu Leu Pro His Ile Leu
1535                1540                1545

Val Tyr Val Leu Leu Gly Cys Asn Lys Glu Asp Gln Gln Glu Val
1550                1555                1560

Tyr Ala Glu Ile Met Ala Val Leu Lys His Glu Asp Pro Leu Met
1565                1570                1575

Arg Arg Leu Gln Asp Ser Ala Ser Asp Leu Ser Gln Leu Ser Thr
1580                1585                1590

Gln Thr Val Phe Ser Met Leu Asp His Leu Thr Gln Trp Ala Arg
1595                1600                1605

Glu Lys Phe Gln Ala Leu Asn Ala Glu Lys Thr Asn Pro Lys Pro
1610                1615                1620

Gly Thr Arg Gly Glu Pro Lys Ala Val Ser Asn Glu Asp Tyr Gly
1625                1630                1635

Glu Tyr Gln Asn Val Thr Arg Phe Leu Asp Leu Ile Pro Gln Asp
1640                1645                1650

Thr Leu Ala Val Ala Ser Phe Arg Ser Lys Ala Tyr Thr Arg Ala
1655                1660                1665

Leu Met His Phe Glu Ser Phe Ile Met Glu Lys Lys Gln Glu Ile
1670                1675                1680

Gln Glu His Leu Gly Phe Leu Gln Lys Leu Tyr Ala Ala Met His
1685                1690                1695

Glu Pro Asp Gly Val Ala Gly Val Ser Ala Ile Arg Lys Lys Glu
1700                1705                1710

Ala Ser Leu Lys Glu Gln Ile Leu Glu His Glu Ser Ile Gly Leu
1715                1720                1725

Leu Arg Asp Ala Thr Ala Cys Tyr Asp Arg Ala Ile Gln Leu Lys
1730                1735                1740

Pro Glu Glu Ile Ile His Tyr His Gly Val Val Lys Ser Met Leu
1745                1750                1755

Gly Leu Gly Gln Leu Ser Thr Val Ile Thr Gln Val Asn Gly Ile
1760                1765                1770

Leu Asn Ser Arg Ser Glu Trp Thr Ala Glu Leu Asn Thr Tyr Arg
1775                1780                1785

Val Glu Ala Ala Trp Lys Leu Ser Gln Trp Asp Leu Val Glu Glu
1790                1795                1800

Tyr Leu Ser Ala Asp Arg Lys Ser Thr Thr Trp Ser Ile Arg Leu
1805                1810                1815

Gly Gln Leu Leu Leu Ser Ala Lys Lys Gly Glu Arg Asp Met Phe
1820                1825                1830

Tyr Glu Thr Leu Lys Val Val Arg Ala Glu Gln Ile Val Pro Leu
```

```
            1835                1840                1845

Ser Ala Ala Ser Phe Glu Arg Gly Ser Tyr Gln Arg Gly Tyr Glu
    1850                1855                1860

Tyr Ile Val Arg Leu His Met Leu Cys Glu Leu Glu His Ser Val
    1865                1870                1875

Lys Met Phe Leu Gln Lys Pro Ser Val Glu Pro Ala Val Asp Ser
    1880                1885                1890

Leu Asn Leu Pro Ala Arg Leu Glu Met Thr Gln Asn Ser Tyr Arg
    1895                1900                1905

Ala Arg Glu Pro Ile Leu Ala Val Arg Arg Ala Leu Gln Thr Ile
    1910                1915                1920

Asn Lys Arg Pro Asn His Ala Asp Met Ile Gly Glu Cys Trp Leu
    1925                1930                1935

Gln Ser Ala Arg Val Ala Arg Lys Ala Gly His His Gln Thr Ala
    1940                1945                1950

Tyr Asn Ala Leu Leu Asn Ala Gly Glu Ser Arg Leu Ser Glu Leu
    1955                1960                1965

Asn Val Glu Arg Ala Lys Trp Leu Trp Ser Lys Gly Asp Val His
    1970                1975                1980

Gln Ala Leu Ile Val Leu Gln Lys Gly Ala Glu Leu Phe Leu Ser
    1985                1990                1995

Ser Thr Ser Ala Pro Pro Glu Gln Gln Leu Ile His Gly Arg Ala
    2000                2005                2010

Met Leu Leu Val Gly Arg Leu Met Glu Glu Thr Ala Asn Phe Glu
    2015                2020                2025

Ser Asn Ala Val Met Lys Lys Tyr Lys Asp Val Thr Ala Leu Leu
    2030                2035                2040

Pro Glu Trp Glu Asp Gly His Phe Tyr Leu Ala Lys Tyr Tyr Asp
    2045                2050                2055

Lys Leu Met Pro Met Val Thr Asp Asn Lys Met Glu Lys Gln Gly
    2060                2065                2070

Asp Leu Ile Arg Tyr Ile Val Leu Pro Phe Gly Arg Ser Leu Gln
    2075                2080                2085

Phe Gly Asn Gln Tyr Ile Tyr Gln Ser Met Pro Arg Met Leu Ser
    2090                2095                2100

Leu Trp Leu Asp Phe Gly Ala Lys Val Tyr Glu Trp Glu Lys Ala
    2105                2110                2115

Gly Arg Ala Asp Arg Leu Gln Met Lys Asn Glu Leu Met Lys Ile
    2120                2125                2130

Asn Lys Val Ile Ser Asp His Lys Asn Gln Leu Ala Pro Tyr Gln
    2135                2140                2145

Phe Leu Thr Ala Phe Ser Gln Leu Ile Ser Arg Ile Cys His Ser
    2150                2155                2160

His Asp Glu Val Phe Ala Val Leu Met Glu Ile Val Ala Lys Val
    2165                2170                2175

Phe Val Ala Tyr Pro Gln Gln Ala Met Trp Met Met Thr Ala Val
    2180                2185                2190

Ser Lys Ser Ser Tyr Pro Met Arg Val Asn Arg Cys Lys Glu Ile
    2195                2200                2205

Leu Glu Lys Ala Ile His Met Lys Pro Ser Leu Gly Lys Phe Ile
    2210                2215                2220

Gly Asp Ala Thr Arg Leu Thr Asp Lys Leu Leu Glu Leu Cys Asn
    2225                2230                2235
```

-continued

```
Lys Pro Val Asp Gly Asn Thr Ser Thr Leu Ser Met Asn Ile His
    2240                2245                2250

Phe Lys Met Leu Lys Lys Leu Val Glu Glu Thr Thr Phe Ser Glu
    2255                2260                2265

Ile Leu Ile Pro Leu Gln Ser Val Met Ile Pro Thr Leu Pro Ser
    2270                2275                2280

Thr Ala Gly Lys Arg Asp His Ala Asp His Asp Pro Phe Pro Gly
    2285                2290                2295

His Trp Ala Tyr Leu Ser Gly Phe Asp Asp Ala Val Glu Ile Leu
    2300                2305                2310

Pro Ser Leu Gln Lys Pro Lys Lys Ile Ser Leu Lys Gly Ser Asp
    2315                2320                2325

Gly Lys Ser Tyr Ile Met Met Cys Lys Pro Lys Asp Asp Leu Arg
    2330                2335                2340

Lys Asp Cys Arg Leu Met Glu Phe Asn Ser Leu Ile Asn Lys Cys
    2345                2350                2355

Leu Arg Lys Gly Ala Glu Ser Arg Arg Arg Glu Leu His Ile Arg
    2360                2365                2370

Thr Tyr Ala Val Ile Pro Leu Asn Asp Glu Cys Gly Ile Ile Glu
    2375                2380                2385

Trp Val Asn Asn Thr Ala Gly Phe Arg Asn Ile Leu Ile Lys Leu
    2390                2395                2400

Tyr Lys Glu Lys Gly Ile Tyr Met Gly Gly Lys Glu Leu Arg Gln
    2405                2410                2415

Cys Met Leu Pro Lys Ser Ala Pro Leu Gln Glu Lys Leu Lys Val
    2420                2425                2430

Phe Lys Glu Ala Leu Leu Pro Arg His Pro Pro Leu Phe His Glu
    2435                2440                2445

Trp Phe Leu Arg Thr Phe Pro Asp Pro Thr Ser Trp Tyr Asn Ser
    2450                2455                2460

Arg Ser Ala Tyr Cys Arg Ser Thr Ala Val Met Ser Met Val Gly
    2465                2470                2475

Tyr Ile Leu Gly Leu Gly Asp Arg His Gly Glu Asn Ile Leu Phe
    2480                2485                2490

Asp Ser Leu Thr Gly Glu Cys Val His Val Asp Phe Asn Cys Leu
    2495                2500                2505

Phe Asn Lys Gly Glu Thr Phe Glu Val Pro Glu Ile Val Pro Phe
    2510                2515                2520

Arg Leu Thr His Asn Met Val Asn Gly Met Gly Pro Met Gly Thr
    2525                2530                2535

Glu Gly Leu Phe Arg Arg Ala Cys Glu Val Ile Met Arg Leu Met
    2540                2545                2550

Arg Glu Gln Arg Glu Ser Leu Met Ser Val Leu Lys Pro Phe Leu
    2555                2560                2565

His Asp Pro Leu Val Glu Trp Ser Lys Pro Ala Arg Gly Ser Ser
    2570                2575                2580

Lys Gly Gln Val Asn Glu Thr Gly Glu Val Met Asn Glu Lys Ala
    2585                2590                2595

Lys Thr His Val Leu Asp Ile Glu Gln Arg Leu Gln Gly Val Ile
    2600                2605                2610

Lys Thr Arg Asn Arg Val Lys Gly Leu Pro Leu Ser Ile Glu Gly
    2615                2620                2625
```

| His | Val | His | Tyr | Leu | Ile | Gln | Glu | Ala | Thr | Asp | Glu | Asn | Leu | Leu |
|  | 2630 |  |  |  | 2635 |  |  |  |  | 2640 |  |  |  |  |

| Ser | Gln | Met | Tyr | Leu | Gly | Trp | Ala | Pro | Tyr | Met |
|  | 2645 |  |  |  |  | 2650 |  |  |  |  |

<210> SEQ ID NO 3
<211> LENGTH: 8443
<212> TYPE: DNA
<213> ORGANISM: Xenopus laevis

<400> SEQUENCE: 3

```
cactggcctg aaagcgacac ccggaaatgt cagtagtcgc ttgaagcgca taacaaagca      60
gcacgtcacg tctgaggaag tgcaaacgag tattttggac agcgaggcca ccataccgtg     120
cttttctcc cgcctttgtt acgcaaattc agattctgta ggttttctgg gggttctagc     180
tctgggactg agctgctacc atggctactg accccggtct tgaaatggcc tctatgatcc     240
cggccttgcg tgaacttgcc agtgccgggg cagaggaata taacacaact gttcagaaac     300
caagacaaat cctttgccag tttatagacc ggattctgac agatgtggac gttgttgctg     360
tggagctttc aaagaatact gattctcagc caagttctgt gatgttgctg gatttttattc    420
aacacattat gaaatctacc ccattaatgt ttctcagtgc aaataacggt gatcagtctg     480
ctgaaaccaa tcagaactgt gttgcattta gcaactggat catttcccgg ctcttacgca     540
ttggggctac gccaagctgc aaagctttgc atagaaaaat cgctgaagtc atccgctccc     600
tgcttttct tttcaaaaac aagagttcct ttctatttgg tgtttttact aaagatttat      660
tacatctctt tgaagatctt atctacatac atgaacaaaa catggagaaa tccgtagttt     720
ggcctgtgac catttctaga ttttttaagca atgcatcaga aaaccaaact tgcttaagat     780
gcactcaatt tcagttgttg aacatgcaga acattgagcc tttagaatcc actctgctaa     840
tggttttgat ggataacgaa catgatattt ctccagtgtt tttccaaagg cagaaccctcc    900
tcctctgggg cattgggtgc tccctcttgg actatggaag tacatcactg aagatacagg     960
cattgcattt tttaagacaa ctaataaaat taggtggtcc accagaacag ggtgcatatt    1020
ttttcttcat tgtgtttttt gggatactaa cttgtataaa agacatggat ttagaagaag    1080
tgtctcttta tgagatgcca ctgttgaaat tggtaaaggt tttgttccca tttgaatcaa    1140
aatcttacct aaacattgaa cctgtctatc tgaatatgtt gctggagaaa cttgctgctc    1200
tctttgatgg aggtatcttg agtaatattc agtcagctcc cttgaaagaa gctctttgct    1260
atatggtcca ttacttcctt agcattgtgc ctccgggcta tgaatctgcc aaagaagtcc    1320
gagaggcaca tgttcgctgc atctgtagag cttttgttga tgtccttgga cttcagagca    1380
agcaagaata cttggtctgc ccccttcatg aagcattaag aatagaaaac ctggtgttca    1440
tgcagcagca gcgcatgcag cccctaagca cagactcaga gggtggtggg agcagcagca    1500
gcgatgaagt gcaagagaaa cgaccacgtt tgagtctaac tgcaaagcct ctaagaagaa    1560
acacaccatc agtgcctgct cctgtggata tgaagacaaa gagcatacta tggaaagcag    1620
tgagtgcgaa attctcctct attttgtgca aactggaagg tgacgaagtt acagatgaag    1680
agatggtttc tttattggag ggtcttaata caactgtacg tgttgctgct ctcaatacag    1740
ttcatatctt cactaatgat ccacagata ctgatcagtt agtatctgac ttgagcaata    1800
cttctggcat tcagtcggta gaaatagtac ctcacgtttt ctggctcagt ccagaggata    1860
ttctaaaaat acttaaaatt tgtagaaagg ttccttgattc tgcacaccag agagccaata    1920
taaatgacat tctgatgaag ataataaaaa tatttgatgc aatactctac attcatgcag    1980
```

```
gaaacagatt aaatgaccaa actcttaagg atttgtgcag catgatctca ttaccctggc    2040
ttcagaatca ttcaaatcat gcttccttta aagtggcatc atttgaccca acattgatga    2100
ccataagtga gcggattggc caacattact cacctgaaat tcagtctcaa cttgttttcc    2160
tcctgtgcct gtttccaaaa atgttatgcc ctgagtggag attagctgtg taccaatggg    2220
cattggatag cccacatgag attgttcgtg cccgttgcat caaaggattc cctgttcttc    2280
tgtgcaatgt tagccagcag gggtatggtc caattcccaa gattttaatc gactgtttga    2340
atgatgcctc tgagctggtg aagaaggagt tagccaactc agtgggtatg tttgcctccg    2400
gccttgcttg cggttttgag ctgcaatatt ccccaacggc acctactgca gcagaatctg    2460
agttcctttg tagcagcctg acagttactg ctttaccctc atcgaaactt tctcgtatga    2520
ccgcctctgc attaaaacca ttcctggcac tgcttaatcg aaacatgcca agctccgtca    2580
aaatggcatt tattgaaaat atgcccatgc tgtttgctca cctctctctt gagaaagatg    2640
atttggattc ccgaactgtg attgaatcat tgttaaacct aatggaggac ccagacaagg    2700
atgtaaggac agctttcagt gggaacatca aacacctgtt ggcgtgtgca gactgtgagg    2760
acggatatct aaaggagatt gtagtctcaa ggatgaaaaa agcatataca gatgccaaga    2820
tgtcgcgtga caatgagatg aaggacactc tcattcttac aactggggat ataggaaggg    2880
cagcaaaagg agagttggta ccatttgcac tgttgcatct gctgcattgc ctgctgtcta    2940
aatccccatg tgtggcaggt gcttcttaca cagaaatccg atctcttgca gcagcaaagt    3000
ccaccagtct gcatatcttt tttagccagt acaagaaacc gatttgtcag ttccttatag    3060
aatcgcttca ctcaagccag gcagcccttc tgaccaacac acctggccgc agcagtgaaa    3120
tgcagaagca ggaggcaaca catcataggg aagctgcact tgacatctta tccgaaatag    3180
caaatgtatt tgatttccca gacttaaacc gcttttttaac gaggactttg caacttttgc    3240
ttccatatct tgctgccaaa gctagtccaa cagcctctac tctgataaga acgattgcca    3300
aacaacttaa tgtgaatcga agggagatcc tgatcaataa cttcaagtat atattctctc    3360
acttggtttg ttccttgcaca aaagatgagc tggaaaagtc gcttcattac ctaaagaatg    3420
aaacagaaat tgagctgggt agtttactga gacaggacta ccagggactg cacaatgaac    3480 tactttttgcg cctgggtgag cactatcagc aggtctttag tgggctgtcc atattagcaa    3540
catatgcatc caacgatgat ccatatcagg gacctaggaa ttttgcaaag ccagaaataa    3600
tggcagatta tttgcaacca aagctttttag gaattttggc tttctttaat atgcacctgt    3660
tgagctccag cattggcatt gaagacaaga aaatggcctt gaacagtctg gtttctttaa    3720
tgaaactgat gggaccaaag catataagtt ccgttagggt caagatgatg acgaccttga    3780
gaactggcct acgttataaa gaggaatttc cggggctttg ctgcagtgca tgggacttgt    3840
ttgttcgctg cctggatcaa gcctatctgg gcccgctcct cagtcatgtg attgttgcac    3900
tgttgcctct gttgcacatc cagcctaaag aaactgttgc tgtgttccgc tatctcatag    3960
tagagaacag ggatgctgtt caggatttcc ttcatgaaat atattttctg cctgatcatc    4020
cagaattgaa agaaatccag aaggttctac aagaatacag gaaagaaacc accaaaagca    4080
cagatctgca gacagccatg cagctgtcta ttcgagccat tcagcatgaa aatgtggatg    4140
ttcgcatgca tgcccttact agtctgaaag aaacactcta caagaaccag gctaaactgt    4200
tgcagtattc aacagacagt gaaactgtag aaccagttat ctcccagctg gtaacagttc    4260
tcttaattgg atgccaagat gccaatccac aagcccgtct attttgtggt gaatgccttg    4320
```

```
gccaacttgg agccattgat cctgggagat tggatttctc acccagtgaa acacaaggga   4380
aaggttttac ttttgtttca ggagttgaag attcagactt tgcctatgag ttgctcacag   4440
agcaaactag agcatttctt gcctatgctg ataatgtccg cgcccaggac tctgctgcct   4500
atgctataca ggagcttctc tctatcttcg agtgcaaaga aggaaggact gattgtcctg   4560
ggcgtaggct gtggaggaga ttcccagaac atgttcaaga aatattggag ccacatctta   4620
atactagata caagagttcc agaaaggctg taaactggtc cagagtgaaa aagcccattt   4680
atttgagcaa gttaggaaat aactttgcag actggtcagc aacatgggca ggttacctca   4740
taactaaggt tcgacatgag cttgccagga gagttttcag ctgttgtagt ataatgatga   4800
agcatgactt caaagtgacc atttatctgc tcccacatat tttggtctat gttttgttgg   4860
gatgtaacaa agaagatcag caagaggtat atgcagaaat tatggcagtg ttaaagcatg   4920
aagatccact aatgcgtcgg ttacaggaca gcgcctcaga tctgagtcag ctcagcaccc   4980
aaacagtctt ttcaatgctt gatcatctta ctcagtgggc acgggagaaa ttccaggcac   5040
taaatgctga gaaacaaat cccaaccag gaaccagagg ggaaccaaag gcagtgtcta   5100
atgaagacta tggagagtat cagaatgtaa caaggttttt agatcttata ccgcaggata   5160 cttggctgt tgcttccttt cgttccaaag cttatactag agctctcatg cattttgaat   5220
cctttataat ggaaaagaaa caagaaattc aggagcacct tggatttctt cagaaactgt   5280
atgctgctat gcatgagcca gatggagtag ctggggtaag cgccattcgc aagaaagaag   5340
cttctctgaa agaacagatc ttggagcatg aaagtattgg tctgttgaga gatgccactg   5400
cttgctatga tagagctatt cagctaaagc ctgaggagat aattcactat catggggtag   5460
tgaaatctat gcttggtctt ggccagttgt ctactgtaat tacgcaagtt aacggaattt   5520
tgaatagcag gtcggaatgg acagctgaac taaacacata cagagtagaa gcagcatgga   5580
aactctcaca gtgggattta gtggaggaat acttatctgc agacagaaaa tctaccacat   5640
ggagcattag gctgggcaa tcctgctttt cagctaaaaa gggggagaga gatatgtttt   5700
atgaaacgct caaagtagtc cgagccgaac aaattgttcc actgtctgct gccagctttg   5760 agagggctc ctaccaacga ggatatgagt acatagtaag gttgcacatg ttatgtgagt   5820
tggagcacag tgtaaaaatg tttcttcaga aaccttctgt tgagcctgca gtagactctt   5880
taaacttgcc agcacggcta gaaatgacac agaattccta cagagcaaga gagcccattt   5940
tggcagttcg cagggcacta caaacaatca acaaaaggcc taatcatgca gatatgattg   6000
gtgagtgttg gctgcaaagt gctcgagttg cgcgtaaggc tgggcatcac cagactgctt   6060
acaatgctct gcttaatgct ggggagtcca gattgtctga gctcaatgtt gaacgggcga   6120
agtggctctg gtccaagggt gatgtacatc aagctctcat tgttctccag aagggagcag   6180
aactgttcct gtcaagtacc agcgctccac cagaacagca gcttatccat ggcagagcca   6240
tgctgctggt gggccgtttg atggaagaga ctgccaactt tgaaagcaac gctgtgatga   6300
agaaatataa agatgtaaca gcactgttgc ctgaatggga agatggccat ttttatcttg   6360
ccaagtacta tgacaaactc atgccaatgg ttactgataa caagatggag aagcaaggag   6420
acttgatacg atatatagta cttcccttg gaaggtcttt acagttcgga aaccaatata   6480
tttatcaatc gatgccacgt atgctttcac ttttggctgga ttttggagct aaagtttatg   6540
aatgggaaaa agctggtcgt gctgacagat tacaaatgaa aaatgaattg atgaaaataa   6600
ataaggtcat atctgaccat aaaaaccagc ttgctcctta tcagttcctt acagcttttct   6660 cacagctaat ctccagaata tgtcactctc atgatgaggt gtttgctgtg ttgatggaaa   6720
```

-continued

```
ttgtggctaa ggtgtttgtg gcatacccccc agcaggcaat gtggatgatg actgctgtgt      6780
ctaagtcatc atatccaatg cgtgtaaaca gatgcaaaga gatactcgag aaggccatac      6840
atatgaagcc atccctagga aaatttattg gagatgcaac tcgcctcact gataaactac      6900
tagagctctg caataagccg gtggatggaa atactagcac cctcagtatg aatatccact      6960
tcaaaatgct gaagaaacta gtagaagaaa caacatttag tgaaatcctt attcctctac      7020
agtccgtgat gattcccacc ctaccgtcta ctgcagggaa gcgtgaccat gctgatcatg      7080
atccattccc tggccactgg gcttacctct caggctttga tgacgcggta gagattctgc      7140
cttctctcca gaaaccaaag aaaatttctc taaagggatc agacggtaaa tcatacatta      7200
tgatgtgtaa accaaaagat gatcttagaa aggactgccg gctgatggaa tttaactctt      7260
taatcaacaa gtgtttacgc aaaggtgcag aatcacgaag gagagagctt catattcgaa      7320
cctatgctgt cattccactg aatgacgaat gcggcatcat agagtgggtg aataatactg      7380
caggattccg gaacatattg atcaagctgt acaaggaaaa aggcatttac atgggtggaa      7440
aggaattgcg gcagtgtatg cttcccaaga gcgcaccact acaagaaaag ctgaaagtct      7500
ttaaggaggc cctactgcct cgtcaccccc cattgttcca tgaatggttt ttaagaacat      7560
ttcctgatcc tacttcttgg tataacagca gatcagccta ttgccgttcc actgctgtga      7620
tgtctatggt aggttacata ctgggcctag gggaccgcca tggagaaaac attctttttg      7680
actcgcttac tggggaatgt gtccatgtgg attttaactg cctcttcaac aagggtgaaa      7740
catttgaagt tccagagatt gtccccttcc gactaacaca taacatggtc aatggtatgg      7800
gccccatggg gacggaggga cttttttcgac gtgcatgtga ggtcatcatg aggttaatga      7860
gagaacagag ggagtcactt atgagtgtgc tgaaacccttt tttacatgat cctttggtgg      7920
aatggagtaa accagcaaga gggagtagta aaggtcaagt caacgagaca ggagaagtga      7980
tgaatgaaaa ggccaaaaca catgtgcttt acatagagca gaggctacaa ggtgtgatta      8040
agaccaggaa tcgtgtaaag ggacttccgc tgtccattga aggacatgtc cattacctga      8100
tccaagaagc cacagatgag aaccttctca gccagatgta cttggggtgg gctccgtata      8160
tgtgatgctg ctcatgtgga acatctccca ttctgtcaga gaataagtac atttgtaaat      8220
aactgtaggt gtatatttgt atgaatacat ttattataca attgcaggac aaaaaaatgt      8280
ccaataggta gttttatttt gatggaggag tcatgcatct gtttatataa aacattttgt      8340
atactatttt ttattaccac catttatgta gccattaatt ggtttggaat acttttttga      8400
aaaataaata ttgttatttc ttgtaaaaaa aaaaaaaaa aaa                          8443
```

<210> SEQ ID NO 4
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(24)
<223> OTHER INFORMATION: n=i

<400> SEQUENCE: 4
ccggaattga ygcnmgnytn atgg                                              24

<210> SEQ ID NO 5
<211> LENGTH: 24
<212> TYPE: DNA

```
-continued

<213> ORGANISM: Artificial Sequence
<220> FEATURE:
<223> OTHER INFORMATION: primer
<220> FEATURE:
<221> NAME/KEY: misc_feature
<222> LOCATION: (1)..(24)
<223> OTHER INFORMATION: n=i

<400> SEQUENCE: 5
cgcggatccn ccrcaytcnt crtt                                           24
```

CLONING AND FUNCTIONAL ASSAYS OF XENOPUS ATR

RELATED APPLICATIONS

This application claims priority to U.S. provisional application 60/314,215, filed Aug. 22, 2001, the disclosure of which is hereby incorporated by reference in its entirety.

GOVERNMENT SUPPORT

Work described herein was funded, in whole or in part, by National Institutes of Health Grant GM43974.

BACKGROUND OF THE INVENTION

Control of the cell cycle is fundamental to the growth and maintenance of eukaryotic organisms, from yeasts to mammals. Cells have evolved critical mechanisms to help protect the fidelity of DNA synthesis. One important mechanism is commonly referred to as "cell-cycle checkpoint control". Cell cycle checkpoints insure that individual steps of the cell cycle are completed before the next step occurs. In response to DNA damage or a block to DNA replication, progression through the cell cycle is delayed. This allows time for the cell to repair the DNA prior to continuing through the cell cycle, thus improving genomic stability and the fidelity of DNA synthesis (Elledge (1996) Science 274: 1664–1672; O'Connell et al. (2000) Trends Cell Biol 10: 296–303).

The ability to coordinate cell cycle transitions in response to genotoxic and other stressors is critical to the maintenance of genetic stability and the prevention of uncontrolled cellular growth. Loss of a checkpoint gene leads to genetic instability and the inability of cells to deal with genomic insults such as those suffered as a result of the daily exposure to ultraviolet radiation. The loss of negative growth control and improper monitoring of the fidelity of DNA replication are common features of tumor cells. When checkpoints are eliminated (e.g., by mutation or other means), cell death, infidelity in chromosome transmission, and/or increased susceptibility to deleterious environmental factors (e.g., DNA-damaging agents) result.

Many components of the checkpoint pathways that respond to DNA damage have been identified in various species from yeast to vertebrates (Elledge (1996) Science 274: 1664–1672). The response is believed to involve sensor proteins which respond to DNA damage and/or replication stress. The sensor proteins transmit a signal (via transducer proteins) which induces one or more effects in a cell. Such effects allow the cell to appropriately cope with the DNA damage by, for example, inducing a cell cycle delay to allow time for the DNA damage to be repaired. Other possible responses of a cell to DNA damage include cell death, for example, if the DNA damage is too great to be repaired (recently reviewed in Zhou and Elledge (2000) Nature 408: 433–439).

One class of sensor proteins include Rad3/ATR proteins (Bentley et al. (1996) EMBO Journal 15: 6641–6651; O'Connell et al. (2000) Trends Cell Biol 10: 296–303; Cimprich et al. (1996) PNAS 93: 2850–2855; Keegan et al. (1996) Genes & Development 10: 2423–2437). This family of sensor proteins actually is part of a larger family of phosphoinositide kinase (PIK)-related protein kinases. This family of PIK-kinases are characterized by a C-terminal kinase domain and include ATM/Tell (Lavin and Shiloh (1997) Annu. Rev Immunology 15: 177–202; Sanchez et al. (1996) Science 271: 357–360) and DNA-PKcs (Smith and Jackson (1999) Genes & Development 13: 916–934).

Following detection of DNA damage or a replication block, a signal is transduced to effector proteins. These include Chk1 and Cds1 (Elledge (1996) Science 274: 1664–1672). However, the molecular nature of how this signal is transduced is not well understood. Based on previous work, it appears that various sensors induce cell cycle delay in response to different types of DNA damage, and that different sensors signal through different effector proteins. Additionally, extensive variability has been observed in the results obtained across species. Thus, although it appears that the general machinery for checkpoint control in response to DNA damage is evolutionarily conserved, it has remained uncertain as to whether the specific molecular mechanisms employed to accomplish these goals are also conserved.

Given the importance of proper checkpoint control in maintaining genomic stability and insuring the fidelity of DNA replication, a better understanding of the molecular mechanisms underlying this process has tremendous value. Specifically, such an understanding allows for the development of rational screens for agents which can modulate checkpoint control in response to DNA damage. Such agents provide novel therapies for various proliferative disorders including all forms of cancer.

The present invention aims to address the shortcomings of the prior art. We describe the isolation and characterization of Xenopus ATR nucleic acids and proteins. The characterization of Xenopus ATR revealed insights into a specific mechanism whereby DNA damage is sensed and then transduced to induce a cell cycle delay. The present invention demonstrates that ATR phosphorylates Chk1 (e.g., Chk1 is a substrate for the ATR kinase), and that this phosphorylation is an evolutionarily conserved mechanism necessary for the cell cycle delay induced by DNA damage or a DNA replication block.

The teachings of the present invention allow, for the first time, methods of screening for agents which modulate the activity of an ATR protein in any species. Such screens will not only increase understanding of cell cycle checkpoints, but will also provide possible therapeutic agents for the treatment of proliferative disorders.

SUMMARY OF THE INVENTION

The ability of cells to regulate progression through the cell cycle in response to DNA damage and DNA replication blocks is critical in insuring proper genomic stability and for maintaining appropriate cell proliferation. In order to accomplish this task, cells must be able to accurately sense when DNA damage has occurred, and then transduce notice of this DNA damage to the cell cycle machinery. This process results in a cell cycle delay that provides the cell with the opportunity to repair DNA damage, and it is this cell cycle delay in response to DNA damage that helps insure genomic stability.

The complex molecular system involved in the sensing and transduction of DNA damage to induce appropriate cell cycle delays is a critical aspect of normal embryonic and adult development. Accordingly, a goal of the present invention is to increase our understanding of the molecular nature of the process by which a cell responds to DNA damage by inducing a cell cycle delay. The present invention demonstrates the identification of an ATR polypeptide, isolated from Xenopus laevis. Furthermore, the present invention demonstrates several specific functions for not only Xenopus ATR, but also for ATR polypeptides in general. Most notably, the present invention demonstrates for the first time that Chk1 proteins are a direct target for ATR polypeptides (e.g., that Chk1 is phosphorylated by ATR). Based on these and other specific functions for ATR polypeptides, the present invention provides methods of screening for agents which modulate one or more of the specific activities of ATR polypeptides. Agents identified by the subject methods have substantial utility as therapeutics for proliferative disorders including all forms of cancer.

In a first aspect, the present invention provides an isolated nucleic acid encoding an ATR polypeptide. Exemplary ATR polypeptides comprise an amino acid sequence at least 80% identical to SEQ ID NO: 2, or a fragment of at least 50, 75, 100, 150, 200, 250 or 300 contiguous amino acids of SEQ ID NO: 2. Exemplary ATR polypeptides comprising an amino acid sequence at least 80% identical to either SEQ ID NO: 2, or a fragment of at least 50 amino acids of SEQ ID NO: 2, possess one or more of the following characteristics: (i) the ability to phosphorylate Chk1 proteins; (ii) the ability to bind to single-stranded DNA; (iii) the ability to bind to double-stranded DNA; (iv) the ability to induce cell cycle delay in response to UV damaged DNA; and/or (v) the ability to induce cell cycle delay in response to a DNA replication block.

In one embodiment, the isolated nucleic acid encodes a polypeptide comprising an amino acid sequence at least 90%, 95%, 98%, or even 99% identical to SEQ ID NO: 2, or a fragment of at least 50, 75, 100, 150, 200, 250 or 300 contiguous amino acids of SEQ ID NO: 2. Exemplary polypeptides, or fragments thereof, possess one or more of the following characteristics: (i) the ability to phosphorylate Chk1 proteins; (ii) the ability to bind to single-stranded DNA; (iii) the ability to bind to double-stranded DNA; (iv) the ability to induce cell cycle delay in response to UV damaged DNA; and/or (v) the ability to induce cell cycle delay in response to a DNA replication block.

In another embodiment, the isolated nucleic acid hybridizes under stringent conditions, including a wash step of 0.2×SSC at 65° C., to at least one nucleic acid sequence selected from SEQ ID NO: 1 or SEQ ID NO: 3. Exemplary nucleic acids encode polypeptides which possess one or more of the following characteristics: (i) the ability to phosphorylate Chk1 proteins; (ii) the ability to bind to single-stranded DNA; (iii) the ability to bind to double-stranded DNA; (iv) the ability to induce cell cycle delay in response to UV damaged DNA; and/or (v) the ability to induce cell cycle delay in response to a DNA replication block.

In still another embodiment, the isolated nucleic acid encodes an ATR polypeptide comprising an amino acid sequence identical to SEQ ID NO: 2, or a fragment of at least 50, 75, 100, 150, 200, 250 or 300 contiguous amino acids of SEQ ID NO: 2.

In yet another embodiment, the nucleic acid encodes a non-mammalian ATR polypeptide. In another embodiment, the nucleic acid encodes an amphibian or fish ATR polypeptide. Exemplary fish include, but are not limited to, zebrafish. In still another embodiment, the non-mammalian amphibian is a frog, toad, or newt. Exemplary amphibian species include, but are not limited to, *Xenopus laevis, Xenopus tropicalis, Rana pipiens, Rana catesbeiana, Rana temporaria, Rana sylvatica*, and *Bufo bufo*. In still another embodiment, the nucleic acid encodes a *Xenopus laevis* or *Xenopus tropicalis* ATR polypeptide.

In another embodiment, the nucleic acid encodes a polypeptide comprising an amino acid sequence at least 80%, 85%, 90%, 95%, 98%, or 100% identical to residues 2208–2654 of SEQ ID NO: 2 or residues 2351–2654 of SEQ ID NO: 2.

In a second aspect, the present invention provides an isolated nucleic acid comprising a nucleic acid sequence which hybridizes under stringent conditions, including a wash step of 0.2×SSC at 65° C., to at least one sequence selected from SEQ ID NO: 1 or SEQ ID NO: 3. Exemplary nucleic acids encode polypeptides which possess one or more of the following characteristics: (i) the ability to phosphorylate Chk1 proteins; (ii) the ability to bind to single-stranded DNA; (iii) the ability to bind to double-stranded DNA; (iv) the ability to induce cell cycle delay in response to UV damaged DNA; and/or (v) the ability to induce cell cycle delay in response to a DNA replication block.

In one embodiment, the isolated nucleic acid comprises at least one nucleic acid sequence selected from SEQ ID NO: 1, SEQ ID NO: 3, or a fragment of at least 150, 200, 225, 250, 300, 400, 450, 500, 600, 700, 750, 800 or 900 contiguous nucleotides thereof.

In a third aspect, the present invention provides isolated and/or recombinantly produced ATR polypeptides, and fragments thereof which retain at least one activity of an ATR polypeptide. For example, the present invention provides an isolated and/or recombinantly produced polypeptide comprising an amino acid sequence at least 80% identical to SEQ ID NO: 2, or a fragment of at least 50, 75, 100, 150, 200, 250 or 300 contiguous amino acids of SEQ ID NO: 2. Exemplary ATR polypeptides comprising an amino acid sequence at least 80% identical to SEQ ID NO: 2, or a fragment of at least 50 amino acids of SEQ ID NO: 2, possess one or more of the following characteristics (i.e., possess at least one activity of an ATR polypeptide): (i) the ability to phosphorylate Chk1 proteins; (ii) the ability to bind to single-stranded DNA; (iii) the ability to bind to double-stranded DNA; (iv) the ability to induce cell cycle delay in response to UV damaged DNA; and/or (v) the ability to induce cell cycle delay in response to a DNA replication block.

In one embodiment, the polypeptide comprises an amino acid sequence at least 90%, 95%, 98,%, or even 99% identical to SEQ ID NO: 2, or a fragment of at least 50, 75, 100, 150, 200, 250 or 300 contiguous amino acids of SEQ ID NO: 2. Exemplary ATR polypeptides, or fragments thereof, possess one or more of the following characteristics (i.e., possess at least one activity of an ATR polypeptide): (i) the ability to phosphorylate Chk1 proteins; (ii) the ability to bind to single-stranded DNA; (iii) the ability to bind to double-stranded DNA; (iv) the ability to induce cell cycle delay in response to UV damaged DNA; and/or (v) the ability to induce cell cycle delay in response to a DNA replication block.

In another embodiment, the polypeptide comprises an amino acid sequence encoded by a nucleic acid sequence which hybridizes under stringent conditions, including a wash step of 0.2×SSC at 65° C., to at least one nucleic acid sequence selected from SEQ ID NO: 1 or SEQ ID NO: 3. Exemplary polypeptides, or fragments thereof, possess one or more of the following characteristics (i.e., possess at least one activity of an ATR polypeptide): (i) the ability to phosphorylate Chk1 proteins; (ii) the ability to bind to single-stranded DNA; (iii) the ability to bind to double-stranded DNA; (iv) the ability to induce cell cycle delay in response to UV damaged DNA; and/or (v) the ability to induce cell cycle delay in response to a DNA replication block.

In another embodiment, the polypeptide comprises an amino acid sequence identical to SEQ ID NO: 2, or a fragment of at least 50, 75, 100, 150, 200, 250 or 300 contiguous amino acids of SEQ ID NO: 2.

In yet another embodiment, the polypeptide is a non-mammalian ATR polypeptide. In another embodiment, the polypeptide is an amphibian or fish ATR polypeptide. Exemplary fish include, but are not limited to, zebrafish. In still another embodiment, the non-mammalian amphibian is a frog, toad, or newt. Exemplary amphibian species include, but are not limited to, *Xenopus laevis, Xenopus tropicalis, Rana pipiens, Rana catesbeiana, Rana temporaria, Rana sylvatica*, and *Bufo bufo*. In still another embodiment, the polypeptide is a *Xenopus laevis* or *Xenopus tropicalis* ATR polypeptide.

In any of the foregoing embodiments of this aspect of the invention, the polypeptide comprises an amino acid sequence at least 80%, 85%, 90%, 95%, 98%, or 100% identical to residues 2208–2654 of SEQ ID NO: 2 or residues 2351–2654 of SEQ ID NO: 2.

In a fourth aspect of the present invention, the subject nucleic acids can be used to generate expression constructs, such as by placing a transcriptional regulatory sequence in operable linkage with the ATR coding sequence. Accordingly, expression vectors encoding the subject polypeptides can be generated using expression vectors capable of replicating in at least one of a prokaryotic cell and a eukaryotic cell.

Thus, the present invention further pertains to a host cell transfected with such an expression vector, e.g., expressing recombinant ATR polypeptides, as well as methods of producing a recombinant ATR polypeptide by culturing the instant cell to express the recombinant polypeptide.

In a fifth aspect, the present invention provides fusion proteins comprising an ATR polypeptide. Exemplary fusion proteins comprise an ATR polypeptide of the present invention and a detectable label for detecting the presence of the fusion protein. Further exemplary fusion proteins comprise an ATR polypeptide of the present invention and a matrix-binding domain for immobilizing said fusion protein.

In a sixth aspect, the present invention provides methods and compositions for the preparation of antibodies. In one embodiment, the invention provides an immunogen comprising a portion of a subject ATR polypeptide (e.g., a polypeptide comprising an amino acid sequence at least 80% identical to all or a portion of SEQ ID NO: 2). In another embodiment, the invention provides an antibody preparation specifically reactive with an epitope of a subject ATR polypeptide (e.g., a polypeptide comprising an amino acid sequence at least 80% identical to all or a portion of SEQ ID NO: 2).

In a related aspect, the invention provides an isolated antibody, or a fragment thereof. The antibody may be a monoclonal antibody or a polyclonal antibody, and may optionally be labeled with a detectable label. In one embodiment, said antibody, or fragment thereof, is specifically immunoreactive with a polypeptide encoded by a nucleic acid sequence which hybridizes under stringent conditions, including a wash step of 0.2× SSC at 65° C., to a nucleic acid sequence of SEQ ID NO: 1 or SEQ ID NO: 3. Said antibody, optionally, does not substantially cross-react with a mammalian ATR protein.

In another embodiment, said antibody, or fragment thereof, is specifically immunoreactive with a polypeptide comprising an amino acid sequence at least 80%, 90%, 95%, or 98% identical to the amino acid sequence of SEQ ID NO: 2. In yet another embodiment, said antibody, or fragment thereof, is specifically immunoreactive with a polypeptide comprising an amino acid sequence identical to the amino acid sequence of SEQ ID NO: 2. Said antibody, optionally, does not substantially cross-react with a mammalian ATR protein.

In a seventh aspect, the invention provides a preparation comprising a polypeptide that includes an amino acid sequence formulated in a pharmaceutically acceptable carrier. The preparation comprises a polypeptide including an amino acid sequence which hybridizes under stringent conditions, including a wash step of 0.2×SSC at 65° C., to a nucleic acid sequence selected from SEQ ID NO: 1 or SEQ ID NO: 3 formulated in a pharmaceutically acceptable carrier or excipient. The polypeptide has one or more of the following functions (1) can phosphorylate a CDK1 protein; (ii) can bind to single-stranded DNA; (iii) can bind to double-stranded DNA; (iv) can induce cell cycle delay in response to UV damaged DNA; and/or (v) can induce cell cycle delay in response to a DNA replication block.

In an eighth aspect, the present invention also relates to transgenic animals having cells which harbor or contain a transgene encoding a recombinant ATR polypeptide, or in which the endogenous gene has been inactivated, e.g., by homologous recombination, transposon or P-element mediated transposition, chemical or radiation induced mutagenesis.

In one embodiment, the transgenic animal is a non-mammalian animal. In another embodiment, the non-mammalian animal is an amphibian or fish. In still another embodiment, the non-mammalian animal is a zebrafish. In still another embodiment, the non-mammalian amphibian is a frog, toad, or newt. Exemplary amphibian species include, but are not limited to, *Xenopus laevis, Xenopus tropicalis, Rana pipiens, Rana catesbeiana, Rana temporaria, Rana sylvatica*, and *Bufo bufo*.

In a ninth aspect, the invention provides immunodepleted egg extracts. Such extracts are immunodepleted of ATR protein (e.g., expression of ATR protein has been decreased in comparison to a wildtype egg extract). In one embodiment, egg extracts are incubated with anti-ATR antibodies to decrease the amount of ATR protein in the extract (to immunodeplete the extract). In exemplary immunodepleted egg extracts expression of ATR protein is decreased by at least 50% in comparison to control egg extracts. Such immunodepleted egg extracts have substantial utility in methods of screening and drug discovery.

In a tenth aspect, the invention provides a non-mammalian egg extract "charged" with a mammalian ATR protein. This tenth aspect of the invention is based on evidence, presented herein, that demonstrates that the phosphorylation of Chk1 by ATR is direct, and that this event is evolutionarily conserved. The tremendous level of conservation is seen by experiments which show that a human ATR polypeptide phosphorylates a *Xenopus* Cdk1 protein. By "charged" is meant that the mammalian ATR protein is expressed in the non-mammalian egg extract (for example, using methods provided in the Experiments).

In one embodiment, the non-mammalian extract is a wildtype egg extract (e.g., the egg extract also comprises endogenous ATR protein, as well as wildtype Chk1 protein, etc,)

In another embodiment, the non-mammalian extract has been immunodepleted of endogenous non-mammalian ATR.

In yet another embodiment, the non-mammalian extract is a mutant egg extract (e.g., the egg extract comprises mutant endogenous proteins).

In an eleventh aspect, the present invention provides a variety of methods for screening for agents which modulate at least one activity of an ATR polypeptide. By modulate is meant to include agents which either increase or decrease activity. By agents is meant to include one or more nucleic acids, peptides, proteins, antisense RNAs, RNAi constructs, antibodies, chemical compounds, and small organic molecules. By at least one activity of an ATR polypeptide includes (1) the ability to phosphorylate a Chk1 protein, (ii) the ability to bind single-stranded DNA, (iii) the ability to bind double stranded DNA, (iv) the ability to induce cell cycle delay in response to UV damaged DNA; and/or (v) the ability to induce cell cycle delay in response to a DNA replication block.

The present invention shows, for the first time, that Chk1 is a direct substrate for ATR. Accordingly, one embodiment of this aspect of the invention provides methods of screening for agents which modulate phosphorylation of a Chk1 protein by an ATR polypeptide. To illustrate, the method comprises providing a preparation comprising an ATR polypeptide and a Chk1 polypeptide, and prior to phosphorylation of said Chk1 polypeptide by said ATR polypeptide, contacting the preparation with one or more agents. The phosphorylation of said Chk1 polypeptide by said ATR polypeptide can then be measured in the presence versus the absence of said one or more agents. An agent which modulates (either increases or decreases) the phosphorylation of a Chk1 polypeptide by an ATR polypeptide is a modulator of phosphorylation.

Given the importance of proper checkpoint control in maintaining genomic stability and preventing mis-regulation of cell proliferation, agents identified by the subject methods which modulate an activity of an ATR polypeptide have utility as therapeutics for a range of proliferative disorders (e.g., any form of cancer). Accordingly, in a twelfth aspect the present invention contemplates methods of treatment based on administering to patients therapeutically effective amounts of agents which modulate one or more activities of an ATR polypeptide.

In a related aspect, the present invention further contemplates methods of conducting a business based on the identification and use of agents which modulate one or more activities of an ATR polypeptide. In one embodiment, the present invention provides a method of conducting a drug discovery business. The method comprises identifying one or more agents which modulate at least one activity of an ATR polypeptide (such as an agent which modulates the phosphorylation of Chk1 by ATR), conducting therapeutic profiling of said one or more agents to establish efficacy and toxicity profiles, and formulating a pharmaceutical preparation including one or more of the agents identified in the methods of the present invention and determined to have an acceptable therapeutic profile. The method may optionally include establishing a system for distributing the pharmaceutical preparation for sale, and/or establishing a sales group for marketing the pharmaceutical preparation.

In another embodiment, the invention provides a method of conducting a drug discovery business. The method comprises identifying one or more agents which modulate at least one activity of an ATR polypeptide (such as an agent which modulates the phosphorylation of Chk1 by ATR), and licensing the rights to said agents to a third party for further research and development.

As outlined above, the present invention contemplates methods of conducting a drug discovery business based on the agents which modulate one or more activities of an ATR polypeptide. In certain embodiments, the initially identified agents can be subjected to further lead optimization, e.g., to further refine the structure of a lead compound so that potency and activity are maintained but balanced with important pharmacological characteristics including:
   Solubility
   Permeability
   Bioavailability
   Toxicity
   Mutagenicity
   Pharmacokinetics—absorption, distribution, metabolism, elimination of the drug Even where lead agents are identified using in vivo methods, the above characteristics must still be optimized in order to ultimately provide a preparation suitable for use in humans. Structural modifications are made to a lead compound to address issues with the parameters listed above. These modifications however, must take into account possible effects on the molecule's potency and activity. For example, if the solubility of a lead compound is poor, changes can be made to the molecule in an effort to improve solubility; these modifications, however, may negatively affect the molecule's potency and activity.

A candidate agent, or combinations thereof, must then be tested for efficacy and toxicity in further animal models. Such therapeutic profiling is commonly employed in the pharmaceutical arts. Before testing an experimental drug in humans, extensive therapeutic profiling (preclinical testing) must be completed to establish initial parameters for safety and efficacy. Preclinical testing establishes a mechanism of action for the drug, its bioavailability, absorption, distribution, metabolism, and elimination through studies performed in vitro (that is, in test tubes, beakers, petri dishes, etc.) and in animals. Animal studies are used to assess whether the drug will provide the desired results. Varying doses of the experimental drug are administered to test the drug's efficacy, identify harmful side-effects that may occur, and evaluate toxicity.

In one embodiment, the step of therapeutic profiling includes toxicity testing of agents; analysis of pharmacokinetics and metabolism of the candidate agent; and determination of efficacy in animal models. In certain instances, the method can include analyzing structure-activity relationship and optimizing lead structures based on efficacy, safety and pharmacokinetic profiles. The goal of such steps is the selection of drug candidates for pre-clinical studies to lead to filing of Investigational New Drug applications ("IND") with the FDA prior to human clinical trials.

Between lead optimization and therapeutic profiling, one goal of the subject method is to develop an agent which has minimal side-effects. By toxicity profiling is meant the evaluation of potentially harmful side-effects which may occur when an effective amount of a pharmaceutical preparation is administered. A side-effect may or may not be harmful, and the determination of whether a side effect associated with a pharmaceutical preparation is an acceptable side effect is made by the Food and Drug Administration during the regulatory approval process. This determination does not follow hard and fast rules, and that which is considered an acceptable side effect varies due to factors including: (a) the severity of the condition being treated, and (b) the availability of other treatments and the side-effects currently associated with these available treatments.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, Molecular Cloning: A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

Other features and advantages of the invention will be apparent from the following detailed description, and from the claims.

BRIEF DESCRIPTION OF THE DRAWINGS

FIG. 1 shows an amino acid alignment of the C-terminal region of Xatr, human ATR, Mei-43, Rad3, and Mec1, which amino acid sequences are represented by SEQ ID NOs. 6–10.

FIG. 8A also shows that recombinantly produced wildtype (Xchk1-GST-His6) or 4AQ mutant (Xchk1-4AQ-GST-His6) protein can be added back to the immunodepleted extracts (compare the top band in lanes 4 and 5 with lanes 1–3).

Figure 2:
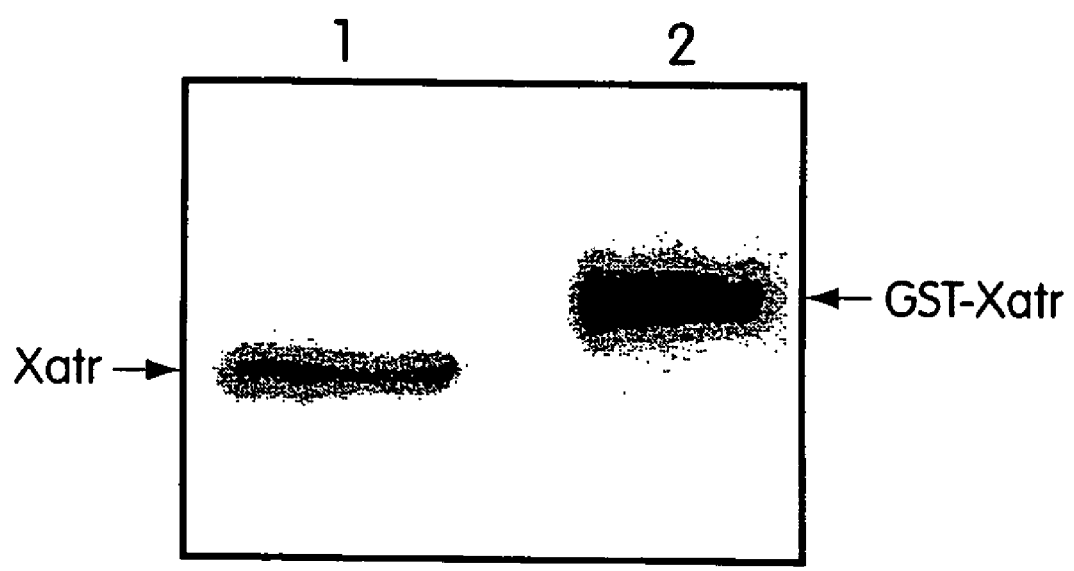
FIG. 2 shows immunoblot analysis using polyclonal antibody immunoreactive with His6-Xatr(2351–2654). Purified antibody recognized an approximately 300 kD protein in Xenopus egg extracts (lane 1), as well as a recombinant GST-Xatr fusion protein (lane 2).

DETAILED DESCRIPTION OF THE INVENTION (i) Definitions

For convenience, certain terms employed in the specification, examples, and appended claims are collected here.

As used herein, "protein" is any polymer consisting essentially of any of the 20 amino acids. Although "polypeptide" is often used in reference to relatively large polypeptides, and "peptide" is often used in reference to small polypeptides, usage of these terms in the art overlaps and is varied.

The terms "peptide(s)", "protein(s)" and "polypeptide(s)" are used interchangeably herein. The terms "polynucleotide sequence" and "nucleotide sequence" are also used interchangeably herein.

"Recombinant," as used herein, means that a protein is derived from a prokaryotic or eukaryotic expression system.

The term "wild type" refers to the naturally-occurring polynucleotide sequence of an exon of a protein, or a portion thereof, or protein sequence, or portion thereof, respectively, as it normally exists in vivo.

The term "mutant" refers to any change in the genetic material of an organism, in particular any change (i.e., deletion, substitution, addition, or alteration) in a wild type polynucleotide sequence or any change in a wild type protein. The term "mutein" is used interchangeably with "mutant".

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a polypeptide or, where anti-sense expression occurs from the transferred gene, the expression of a naturally-occurring form of a protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms the protein.

As used herein, the term "tissue-specific promoter" means a DNA sequence that serves as a promoter, i.e., regulates expression of a selected DNA sequence operably linked to the promoter, and which effects expression of the selected DNA sequence in specific cells of a tissue, such as cells of neural origin, e.g. neuronal cells. The term also covers so-called "leaky" promoters, which regulate expression of a selected DNA primarily in one tissue, but cause expression in other tissues as well.

"Homology" and "identity" are used synonymously throughout and refer to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

A "chimeric protein" or "fusion protein" is a fusion of a first amino acid sequence encoding one of the subject polypeptides with a second amino acid sequence defining a domain (e.g. polypeptide portion) foreign to and not substantially homologous with any domain of one of the subject polypeptides. A chimeric protein may present a foreign domain which is found (albeit in a different protein) in an organism which also expresses the first protein, or it may be an "interspecies", "intergenic", etc. fusion of protein structures expressed by different kinds of organisms.

As used herein, a "transgenic animal" is any animal, preferably a non-human mammal, bird, fish or amphibian, in which one or more of the cells of the animal contain heterologous nucleic acid introduced by way of human intervention, such as by trangenic techniques well known in the art. The nucleic acid is introduced into the cell, directly or indirectly, by way of deliberate genetic manipulation, such as by microinjection, by infection with a recombinant virus, by transposition, or other methods well known in the art. The term genetic manipulation does not include classical cross-breeding, or in vitro fertilization, but rather is directed to the introduction of a recombinant DNA molecule. This molecule may be integrated within a chromosome, or it may be extrachromosomally replicating DNA.

As used herein, the term "transgene" means a nucleic acid sequence which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

The "non-human animals" of the invention include vertebrates such as rodents, non-human primates, sheep, cats, dogs, cows, pigs, rabbits, avians, amphibians, fish, reptiles, etc. The term "non-mammalin animals" include avians, amphibians, fish, reptiles, etc. Preferred non-mammalian animals are selected from amphibians and fish. Exemplary fish include, without limitation, zebrafish. Exemplary amphibians include, without limitation, frogs, newts and toads (e.g., *Xenopus laevis, Xenopus tropicalis, Rana pipiens, Rana catesbeiana, Rana temporaria, Rana sylvatica*, and *Bufo bufo*.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding an ATR polypeptide preferably includes no more than 10 kilobases (kb) of nucleic acid sequence which naturally immediately flanks the ATR gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As used herein, "proliferating" and "proliferation" refer to cells undergoing mitosis.

The term "agent" refers to any compound screened by the methods of the present invention. Agents which may be screened by the subject methods include nucleic acids, peptides, proteins, small organic molecules, chemical compounds, ribozymes, RNAi constructs, antisense RNAs, and antibodies. Agents screened by the subject methods can be administered individually, or can be administered in combination with one or more other agents. The invention further contemplates the screening of libraries of agents. Such libraries may include, without limitation, cDNA libraries (either plasmid based or phage based), expression libraries, combinatorial libraries, chemical libraries, phage display libraries, variegated libraries, and biased libraries.

The term "library" refers to any collection of nucleic acids, proteins, peptides, chemical compounds, small organic molecules, or antibodies. Libraries comprising each of these are well known in the art. Exemplary types of libraries include combinatorial, variegated, biased, and unbiased libraries. Libraries can provide a systematic way to screen large numbers of nucleic acids, proteins, peptides, chemical compounds, small organic molecules, or antibodies. Often, libraries are sub-divided into pools containing some fraction of the total species represented in the entire library. These pools can then be screened to identify fractions containing the desired activity. The pools can be further subdivided, and this process can be repeated until either (i) the desired activity can be correlated with a specific species contained within the library, or (ii) the desired activity is lost during further subdivision of the pool of species, and thus is the result of multiple species contained within the library.

Chk1 as used herein, refers to the amino acid or nucleic acid sequences of Chk1 obtained from any species. Exemplary species include mammals such as cows, pigs, rabbits, mice, rats, dogs, cats, horses, goats, sheep, non-human primates, and humans. Further exemplary species include amphibians, reptiles, and fish. Nucleic acid and amino acid sequences of Chk1 are represented, for example, in GenBank Accession Nos: AF117816, AB019218, AF053120, AF032875, AF016583, and NM_001274.

(ii) Exemplary Compositions

As described below, one aspect of the invention pertains to isolated nucleic acids comprising nucleotide sequences encoding ATR polypeptides, for example as illustrated by SEQ ID NO: 2, and/or equivalents of such nucleic acids. The term nucleic acid as used herein is intended to include fragments as equivalents. The term equivalent is understood to include nucleotide sequences encoding ATR polypeptides which are functionally equivalent to the ATR polypeptide represented in SEQ ID NO: 2. Equivalent nucleotide sequences will include sequences that differ by one or more nucleotide substitutions, additions or deletions, such as allelic variants; and will, therefore, include sequences that differ from the nucleotide sequence of the Xenopus ATR coding sequence of SEQ ID No: 1 or SEQ ID NO: 3 due to the degeneracy of the genetic code. Equivalents will also include nucleotide sequences that hybridize under stringent conditions (i.e., equivalent to about 20–27° C. below the melting temperature ($T_m$) of the DNA duplex formed in about 1M salt) to the nucleotide sequences represented in SEQ ID No: 1 or SEQ ID NO: 3.

Moreover, it will be generally appreciated that, under certain circumstances, it may be advantageous to provide homologs of an ATR polypeptide which function in a limited capacity as one of either an agonist (e.g., mimics or potentiates a bioactivity of the wild-type ATR protein) or an antagonist (e.g., inhibits a bioactivity of the wild-type ATR protein), in order to promote or inhibit only a subset of the biological activities of the naturally-occurring form of the protein. Thus, specific biological effects can be elicited by treatment with a homolog of limited function.

Variants of the subject ATR polypeptides can be generated by mutagenesis, such as by discrete point mutation(s), or by truncation. For instance, mutation can give rise to variants which retain substantially the same, or merely a subset, of the biological activity of the ATR polypeptide from which it was derived. Alternatively, antagonistic forms of the protein can be generated which are able to inhibit the function of the naturally occurring form of the protein. Thus, ATR polypeptides provided by the subject invention may be either positive or negative regulators of an activity of an ATR polypeptide.

In general, polypeptides referred to herein as having an activity of an ATR polypeptide (e.g., are "bioactive") are defined as polypeptides which include an amino acid sequence corresponding (e.g., at least 80%, 85%, 90%, 95%, 98%, 100% identical) to all or a portion of the amino acid sequences of the ATR polypeptide shown in SEQ ID No: 2, and which agonize or antagonize all or a portion of the biological/biochemical activities of a naturally occurring ATR protein. Examples of such biological activity includes the ability to phosphorylate Chk1 proteins, the ability to bind single stranded DNA, the ability to bind double stranded DNA, the ability to induce cell cycle delay in response to DNA damage, and the ability to induce cell cycle delay in response to a DNA replication block. The bioactivity of certain embodiments of the subject ATR polypeptides can be characterized in terms of an ability to induce cell cycle delay in response to DNA damage and/or a DNA replication block.

Another aspect of the invention provides a nucleic acid which hybridizes under high or low stringency conditions to a nucleic acid represented by one of SEQ ID Nos: 1 or 3. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Nucleic acids having a sequence that differs from the nucleotide sequences shown in one of SEQ ID NO: 1 or SEQ ID NO: 3 due to degeneracy in the genetic code are also within the scope of the invention. Such nucleic acids encode functionally equivalent peptides but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence. However, it is expected that DNA sequence polymorphisms that do lead to changes in the amino acid sequences will also exist. One skilled in the art will appreciate that these variations in one or more nucleotides (up to about 3–5% of the nucleotides) of the nucleic acids encoding polypeptides having an activity of an ATR polypeptide may exist among individuals of a given species due to natural allelic variation.

Fragments of the nucleic acids encoding an active portion of the ATR proteins are also within the scope of the invention. As used herein, an ATR gene fragment refers to a nucleic acid having fewer nucleotides than the nucleotide sequence encoding the entire amino acid sequence of an ATR protein represented in SEQ ID NO: 1 or SEQ ID NO: 3, yet which (preferably) encodes a peptide which retains some biological activity of the full length protein, e.g. the fragment retains the ability to phosphorylate Chk1 proteins, to bind single stranded DNA, to bind double stranded DNA, and/or to induce a cell cycle delay in response to DNA damage or a DNA replication block. Nucleic acid fragments within the scope of the present invention include those capable of hybridizing under high or low stringency conditions with the nucleic acids represented in SEQ ID NO: 1 or SEQ ID NO: 3. Nucleic acids within the scope of the invention may also contain linker sequences, modified restriction endonuclease sites and other sequences useful for molecular cloning, expression or purification of recombinant forms of the subject polypeptides.

This invention also provides expression vectors containing a nucleic acid encoding an ATR polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the subject proteins. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences, sequences that control the expression of a DNA sequence when operatively linked to it, may be used in these vectors to express DNA sequences encoding the polypeptides of this invention. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

Moreover, the gene constructs of the present invention can also be used to deliver nucleic acids encoding the subject polypeptides. Thus, another aspect of the invention features expression vectors for in vivo or in vitro transfection and expression of a subject polypeptide in particular cell types.

Expression constructs of the subject polypeptide, including agonistic and antagonist variants thereof, may be administered in any biologically effective carrier, e.g. any formulation or composition capable of effectively delivering the recombinant gene to cells in vivo or in vitro. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation. One of skill in the art can readily select from amongst available vectors and methods of delivery in order to optimize expression in a particular cell type or under particular conditions.

A preferred approach for introduction of nucleic acid into a cell is by use of a viral vector containing nucleic acid, e.g. a cDNA, encoding the particular form of the polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76: 271). Thus, recombinant retrovirus can be constructed in which part of the retroviral coding sequence (gag, pol, env) has been replaced by nucleic acid encoding one of the subject proteins rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neuronal cells, in vitro and/or in vivo (see for example Eglitis, et al. (1985) *Science* 230: 1395–1398; Danos and Mulligan (1988) *Proc. Natl. Acad. Sci. USA* 85: 6460–6464; Wilson et al. (1988) *Proc. Natl. Acad. Sci. USA* 85: 3014–3018; Armentano et al. (1990) *Proc. Natl. Acad. Sci. USA* 87: 6141–6145; Huber et al. (1991) *Proc. Natl. Acad. Sci. USA* 88: 8039–8043; Ferry et al. (1991) *Proc. Natl. Acad. Sci. USA* 88: 8377–8381; Chowdhury et al. (1991) *Science* 254: 1802–1805; van Beusechem et al. (1992) *Proc. Natl. Acad. Sci. USA* 89: 7640–7644; Kay et al. (1992) *Human Gene Therapy* 3: 641–647; Dai et al. (1992) *Proc. Natl. Acad. Sci. USA* 89: 10892–10895; Hwu et al. (1993) *J. Immunol.* 150: 4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86: 9079–9083; Julan et al. (1992) *J. Gen Virol* 73: 3251–3255; and Goud et al. (1983) *Virology* 163: 251–254); or coupling cell surface receptor ligands to the viral env proteins (Neda et al. (1991) *J Biol Chem* 266: 14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the gene of the retroviral vector.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6: 616; Rosenfeld et al. (1991) *Science* 252: 431–434; and Rosenfeld et al. (1992) *Cell* 68: 143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including airway epithelium (Rosenfeld et al. (1992) cited supra), endothelial cells (Lemarchand et al. (1992) *Proc. Natl. Acad. Sci. USA* 89: 6482–6486), hepatocytes (Herz and Gerard (1993) *Proc. Natl. Acad. Sci. USA* 90: 2812–2816) and muscle cells (Quantin et al. (1992) *Proc. Natl. Acad. Sci. USA* 89: 2581–2584). Furthermore, the virus particle is relatively stable and amenable to purification and concentration, and as above, can be modified so as to affect the spectrum of infectivity.

Yet another viral vector system useful for delivery of one of the subject genes is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158: 97–129). It is also one of the few viruses that may integrate its DNA into non-dividing cells, and exhibits a high frequency of stable integration (see for example Flotte et al. (1992) *Am. J. Respir. Cell. Mol. Biol.* 7: 349–356; Samulski et al. (1989) *J. Virol.* 63: 3822–3828; and McLaughlin et al. (1989) *J. Virol.* 62: 1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5: 3251–3260 can be used to introduce DNA into cells. A variety of nucleic acids have been introduced into different cell types using AAV vectors (see for example Hermonat et al. (1984) *Proc. Natl. Acad. Sci. USA* 81: 6466–6470; Tratschin et al. (1985) *Mol. Cell. Biol.* 4: 2072–2081; Wondisford et al. (1988) *Mol. Endocrinol.* 2: 32–39; Tratschin et al. (1984) *J. Virol.* 51: 611–619; and Flotte et al. (1993) *J. Biol. Chem.* 268: 3781–3790).

The above cited examples of viral vectors are by no means exhaustive. Herpes-simplex viral vectors and lentiviral vectors are just two additional types of viral vectors which can be used in the present invention.

In addition to viral transfer methods, such as those illustrated above, non-viral methods can also be employed to cause expression of a subject polypeptide. Most nonviral methods of gene transfer rely on normal mechanisms used by cells for the uptake and intracellular transport of macromolecules. In preferred embodiments, non-viral gene delivery systems of the present invention rely on endocytic pathways for the uptake of the subject polypeptide gene by the targeted cell. Exemplary gene delivery systems of this type include liposomal derived systems, poly-lysine conjugates, and artificial viral envelopes.

Another aspect of the present invention concerns recombinant forms of the subject ATR proteins. Recombinant polypeptides preferred by the present invention, in addition to native ATR proteins, are at least 60% identical, more preferably 70% identical and most preferably 80% identical with an amino acid sequence represented in SEQ ID NO: 2.

Additional preferred recombinant polypeptides comprise an amino acid sequence at least 85%, 90%, 95%, 98%, or 100% identical to an amino acid sequence represented in SEQ ID NO: 2. The invention further concerns polypeptides comprising an amino acid sequence at least 80%, 85%, 90%, 95%, 98% or 100% identical to a fragment of SEQ ID NO: 2. Any of the foregoing polypeptides comprising all or a portion of SEQ ID NO: 2 may be characterized by at least one activity of an ATR polypeptide including (1) the ability to phosphorylate Chk1, (2) the ability to bind single-stranded DNA, (3) the ability to bind double stranded DNA, (4) the ability to induce cell cycle arrest in response to DNA damage, and/or (5) the ability to induce cell cycle arrest in response to a DNA replication block.

The term "recombinant protein" refers to a polypeptide of the present invention which is produced by recombinant DNA techniques, wherein generally, nucleic acid encoding a polypeptide is inserted into a suitable expression vector which is in turn used to transform a host cell to produce the heterologous protein. Moreover, the phrase "derived from", with respect to a recombinant gene, is meant to include within the meaning of "recombinant protein" those proteins having an amino acid sequence of a native protein, or an amino acid sequence similar thereto which is generated by mutations including substitutions and deletions (including truncation) of a naturally occurring form of the protein (i.e., variants).

The present invention further pertains to recombinant forms of one of the subject polypeptides which are encoded by genes derived from an organism, and which have amino acid sequences evolutionarily related to the polypeptide represented in SEQ ID NO: 2. Such recombinant polypeptides preferably are capable of functioning in one of either role of an agonist or antagonist of at least one biological activity of a wild-type ("authentic") ATR protein. The term "evolutionarily related to", with respect to amino acid sequences of proteins, refers to both polypeptides having amino acid sequences which have arisen naturally, and also to mutational variants of polypeptides which are derived, for example, by combinatorial mutagenesis. Such evolutionarily derived polypeptides preferred by the present invention are at least 60% identical, more preferably 70% identical and most preferably 80% identical with the amino acid sequence of SEQ ID NO: 2. Polypeptides having at least about 85%, 90%, 95%, 98%, or even 99% identity with SEQ ID NO: 2 are also within the scope of the invention.

The present invention further pertains to methods of producing the subject polypeptides. For example, a host cell transfected with a nucleic acid vector directing expression of a nucleotide sequence encoding the subject polypeptides can be cultured under appropriate conditions to allow expression of the peptide to occur. The polypeptide may be secreted and isolated from a mixture of cells and medium containing the recombinant polypeptide. Alternatively, the peptide may be retained cytoplasmically by removing the signal peptide sequence from the recombinant gene and the cells harvested, lysed and the protein isolated. A cell culture includes host cells, media and other by-products. Suitable media for cell culture are well known in the art. The recombinant polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant polypeptide is a fusion protein containing a domain which facilitates its purification, such as a GST fusion protein. In another preferred embodiment, the subject recombinant polypeptide may include one or more additional domains which facilitate immunodetection, purification, and the like. Exemplary domains include HA, FLAG, GST, His, and the like.

This invention also pertains to a host cell transfected to express a recombinant form of the subject polypeptides. The host cell may be any prokaryotic or eukaryotic cell. Thus, a nucleotide sequence derived from the cloning of a protein (for example, a *Xenopus* ATR protein) encoding all or a selected portion of the full-length protein, can be used to produce a recombinant form of a polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant polypeptides by microbial means or tissue-culture technology in accord with the subject invention. We note that such methods are also effectively used to produce experimentally useful proteins which include all or a portion of the subject nucleic acids. For example, such methods are used to produce fusion proteins including domains which facilitate purification or immunodetection, and to produce recombinant mutant forms of a protein (for example a kinase dead form of a protein which acts as a kinase).

The recombinant genes can be produced by ligating nucleic acid encoding a protein, or a portion thereof, into a vector suitable for expression in either prokaryotic cells, eukaryotic cells, or both. Expression vectors for production of recombinant forms of the subject polypeptides include plasmids and other vectors. For instance, suitable vectors for the expression of a polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, an ATR polypeptide is produced recombinantly utilizing an expression vector generated by sub-cloning the coding sequence of one of the genes represented in SEQ ID Nos: 1 or 3.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169: 751–757) and *Salmonella typhimurium* and its in vitro activity has been demonstrated on recombinant proteins (Miller et al. (1987) *PNAS* 84: 2718–1722). Therefore, removal of an N-terminal methionine, if desired, can be achieved either in vivo or in vitro.

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a protein. For example, the VP6 capsid protein of rotavirus can be used as an immunologic carrier protein for portions of the polypeptide, either in the monomeric form or in the form of a viral particle.

In addition to utilizing fusion proteins to enhance immunogenicity, it is widely appreciated that fusion proteins can also facilitate the expression, purification, and/or detection of proteins. For example, polypeptides can be generated as glutathione-S-transferase (GST-fusion) proteins. Such GST-fusion proteins can enable easy purification of a polypeptide, as for example by the use of glutathione-derivatized matrices (see, for example, *Current Protocols in Molecular Biology*, eds. Ausubel et al. (N.Y.: John Wiley & Sons, 1991)). In another embodiment, a fusion gene coding for a purification leader sequence, such as a poly-(His)/enterokinase cleavage site sequence, can be used to replace the signal sequence which naturally occurs at the N-terminus of the protein (e.g., of the pro-form, in order to permit purification of the poly(His)-proteinX protein by affinity chromatography using a $Ni^{2+}$ metal resin. The purification leader sequence can then be subsequently removed by treatment with enterokinase (e.g., see Hochuli et al. (1987) *J. Chromatography* 411: 177; and Janknecht et al. *PNAS* 88: 8972).

Techniques for making fusion genes are known to those skilled in the art. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

The present invention also makes available isolated polypeptides which are isolated from, or otherwise substantially free of other cellular and extracellular proteins. The term "substantially free of other cellular or extracellular proteins" (also referred to herein as "contaminating proteins") or "substantially pure or purified preparations" are defined as encompassing preparations having less than 20% (by dry weight) contaminating protein, and preferably having less than 5% contaminating protein. Functional forms of the subject polypeptides can be prepared, for the first time, as purified preparations by using a cloned gene as described herein. By "purified", it is meant, when referring to a peptide or nucleic acid sequences, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" arid "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

Isolated peptidyl portions of proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry.

The recombinant polypeptides of the present invention also include versions of those protein which are resistant to proteolytic cleavage, as for example, due to mutations which alter potential cleavage sequences or which inactivate an enzymatic activity associated with the protein. Variants of the present invention also include proteins which have been post-translationally modified in a manner different than the authentic protein.

Modification of the structure of the subject polypeptides can be for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, WH Freeman and Co.: 1981). Whether a change in the amino acid sequence of a peptide results in a functional variant (e.g. functional in the sense that it acts to mimic or antagonize the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject proteins as well as truncation mutants, and is especially useful for identifying potential variant sequences that maintain at least one function (activity) of a wildtype ATR polypeptide. The purpose of screening such combinatorial libraries is to generate, for example, novel variants which can act as either agonists or antagonists, or alternatively, possess novel activities all together. To illustrate, ATR variants can be engineered by the present method to provide more efficient phosphorylation of Chk1 proteins, or to provide increased or decreased affinity for single-stranded or double-stranded DNA. Thus, combinatorially-derived variants can be generated to have an increased potency relative to a naturally occurring form of the protein. Likewise, variants can be generated by the present combinatorial approach to act as antagonists.

In one aspect of this method, the amino acid sequences for a population of ATR proteins (for examples human, mouse, and *Xenopus* ATR) or other related proteins (for example ATR's and ATM's from various species) are aligned, preferably to promote the highest homology possible. Amino acids which appear at each position of the aligned sequences are selected to create a degenerate set of combinatorial sequences. In a preferred embodiment, the variegated library of variants is generated by combinatorial mutagenesis at the nucleic acid level, and is encoded by a variegated gene library. For instance, a mixture of synthetic oligonucleotides can be enzymatically ligated into gene sequences such that the degenerate set of potential sequences are expressible as individual polypeptides, or alternatively, as a set of larger fusion proteins (e.g. for phage display) containing the set of sequences therein.

There are many ways by which the library of potential variants can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential variant sequences. The synthesis of degenerate oligonucleotides is well known in the art (see for example, Narang, S A (1983) *Tetrahedron* 39: 3; Itakura et al. (1981) *Recombinant DNA, Proc 3rd Cleveland Sympos. Macromolecules*, ed. A G Walton, Amsterdam: Elsevier pp273–289; Itakura et al. (1984) *Annu. Rev. Biochem.* 53: 323; Itakura et al. (1984) *Science* 198: 1056; Ike et al. (1983) *Nucleic Acid Res.* 11: 477. Such techniques have been employed in the directed evolution of other proteins (see, for example, Scott et al. (1990) *Science* 249: 386–390; Roberts et al. (1992) *PNAS* 89: 2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of ATR variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of sequences created by combinatorial mutagenesis techniques.

The invention also provides for reduction of a protein to generate mimetics, e.g. peptide or non-peptide agents, which are able to disrupt an activity of an ATR polypeptide of the invention. An exemplary mimetic may disrupt the ability of an ATR polypeptide to phosphorylate Chk1, may disrupt the ability of an ATR polypeptide to bind single-stranded DNA, and/or may disrupt the ability of an ATR polypeptide to bind double-stranded DNA.

(iii) Antibodies

Another aspect of the invention pertains to an antibody specifically reactive with an ATR polypeptide of the invention. For example, by using immunogens derived from an ATR polypeptide, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., an ATR polypeptide, or an antigenic fragment thereof, which is capable of eliciting an antibody response). Techniques for conferring immunogenicity on a protein or peptide include conjugation to carriers or other techniques well known in the art. An immunogenic portion of a polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of an ATR polypeptide of the invention (e.g. antigenic determinants of a protein represented by SEQ ID NO: 2 or a variant at least 80%, 85%, 90%, 95%, or 98% identical to SEQ ID NO: 2). In some embodiments, the immunospecific subject antibodies do not substantially cross react with a mammalian ATR protein. In another embodiment, the immunospecific subject antibodies do not substantially cross react with a yeast ATR-related protein. In yet another embodiment, the immunospecific subject antibodies do not substantially cross react with a non-ATR PIK-domain containing related protein (e.g., ATM, DNA-PKcs). By "not substantially cross react", it is meant that the antibody has a binding affinity for a non-homologous protein which is at least one order of magnitude, more preferably at least 2 orders of magnitude, and even more preferably at least 3 orders of magnitude less than the binding affinity of the antibody for a polypeptide comprising an amino acid sequence represented in SEQ ID NO: 2.

Following immunization of an animal with an antigenic preparation of a protein, antisera can be obtained and, if desired, polyclonal antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include for example, the hybridoma technique (originally developed by Kohler and Milstein (1975) *Nature* 256: 495–497), the human B cell hybridoma technique (Kozbar et al. (1983) *Immunology Today*, 4: 72), and the EBV-hybridoma technique to produce human monoclonal antibodies (Cole et al. (1985) *Monoclonal Antibodies and Cancer Therapy*, Alan R. Liss, Inc. pp. 77–96). Hybridoma cells can be screened immunochemically for production of antibodies specifically reactive with the polypeptides of the present invention and monoclonal antibodies isolated from a culture comprising such hybridoma cells. Similarly, hybridoma cells can be screened for the production of antibodies specifically reactive with the polypeptides of the present invention, which also do not substantially cross-reactive with one or more other polypeptides.

The term antibody as used herein is intended to include fragments thereof which are also specifically reactive with one of the subject polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific and chimeric molecules having affinity for a protein conferred by at least one CDR region of the antibody.

Both monoclonal and polyclonal antibodies (Ab) have many uses including (1) blocking or antagonizing one or more activities of the subject polypeptide, (2) for detection of the subject proteins (in vitro or in vivo) using standard immunohistochemical/immunocytochemical techniques, (3) for immunodepletion, (4) for immuno-precipitation, and (5) for the immunological screening of cDNA libraries constructed in expression vectors such as λgt11, λgt18–23, λZAP, and λORF8.

The antibodies of the invention can be bound to many different carriers and used to detect the presence of an antigen comprising the polypeptides of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds.

Another technique that may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific anti hapten antibodies.

(iv) Transgenic animals

Another aspect of the invention features transgenic non-human animals which express a heterologous ATR gene of the present invention, or which have had one or more genomic ATR genes disrupted in at least one of the tissue or cell-types of the animal. Accordingly, the invention features an animal model for disease. In one embodiment, the transgenic non-human animals is a mammal such as a mouse, rat, rabbit, goat, sheep, dog, cat, cow, or non-human primate. In another embodiment, the non-human animals is a reptile, fish, avian, or amphibian. Exemplary avians include chickens. Exemplary fish include zebrafish and sticklebacks. Exemplary amphibians include newts, toads, and frogs. In two illustrative examples, the transgenic frog is selected from *Xenopus laevis* or *Xenopus tropicalis*.

Another aspect of the present invention concerns transgenic animals which are comprised of cells (of that animal) which contain a transgene of the present invention and which preferably (though optionally) express an exogenous ATR protein in one or more cells in the animal. A transgene can encode the wild-type form of the protein, or can encode variants thereof, including both agonists and antagonists, as well as antisense constructs or RNAi constructs. In preferred embodiments, the expression of the transgene is restricted to specific subsets of cells, tissues or developmental stages utilizing, for example, cis-acting sequences that control expression in the desired pattern. Toward this end, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo, and such techniques are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject proteins. For example, excision of a target sequence which interferes with the expression of a recombinant gene, such as one which encodes an antagonistic variant or an antisense transcript, can be designed to activate expression of that gene. This interference with expression of the protein can result from a variety of mechanisms, such as spatial separation of the gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allows for promoter driven transcriptional activation.

In an illustrative embodiment, either the cre/loxP recombinase system of bacteriophage P1 (Lakso et al. (1992) *PNAS* 89: 6232–6236; Orban et al. (1992) *PNAS* 89: 6861–6865) or the FLP recombinase system of *Saccharomyces cerevisiae* (O'Gorman et al. (1991) *Science* 251: 1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259: 1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element.

Use of the cre/loxP recombinase system to regulate expression of a recombinant protein requires the construction of a transgenic animal containing transgenes encoding both the Cre recombinase and the subject protein. Animals containing both the Cre recombinase and a recombinant gene of interest can be provided through the construction of "double" transgenic animals. A convenient method for providing such animals is to mate two transgenic animals each containing a transgene. However, other methods can be readily employed to avoid the need for natural matings.

In a related aspect, expression of conditional transgenes can be induced by methods wherein a gene encoding the trans-activating protein, e.g. a recombinase, is delivered to the tissue and caused to be expressed, such as in a cell-type specific manner. By this method, a transgene could remain silent into adulthood until "turned on" by the introduction of the trans-activator. In the case of an ATR polypeptide, this may be especially useful. Given that one particularly important effect of misregulation of ATR is in dis-regulated cell proliferation (e.g., various forms of cancer), it may be particularly useful to examine adult, as well as tissue specific, ATR transgenic animals.

In an exemplary embodiment, the "transgenic non-human animals" of the invention are produced by introducing transgenes into the germline of the non-human animal. Embryonic target cells at various developmental stages can be used to introduce transgenes. Different methods are used depending on the stage of development of the embryonic target cell. The zygote is a good target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82: 4438–4442). As a consequence, all cells of the transgenic non-human animal will carry the incorporated transgene. This will in general also be reflected in the efficient transmission of the transgene to offspring of the founder since 50% of the germ cells will harbor the transgene.

Retroviral infection can also be used to introduce transgenes into a non-human animal. The developing non-human embryo can be cultured in vitro to the blastocyst stage. During this time, the blastomeres can be targets for retroviral infection (Jaenich, R. (1976) *PNAS* 73: 1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82: 6927–6931; Van der Putten et al. (1985) *PNAS* 82: 6148–6152). Transfection is easily and efficiently obtained by culturing the blastomeres on a monolayer of virus-producing cells (Van der Putten, supra; Stewart et al. (1987) *EMBO J.* 6: 383–388). Alternatively, infection can be performed at a later stage. Virus or virus-producing cells can be injected into the blastocoele (Jahner et al. (1982) *Nature* 298: 623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonic stem cell (ES). ES cells are obtained from pre-implantation embryos cultured in vitro and fused with embryos (Evans et al. (1981) *Nature* 292: 154–156; Bradley et al. (1984) *Nature* 309: 255–258; Gossler et al. (1986) *PNAS* 83: 9065–9069; and Robertson et al. (1986) *Nature* 322: 445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240: 1468–1474.

Methods of making knock-out or disruption transgenic animals are also generally known. See, for example, *Manipulating the Mouse Embryo*, (Cold Spring Harbor Laboratory Press, Cold Spring Harbor, N.Y., 1986). Recombinase dependent knockouts can also be generated, e.g. by homologous recombination to insert recombinase target sequences flanking portions of an endogenous gene, such that tissue specific and/or temporal control of inactivation can be controlled as above.

Methods for making transgenic fish and amphibians are well known in the art. Exemplary methods are summarized in the following publications: Hartley et al. (2002) *PNAS* 99: 1377–1382; Werdien et al. (2001) *Nucleic Acids Research* 29: E53; Breckenridge et al. (2001) *Developmental Biology* 232: 191–203; Wheeler et al. (2000) *Current Biology* 10: 849–852; Jonak (2000) *Mol Reprod Dev* 56: 298–300; Offield et al. (2000) *Development* 127: 1789–1797; Sparrow et al. (2000) *Nucleic Acids Research* 28: E12; Marsh-Armstrong et al. (1999) *PNAS* 96: 14389–14393; Bronchain et al. (1999) *Current Biology* 9: 1195–1198; Amaya and Kroll (1999) *Methods Mol Biol* 97: 393–414; Kroll and Amaya (1996) *Development* 122: 3173–3183; Gaiano et al. (1996) *PNAS* 93: 7777–7782; Morgan et al. (1996) *PNAS* 93: 2801–2806; Lee et al. (2002) *Nature Biotechnology* 20: 795–799). Further methods and guidance in the making of transgenic amphibians and fish can be found on the following websites: www.stjude.org/departments/mead.htm; www.xenbase.org/genetics/training.html; faculty.virginia.edu/xtropicalis; www.welc.cam.ac.uk/~ea3/The.Amaya.Lab.Homepage.html.

(v) Method of Screening

Furthermore, by making available purified and recombinant polypeptides, the present invention facilitates the development of assays which can be used to screen for agents, including ATR variants, which are either agonists or antagonists of one or more of the activities of an ATR polypeptide. Exemplary agents (e.g., a single agent, a combination of two or more agents, a library of agents) include nucleic acids, peptides, proteins, antibodies, antisense RNAs, RNAi constructs, chemical compounds, and small organic molecules. Activities which may be modulated (increased or decreased) by said one or more agents include (1) the ability to phosphorylate a Chk1 protein, (2) the ability to bind single-stranded DNA, (3) the ability to bind double-stranded DNA, (4) the ability to induce cell cycle delay in response to DNA damage, and/or (5) the ability to induce cell cycle delay in response to a DNA replication block. A variety of assay formats will suffice and, in light of the present inventions, will be comprehended by the skilled artisan. In one particular embodiment, one of skill in the art will recognize that the present invention for the first time demonstrates that Chk1 is a direct substrate for the ATR kinase, and that this activity is evolutionarily conserved. Accordingly, the present invention provides methods of screening for agents which modulate the phosphorylation of a Chk1 protein by an ATR polypeptide.

In many drug screening programs which test libraries of compounds and natural extracts, high throughput assays are desirable in order to maximize the number of agents surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test agent. Cell free systems include purely in vitro systems (preparations of proteins and agents combined in a test tube, Petri dish, etc.), as well as cell free systems such as those prepared from egg extracts. Exemplary egg extracts can be prepared from amphibians, clams, sea urchins, and the like. Although egg extracts can theoretically be prepared from any species, preferred egg extracts are prepared from species whose eggs are large (i.e., contain a large amount of cytoplasm—and thus from which a relatively large amount of extract can be readily prepared) and easily obtained. Moreover, the effects of cellular toxicity and/or bioavailability of the test agents can be generally ignored in such a system, the assay instead being focused primarily on the effect of the agent.

In an exemplary screening assay of the present invention, the agent of interest (e.g., an individual agent, a combination of two or more agents, a library of agents) is contacted with a preparation comprising an ATR polypeptide and a Chk1 polypeptide. The preparation is contacted with said agent prior to phosphorylation of Chk1 by ATR, and the ability of the agent to modulate (either increase or decrease) the phosphorylation of Chk1 by ATR is measured and compared to the wildtype phosphorylation of Chk1 by ATR (as, for example, in a control preparation which is not contacted with the agent). The efficacy of the agent can be assessed by generating dose response curves from data obtained using various concentrations of the test agent. Moreover, a control assay can also be performed to provide a baseline for comparison.

In another exemplary screening assay of the present invention, the agent of interest (e.g., an individual agent, a combination of two or more agents, a library of agents) is contacted with a preparation comprising an ATR polypeptide. The preparation comprising said ATR polypeptide may be any cell-free system such as an egg extract. The ability of said agent to modulate (either increase or decrease) at least one activity of an ATR polypeptide is assessed in comparison to a preparation comprising the ATR polypeptide which is not contacted with said agent. Examples of activities which may be modulated by said agent and which may be assayed in the present methods include phosphorylation of Xchk1, phosphorylation of another substrate in the preparation, binding of single-stranded DNA, binding of double-stranded DNA, ability to induce cell cycle delay in response to DNA damage, and/or the ability to induce cell cycle delay in response to a DNA replication block.

In any of the foregoing screening methods, the invention further contemplates that screening assays may be performed to identify agents which modulate (either increase or decrease) an activity of either a wildtype ATR polypeptide or a variant ATR polypeptide (e.g., a mutant form of the polypeptide which may have compromised activity—either increased or decreased). For example, preparations of variant ATR polypeptides may be contacted with one or more agents. The invention further contemplates methods of identifying agents which modulate the phosphorylation of a variant Chk1 polypeptide by an ATR polypeptide, as well as agents which modulate ATR activity in a cell containing a mutation in another protein involved in sensing or responding to DNA damage and/or a DNA replication block (e.g., ATM, Chk1, Chk2, Cds1, claspin, etc). The invention further contemplates methods of identifying agents which modulate ATR activity in a cell containing a mutation in another protein involved in regulation of the cell cycle (e.g., Cdc2, Cdc25, p53, BRCA1, etc.). In yet another embodiment, the invention contemplates that such screening assays may be performed in preparations which have been immunodepleted of ATR or Chk1. For example, an ATR depleted preparation may be used to screen for agents which can replace, in whole or in part, one or more functions of an ATR polypeptide.

In addition to cell-free assays, such as described above, the invention further contemplates the generation of cell-based assays for identifying agents which modulate (increase or decrease) one or more activities of an ATR polypeptide. Such cell based assays can employ any cell-type including cells which are sensitive to ATR mediated cell cycle delay. The invention contemplates the use of cells which comprise a wildtype ATR polypeptide, as well as cells comprising a variant ATR polypeptide. The invention further contemplates the use of cells comprising mutations in one or more other proteins, as described in detail above.

One class of agents which may modulate at least one activity of an ATR polypeptide are agents which bind (either directly or indirectly) to an ATR polypeptide. Accordingly, the present invention contemplates screening for agents which bind to an ATR polypeptide. Many well known methods exist in the art for assessing protein-protein, protein-nucleic acid, protein-antibody, and protein-chemical/small molecule interaction. Exemplary methods include two-hybrid screens, affinity chromatography, immunoprecipitation, and the like. One of skill in the art can select amongst commonly used methods for detecting the interaction of an ATR polypeptide with an agent including proteins, nucleic acids, small molecule, chemical compounds, antibodies, etc.

(vi) Methods of Administration of Proteins, Chemical Compounds and Pharmaceutical Compositions of Any Agent An agent identified by the subject methods has many potential uses. Such an agent may be a nucleic acid, peptide, polypeptide, RNAi construct, chemical compound, small organic molecule, antisense RNA, antibody, or the like. Furthermore, such an agent may either increase or decrease an activity of an ATR polypeptide. An exemplary activity of an ATR polypeptide which is modulated (either increased or decreased) by an agent identified by the subject methods includes the phosphorylation of a Chk1 protein by ATR. Additional preferred activities which may be modulated (either increased or decreased) by an agent identified by the subject methods include (1) the ability to bind single-stranded DNA, (2) the ability to bind double-stranded DNA, (3) the ability to induce cell cycle delay in response to DNA damage, and/or (4) the ability to induce cell cycle delay in response to a DNA replication block. Furthermore, the invention contemplates that the present methods may be used to identify combinations of agents (e.g., two or more agents) which can modulate at least one activity of an ATR polypeptide. Such agents may act additively or synergistically. In one embodiment, neither agent alone modulate at least one activity of an ATR polypeptide, however, the agents together modulate an activity of an ATR polypeptide. In another embodiment, each agent alone has some effect an activity of an ATR polypeptide, and the agents together act synergistically or additively to modulate an activity of an ATR polypeptide.

Agents identified by the methods of the present invention may be useful in a therapeutic context. For example, normal function of ATR, and other ATR related proteins (such as ATM), is required to maintain proper genomic stability. Conditions of unregulated cell proliferation, including various forms of cancer, may result from failure of proper cell cycle arrest in response to DNA damage. Accordingly, agents which modulate the activity of ATR, have significant utility in the treatment of diseases associated with unregulated cell proliferation including all forms of cancer. The invention contemplates that such agents may be used alone, or may be administered as part of a therapeutic regimen in combination with other agents such as traditional chemotherapeutics, radiation therapy, holistic medicine, and the like.

However, cell cycle checkpoints can also represent an impediment to the treatment of many proliferative disorders including cancer. For example, one of the goals of treating cancerous tissue with damaging agents such as chemotherapeutics and radiation is to induce the cells to die. However, the induction of cell cycle checkpoints in response to the damaging agents sometimes lessens the effectiveness of the treatment. Accordingly, the present invention further contemplates the therapeutic use of agents which decrease an ATR activity.

The one or more agents identified by the subject methods may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the one or more agents. The use of such media for pharmaceutically active substances is known in the art. Except insofar as any conventional media or agent is incompatible with the activity of a particular agent or combination of agents, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of an agent at a particular target site.

The agents identified using the methods of the present invention may be given orally, parenterally, topically, or rectally. They are of course given by forms suitable for each administration route. For example, they are administered in tablets or capsule form, by injection, inhalation, eye lotion, ointment, suppository, controlled release patch, or infusion.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the animal's system and, thus, is subject to metabolism and other like processes, for example, subcutaneous administration.

One or more agents may be administered to humans and other animals by any suitable route of administration, including orally, nasally, as by, for example, a spray, rectally, intravaginally, parenterally, intracisternally and topically, as by powders, ointments or drops, including buccally and sublingually.

Actual dosage levels of the one or more agents administered in the methods of the present invention may be varied so as to obtain an amount of the active ingredient which is effective to achieve a response in an animal. The actual effective amount can be determined by one of skill in the art using routine experimentation and may vary by mode of administration. Further, the effective amount may vary according to a variety of factors include the size, age and gender of the individual being treated. Additionally the severity of the condition being treated, as well as the presence or absence of other components to the individuals treatment regimen will influence the actual dosage.

The effective amount or dosage level will depend upon a variety of factors including the activity of the particular one or more agents employed, the route of administration, the time of administration, the rate of excretion of the particular agents being employed, the duration of the treatment, other drugs, compounds and/or materials used in combination with the particular agents employed, the age, sex, weight, condition, general health and prior medical history of the animal, and like factors well known in the medical arts.

The one or more agents identified by the methods of the present invention can be administered as such or in admixtures with pharmaceutically acceptable and/or sterile carriers and can also be administered in conjunction with other compounds. Such additional compounds may include factors known to influence the proliferation, differentiation or migration of a particular cell. These additional compounds may be administered sequentially to or simultaneously with the agents being screened by the methods of the present invention. By administering compounds known to influence cell behavior, the invention further contemplates identifying agents which may not alone be sufficient to influence cell behavior. However, such agents may be capable of acting additively or synergistically with compounds known to modulate cell behavior.

Agents screened by the methods of the present invention can be administered alone, or can be administered as a pharmaceutical formulation (composition). Said agents may be formulated for administration in any convenient way for use in human or veterinary medicine. In certain embodiments, the agents included in the pharmaceutical preparation may be active themselves, or may be a prodrug, e.g., capable of being converted to an active compound in a physiological setting.

Thus, another aspect of the present invention provides pharmaceutically acceptable compositions comprising an effective amount of one or more agents, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject agents may be simply dissolved or suspended in sterile water. In certain embodiments, the pharmaceutical preparation is non-pyrogenic, i.e., does not elevate the body temperature of a patient.

The phrase "effective amount" as used herein means that amount of one or more agent, material, or composition comprising one or more agents of the present invention which is effective for producing some desired effect in an animal.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, one or more agents may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

The pharmaceutically acceptable salts of the agents include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the one or more agents may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association an agent with the carrier and, optionally, one or more accessory ingredients. In general, the formulations are prepared by uniformly and intimately bringing into association an agent of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate; with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as $\alpha$-, $\beta$- and $\gamma$-cyclodextrin, dimethyl-$\beta$ cyclodextrin and 2-hydroxypropyl-$\beta$-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the agents.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the agents in the proper medium. Absorption enhancers can also be used to increase the flux of the agents across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of an agent, it is desirable to slow the absorption of the agent from subcutaneous or intramuscular injection. This may be accomplished by the use of a liquid suspension of crystalline or amorphous material having poor water solubility. The rate of absorption of the agent then depends upon its rate of dissolution which, in turn, may depend upon crystal size and crystalline form. Alternatively, delayed absorption of a parenterally administered agent form is accomplished by dissolving or suspending the agent in an oil vehicle.

Injectable depot forms are made by forming microencapsule matrices of the subject compounds in biodegradable polymers such as polylactide-polyglycolide. Depending on the ratio of agent to polymer, and the nature of the particular polymer employed, the rate of agent release can be controlled. Examples of other biodegradable polymers include poly(orthoesters) and poly(anhydrides). Depot injectable formulations are also prepared by entrapping the agent in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Oreg., U.S.A., 1977).

EXEMPLIFICATION

The invention now being generally described, it will be more readily understood by reference to the following examples which are included merely for purposes of illustration of certain aspects and embodiments of the present invention, and are not intended to limit the invention.

Example 1

Isolation of *Xenopus* ATR

Given the utility of *Xenopus* eggs and egg extracts to investigate the cell cycle and to potentially identify additional components which help regulate the cell cycle, the isolation and characterization of *Xenopus* nucleic acids and proteins which correspond to cell cycle proteins was an important goal. We isolated a nucleic acid encoding a *Xenopus laevis* ATR (Xatr) using a degenerate polymerase chain reaction (PCR) approach. Xatr nucleic acid sequences are provided in SEQ ID NO: 1 and 3. SEQ ID NO: 1 and 3 encode a 301 kD polypeptide of 2654 amino acids. The amino acid sequence of this Xatr polypeptide is provided in SEQ ID NO: 2.

Figure 1:
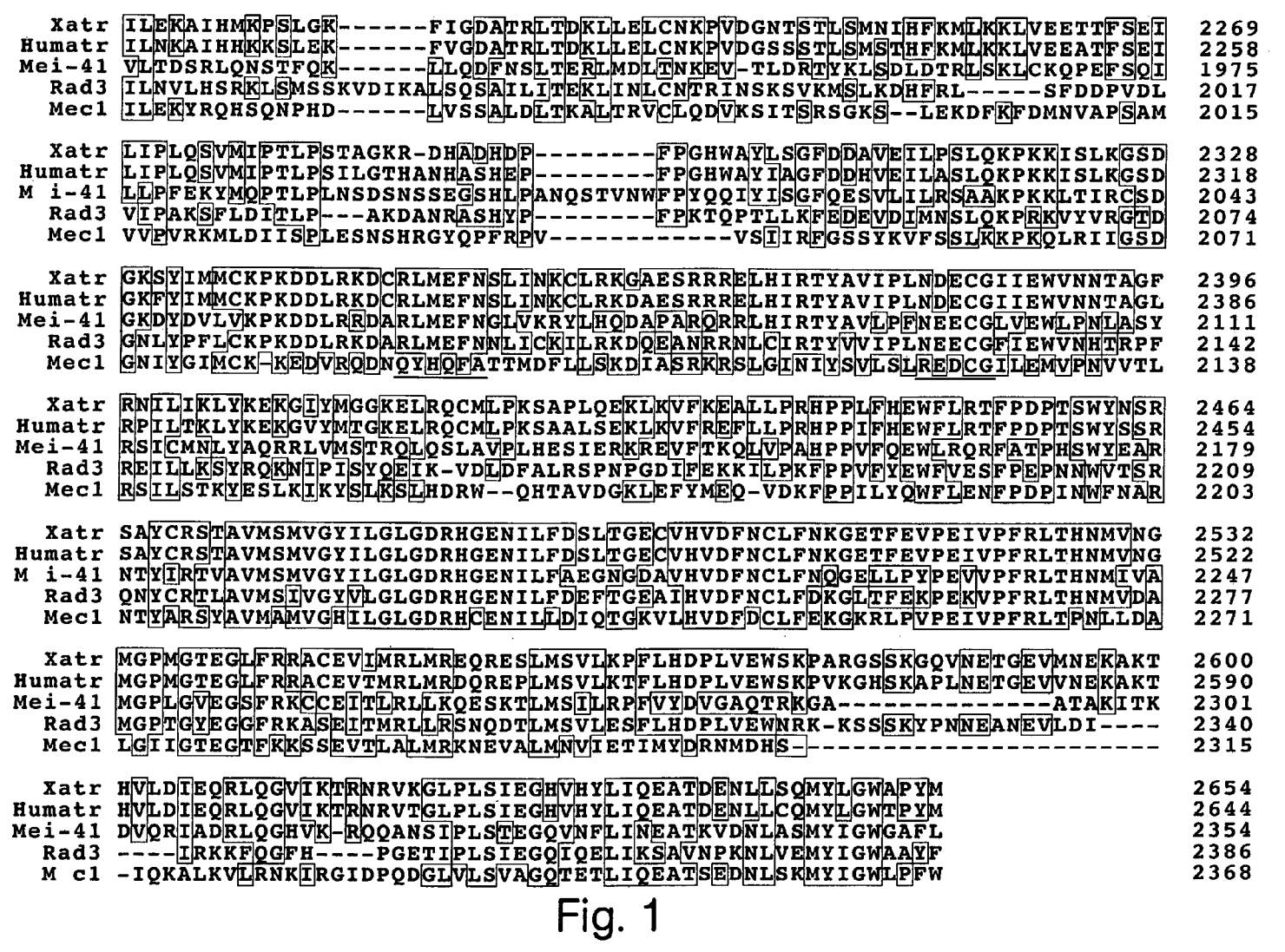

Xatr (SEQ ID NO: 2) is most closely related to human ATR and is approximately 70% identical across the entire length of the protein. Xatr is also related to ATR homologs identified in invertebrates and fungi and is 29%, 28%, and 23% identical to *Drosophila* Mei-41, *S. pombe* Rad3, and *S. cerevisiae* Mec1, respectively. FIG. 1 provides an alignment of the C-terminal region of Xatr, human ATR, Mei-41, Rad3, and Mec1. We note that this region, which contains the kinase domain of the protein, is the most conserved region of the protein across species. Additionally, the kinase region of the protein is characteristic of phosphoinositide kinase (PIK)-related protein kinases which include ATR, ATM, and DNA-PKcs, as well as their yeast homologs. All of these PIK-related protein kinases play important roles in mediating cell cycle checkpoints in response to various forms of DNA damage including ionizing radiation, UV radiation, replication blocks, and double-stranded breaks.

METHODS: A 140 basepair fragment of a cDNA encoding Xatr was isolated by PCR using the degenerate oligonucleotides CCGGAATTGA(T/C)GCI(A/C)GI(C/T)TIATGG (SEQ ID NO: 4) and CGCGGATCCICC(A/G)CA(C/T)TCITC(A/G)TT (SEQ ID NO: 5). The oligonucleotides were designed based on conserved regions of ATR homologs which are indicated by bars on the alignment presented in FIG. 1. The PCR reactions contained *Xenopus* oocyte cDNA as a template, 50 pmole of degenerate oligonucleotides, 200 μM of dNTPs, 0.5 units of Taq polymerase, and the reactions were carried out in the buffer supplied by the manufacturer (GIBCO BRL). PCR reactions were heated at 94° C. for 2 minutes, followed by 30 cycles of amplification. Each cycle consisted of segments of 94° C. for 1 minute, 45° C. for 1 minute, and 72° C. for 1 minute. An extra 10 minutes was added to the final 72° C. extension step.

The 140 basepair fragment isolated by degenerate PCR was used as a probe to screen a *Xenopus* oocyte cDNA library (Mueller et al. (1995) *Mol. Biol Cell* 6: 119–134). A 3 kilobase clone was isolated that included the C-terminal domain and 3' untranslated sequence. Using the 5' most 150 basepair fragment of the 3 kilobase clone as a probe to rescreen the same library, a 1.1 kilobase overlapping clone was isolated. The 5' most 150 basepair fragment of the 1.1 kilobase clone was radioactively labeled, and used as a probe to screen a second *Xenopus* oocyte library (Kinoshita et al. (1995) *Cell* 83: 621–630). Screening of the second library identified a 4 kilobase clone which overlapped the 1.1 kilobase clone but not the 3 kilobase clone. Additional 5' sequence was identified using 5' RACE (GIBCO BRL). The nucleic acid sequence corresponding to Xatr is depicted in SEQ ID NO: 3, and this sequence includes 5' and 3' untranslated sequence. The coding sequence of Xatr is present in SEQ ID NO: 1. The Xatr nucleic acid sequence encodes a protein comprising the amino acid sequence presented in SEQ ID NO: 2.

Example 2

Preparation of Xatr Antibodies

In order to facilitate further characterization of ATR proteins, we generated polyclonal antibodies using fragments of the Xatr protein. One of two fragments were used as the antigen: either a His tagged fusion protein wherein 6 copies of a His tag were fused to amino acids residues 2351–2654 of the Xatr depicted in SEQ ID NO: 2, or a 14 amino acid peptide consisting of amino acid residues 1617–1630 of SEQ ID NO: 2 (residues 1617–1630=EKT-NPKPGTRGEPK, SEQ ID NO: 11).

FIG. 2 shows immunoblot analysis of endogenous Xatr and recombinantly produced GST-Xatr. Polyclonal antibody against His6-Xatr(2351–2654) was immunoreactive with Xatr endogenously expressed in *Xenopus* egg extracts (lane 1) and purified GST-Xatr which was recombinantly produced in yeast (lane 2). We note that the protein recognized in lane 2 migrates approximately 30 kD larger on an SDS-PAGE gel than endogenous Xatr. This is consistent with the fact that the recombinant protein is fused to GST, and provides additional support that the identified cDNA encodes a full length protein.

METHODS: An NdeI-EcoRI restriction fragment encoding amino acids 2351–2654 of Xatr was amplified using standard PCR methods, and cloned into pET3 (Novagen). The His6-Xatr(2351–2654) protein encoded by this plasmid was expressed in *E.coli*, isolated using nickel agarose, further purified using SDS-PAGE, and used for the production of polyclonal antibodies. Production of polyclonal antibodies was by standard methods, and was performed at a commercial facility (Covance Research Products).

Production of polyclonal antibodies against the internal peptide consisting of amino acid residues 1617–1630 was by standard methods, and these antibodies were generated at a second commercial facility (Zymed Laboratories).

Example 3

Xatr Binds Both Single-stranded and Double Stranded DNA

One characteristic of PIK-related protein kinases is that they appear to associate, either directly or indirectly, with DNA and/or chromosomes (Smith and Jackson (1999) *Genes & Development* 13: 916–934; Keegan et al. (1996) *Genes & Development* 10: 2423–2437; Smith et al. (1999) *PNAS* 96: 11134–11139; Suzuki et al. (1999) *Journal of Biological Chemistry* 274: 25571–25575). Without wishing to by bound by theory, such an association may provide a mechanism for sensing or detecting DNA damage.

Figure 3A:
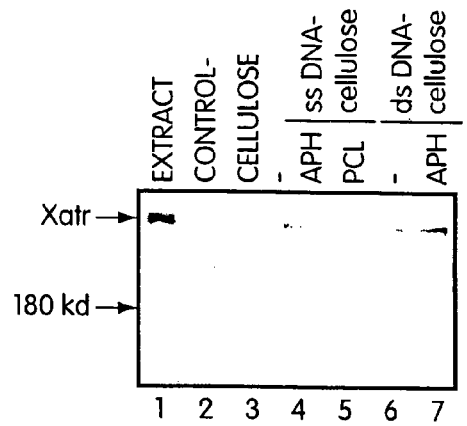
FIG. 3A shows that Xatr binds to both single and double-stranded DNA cellulose. Control cellulose (lane 2), single stranded DNA-cellulose (lanes 3–5), or double-stranded DNA cellulose (lanes 6–7) were incubated with 50 µL of cytosol in the presence of APH (lanes 4 and 7), in the presence of protease inhibitors (PCL—lane 5), or in the absence of either APH or PCL (lanes 3 and 6). Note that Xatr binds both single and double stranded DNA in either the presence or absence of APH or PCL.

In order to functionally characterize Xatr, we examined the association of Xatr with both single and double-stranded DNA in *Xenopus* egg extracts, under a variety of conditions. FIG. 3A demonstrates that Xatr binds both single-stranded DNA cellulose (lanes 3–5) and double-stranded DNA cellulose (lanes 6–7). Additionally, we note that the interaction of Xatr with DNA occurs in the presence or the absence of either the DNA polymerase inhibitor aphidicolin (APH) or protease inhibitors (PCL). Briefly, control cellulose, single-stranded DNA cellulose, or double-stranded DNA cellulose were incubated with 50 μL of cytosol in the presence or absence of APH or PCL. Washed cellulose beads were boiled in gel loading buffer, and half of this was subjected to immunoblot analysis using an Xatr polyclonal antibody prepared in Example 1.

Figure 3B:
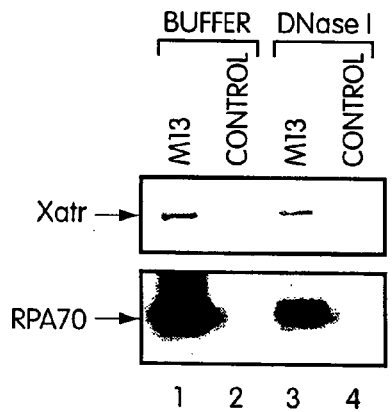
FIG. 3B shows DNase I digestion partially releases Xatr from DNA (compare lane 1 and lane 3 of the top panel). As a control, DNase I digestion similarly releases RPA70 which is known to tightly associate with DNA (compare lane 1 and lane 3 of the bottom panel).

FIG. 3B demonstrates that the interaction of Xatr with DNA cellulose was reduced upon treatment with DNase I (compare lane 1 and lane 3). We also note that the interaction of RPA70, which is known to tightly bind to both single and double stranded DNA (Adachi and Laemmli (1992) *Journal of Cell Biology* 119: 1–15), is reduced following DNaseI treatment (compare lane 1 and lane 3). These results indicate that DNA digestion partially releases Xatr from the DNA.

Figure 3C:
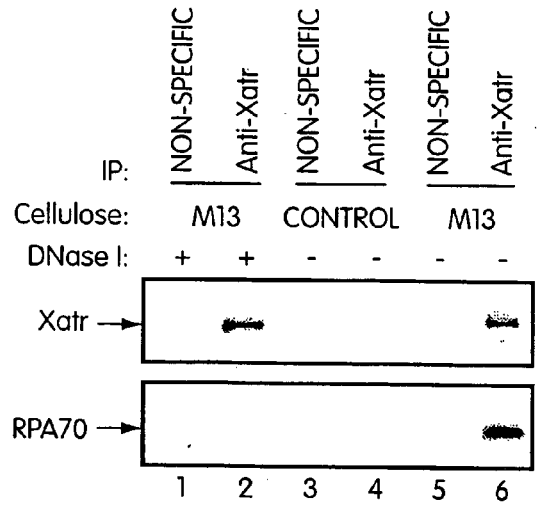
FIG. 3C shows that DNA can mediate the coimmunoprecipitation of two proteins which both specifically associate with DNA. Proteins associated with single-stranded DNA cellulose (lanes 1, 2, 5, 6) were treated with either DNase I (lanes 1 and 2) or with NP-40 (lanes 3–6). Following treatment with NP-40, but not with DNase I, Xatr and RPA70 coimmunoprecipitated (compare lane 2 and lane 6).

Finally, FIG. 3C provides further evidence demonstrating the interaction of Xatr with DNA. This experiment is based on the fact that DNA interacts with cellulose by adsorption, and thus DNA can be released from cellulose using conditions which do not disrupt the association of tightly bound proteins with the DNA itself. Such tightly bound proteins may not only remain associated with DNA, but may also co-immunoprecipitate other tightly bound proteins. FIG. 3C demonstrates that RPA70, which is known to specifically associate with single and double stranded DNA, coimmunoprecipitated with Xatr following treatment with the detergent NP-40 (lane 6). However, RPA70 and Xatr do not coimmunoprecipitate following treatment with DNase I (lane 2). Briefly, proteins associated with single-stranded DNA cellulose (lanes 1, 2, 5, 6) were released with either DNase I (lanes 1 and 2) or NP-40 (lanes 3–6). The released proteins were incubated with either anti-Xatr antibodies (as provided in Example 1) or control antibodies. The immunoprecipitates were immunoblotted with either Xatr antibodies (top panel) or with RPA70 antibodies (bottom panel).

METHODS: *Xenopus* cytostatic factor (CSF)-arrested egg extracts were prepared from unactivated eggs in M-phase using standard methods (Murray (1991) *Methods Cell Biology* 36: 581–605). $CaCl_2$ was added to promote interphase, and interphase cytosol was prepared via centrifugation for 1½ hours at 4° C. at 260,000 g. Where necessary, extracts were arrested in interphase by the addition of 100 μg/mL cycloheximide.

Preparation of DNA cellulose: M13 DNA (single-stranded DNA) was prepared according to the manufacturers instructions (Amersham). pBS plasmids (pBluescript—double stranded DNA) were prepared by a standard alkaline lysis procedure. 1 mg of M13 DNA or pBluescript DNA in 1 mL of TE buffer (10 mM Tris-HCL, 1 mM EDTA at pH 8.0) was incubated with 0.3 grams of cellulose for 5 minutes at 23° C. Following incubation, the preparation was lyophilized for 18 hours. The resulting lyophilized powder was resuspended in 20 volumes of TE, incubated at 4° C. for 24 hours, washed with TE, and frozen at −70° C. until use. Naked control cellulose was prepared under the same conditions, however, the addition of either single or double stranded DNA was omitted.

Binding of Xatr to DNA cellulose: 25–100 μL of DNA cellose was incubated with with 50–500 μL of interphase egg cytosol for 40 minutes at 23° C. During the incubation, the preparation was rocked constantly. Following incubation, the preparation was centrifuged, and the cytosol supernatant removed. The cellulose beads were washed with 1 mL wash buffer (10 mM HEPES at pH 7.5, 150 mM NaCl, 0.05% NP-40, 30 mM β-glycerolphosphate, 0.1 mM $Na_3VO_4$, 0.1 mM phenylmethylsulfonyl fluoride, and 10 μg/mL each of pepstatin, chymostatin, and leupeptin).

Where indicated, washed beads were further incubated with DNase I for 10 minutes at 23° C.

Example 4

Xatr Kinase Activity

Figure 3D:
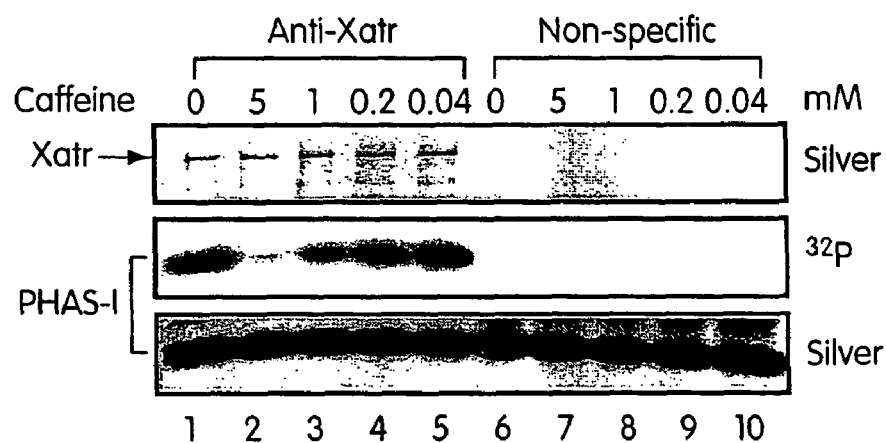
FIG. 3D shows that Xatr has kinase activity, and can phosphorylate the substrate PHAS-I (lane 1—middle panel). Additionally, the kinase activity of Xatr is sensitive to caffeine (lanes 2–5—middle panel).

Given the conservation of the PIK-related kinase domain among ATR homologs, we characterized the kinase activity of Xatr. Xatr was immunoprecipitated from *Xenopus* egg extracts using an anti-Xatr antibody (as described in Example 1). FIG. 3D (lane 1) shows that these immunoprecipitates phosphorylated a model substrate protein (PHAS-I) in vitro.

To further assess the relationship between Xatr and other PIK-related kinases, we next assessed the effects of caffeine on the kinase activity of Xatr. Interestingly, the kinase activity of ATR, ATM and TOR are sensitive to caffeine (Blasina et al. (1999) *Current Biology* 9: 1135–1138; Hall-Jackson et al. (1999) *Oncogene* 18: 6707–6713; Sarkaria et al. (1999) *Cancer Research* 59: 4375–4382). FIG. 3D shows that the kinase activity of Xatr is also affected by caffeine. Briefly, kinase assays were performed by incubating anti-Xatr immunoprecipitates (lanes 1–5) or control immunoprecipitates (lanes 6–10) with the model substrate PHAS-I, in the presence of 0 (lanes 1 and 6), 0.04 mM (lanes 5 and 10), 0.2 mM (lanes 4 and 9), 1 mM (lanes 3 and 8) or 5 mM (lanes 2 and 7) caffeine. Proteins were subjected to SDS-PAGE and visualized by silver staining (bottom panel). Phosphorylation of PHAS-I was detected by autoradiography (middle panel). Note the significant decrease in phosphorylation of PHAS-I with increasing concentrations of caffeine (compare lanes 5, 4, 3 and 2).

In addition, we note that the phosphorylation of Xchk1 in response to unreplicated DNA was inhibited in the presence of caffeine. *Xenopus* egg extracts were treated with aphidicolin to block DNA replication, and the phosphorylation of Xchk1 was measured in the presence of increasing concentrations of caffeine. Caffeine inhibited the phosphorylation of Xchk1, and this response occurred at approximately the same half-maximal dose as that observed for the inhibition of the kinase activity of Xatr shown in FIG. 3D. The similar sensitivities to caffeine observed for both Xatr and Xchk1 will be addressed in greater detail in subsequent examples.

Figure 3E:
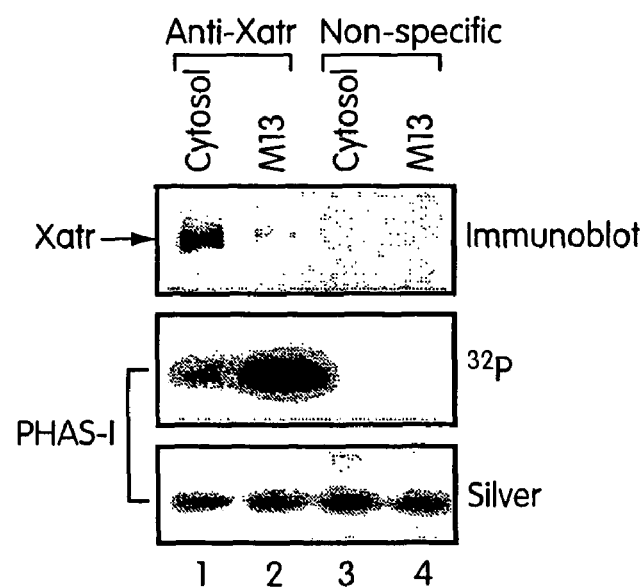
FIG. 3E shows that the kinase activity of Xatr increases following pre-incubation with DNA-cellulose (compare lanes 1 and 2—middle panel). Xatr was immunoprecipitated from either egg cytosol, or from egg cytosol containing DNA-cellulose, and the kinase activity of Xatr was measured by assaying the phosphorylation of PHAS-I.

We had shown that Xatr binds to both single-stranded and double stranded DNA, and we now have shown that Xatr has kinase activity. FIG. 3E demonstrated that the association of Xatr with DNA increases its kinase activity. Egg cytosol was incubated with DNA cellulose to facilitate binding of Xatr to the DNA-cellulose. This preparation was digested with DNase I and immunoprecipitated with an anti-Xatr antibody. As shown in FIG. 3E, Xatr which was pre-associated with DNA displayed an approximately 10–20 fold higher kinase activated (compare lane 1 and 2). Briefly, Xatr was immunoprecipitated from cytosol (lane 1) or from DNA cellulose-associated proteins treated with DNaseI (lane 2), and the kinase activity of the immunoprecipitated Xatr was assessed by measuring phosphorylation of PHAS-I (middle panel). The bottom panel shows silver staining of the SDS-PAGE gel which demonstrates that equivalent amounts of protein were loaded in every lane. We note that increased Xatr kinase activity was observed when Xatr was incubated with either single-stranded or double stranded DNA.

METHODS: Polyclonal antibodies generated against an Xatr peptide (EKTNPKPGTRGEPK, SEQ ID NO: 11), as shown in Example 1, were used to immunoprecipitate Xatr. Immunoprecipitation and kinase assays were performed using standard methods, and as previously shown (Guo and Dunphy (2000) Mol. Biol Cell 11: 1535–1546).

Example 5

Immunodepletion of Xatr

Previous work has demonstrated that Xchk1 is phosphorylated in response to UV damage and/or DNA replication blocks (Kumagi et al. (1998) *Journal of Cell Biology* 142: 1559–1569), and ATR family members are believed to act upstream of Chk1 family members in a variety of species. However, the exact nature of the relationship between ATR and Chk1 proteins remains unclear. Additionally, both Xatr and Xchk1 respond to caffeine with similar kinetics (see Example 4), providing further evidence for some interaction between these proteins. Given previous work in this field, as well as the evidence provided herein, we performed experiments to better understand the relationship between Xchk1 and Xatr.

Figure 4A:
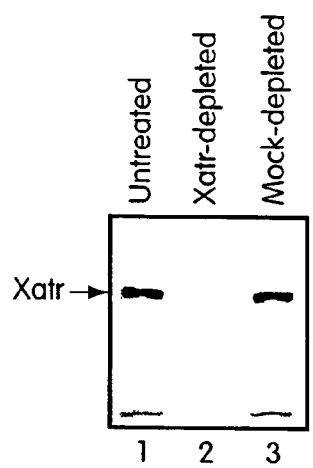
FIG. 4A shows that incubation of egg extracts with an anti-Xatr antibody made against His6-Xatr(2351–2654) successfully immunodepletes Xatr from those egg extracts (compare lane 1 and lane 2).

FIG. 4A showed that Xatr can be successfully immunodepleted from egg extracts (compare lanes 1 and 2) using an anti-Xatr antibody which we previously prepared [against His6-Xatr(2351–2654)]. The ability to immunodeplete Xatr from egg extracts allowed us to examine the phosphorylation of Xchk1 in response to DNA damage in the presence and absence of Xatr.

Figure 4B:
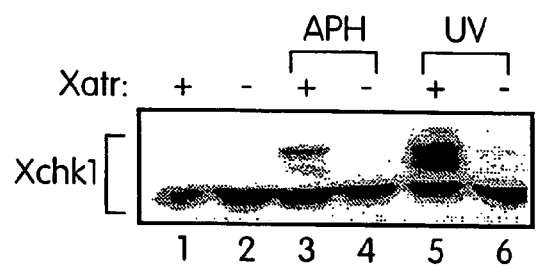
FIG. 4B shows that, Xchk1 is not phosphorylated in response to DNA damage or a DNA replication block in Xatr immunodepleted egg extracts. In egg extracts which express Xatr protein (lanes 1, 3, and 6), Xchk1 is phosphorylated in response to DNA replication blocks (as when the extract is treated with APH—lane 3) or UV damage (lane 5). Phosphorylation of Xchk1 in response to such treatments is not observed in Xatr immunodepleted egg extracts (lane 4 and lane 6).

FIG. 4B showed that Xchk1 was not phosphorylated in response to DNA damage or a DNA replication block in Xatr immunodepleted egg extracts. Firstly, we have confirmed previous results which indicate that in egg extracts which express Xatr protein (lanes 1, 3, and 6), Xchk1 is phosphorylated in response to either a DNA replication block (as when the extract is treated with APH—lane 3) or UV damage (lane 5). However, the phosphorylation of Xchk1 in response to such treatments was not observed in Xatr immunodepleted egg extracts (lane 4 and lane 6). Briefly, Xatr immunodepleted extracts (lanes 2, 4, 6) or mock-depleted extracts (containing Xatr—lanes 1, 3, 5) were incubated at 23° C. for 100 minutes either alone (lanes 1 and 2), in the presence of aphidicolin (APH—lanes 3 and 4), or in the presence of UV light (UV—lanes 5 and 6). Phosphorylation of Xchk1 in response to DNA damage is not observed in Xatr immunodepleted extracts.

Figure 4C:
FIG. 4C shows that the effects of immunodepletion of Xatr are specific. The phosphorylation of Xcdc1 in egg extracts in response to the presence of double stranded DNA ends is not effected by immunodepletion of Xatr from those egg extracts (compare lanes 2–5).

To address the specificity of the effect of Xatr immunodepletion, we examined phosphorylation of the *Xenopus* homolog of Cds1, Xcds1. We have previously shown that Xcds1 responds to different types of DNA damage from those which elicit phosphorylation of Xchk1 (Guo and Dunphy (2000) *Mol Biol Cell* 11: 1535–1546). Xcds1 is phosphoylated in response to double-stranded DNA ends. FIG. 4C shows that the effects of Xatr immunodepletion are specific to effects on phosphorylation of Xchk1. Phosphorylation of Xcds1 in response to DNA ends is unaffected by immunodepletion of Xatr (lanes 2–5).

Figure 4D:
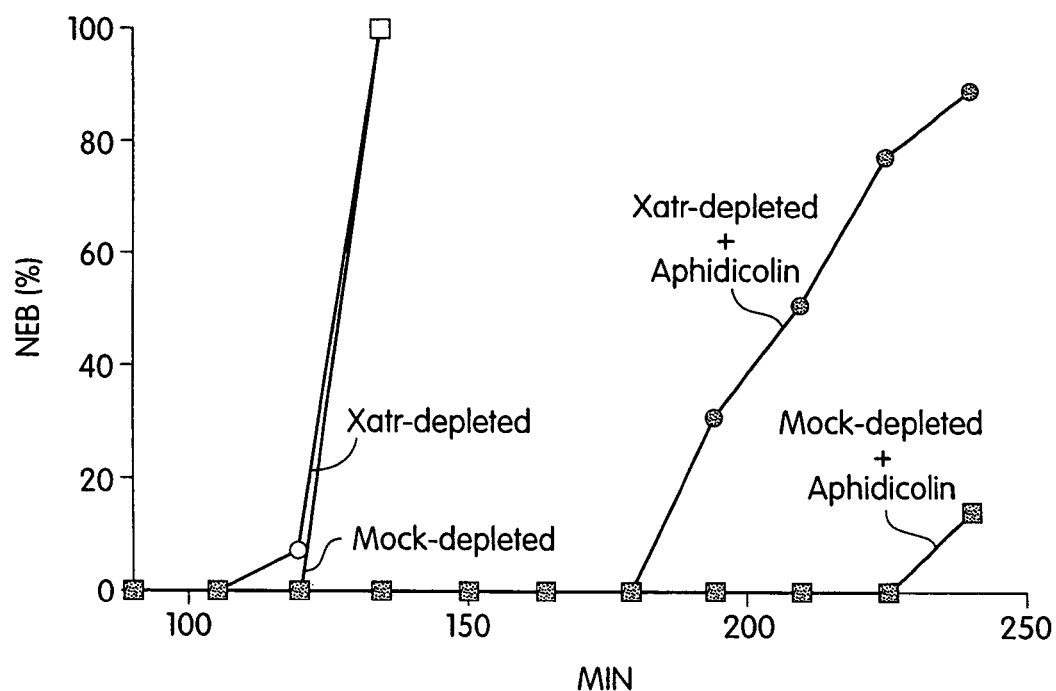
FIG. 4D shows that immunodepletion of Xatr from egg extracts decreases cell cycle delay in response to DNA replication blocks, as induced by treatment with aphidicolin. Cell cycle delay was assessed by measuring the timing of nuclear envelope breakdown (NEB). Open shapes (circle or square) indicate the results of extracts activated with $CaCl_2$ before addition of sperm nuclei but in the absence of aphidicolin. Note that the depletion of Xatr has no effect on cell cycle progression in the absence of DNA damage or a replication block. Closed shapes (circle or square) indicate the results of extracts activated with $CaCl_2$ before the addition of sperm nuclei plus aphidicolin. Cell cycle delay in Xatr depleted extracts treated with aphidicolin is reduced in comparison to mock-depleted (Xatr containing) extracts treated with aphidicolin.

Inhibition of proper phosphorylation of Xchk1 in response to DNA damage in Xatr depleted extracts is suggestive of a crucial role of Xatr dependent phosphorylation of Xchk1 in check-point control. In order to demonstrate that the effect on Xchk1 phosphorylation in Xatr immunodepleted extracts is also associated with changes in check-point control, we examined cell cycle delay in response to an aphidicolin induced DNA replication block in Xatr immunodepleted extracts. FIG. 4D showed that immunodepletion of Xatr from egg extracts decreased cell cycle delay in response to DNA replication blocks, as induced by treatment with aphidicolin. Cell cycle delay was assessed by measuring the timing of nuclear envelope breakdown (NEB). Open shapes (circle or square) indicate the results of extracts activated with CaCl$_2$ before addition of sperm nuclei but in the absence of aphidicolin. Note that the depletion of Xatr has no effect on cell cycle progression in the absence of DNA damage or a replication block. Closed shapes (circle or square) indicate the results of extracts activated with CaCl$_2$ before the addition of sperm nuclei plus aphidicolin. Cell cycle delay in Xatr depleted extracts treated with aphidicolin was reduced in comparison to mock-depleted (Xatr containing) extracts treated with aphidicolin.

METHODS: Immunodepletion of Xatr—M-phase egg extracts were incubated with 20 μg affinity purified anti-Xatr antibodies bound to 10 μL of Affiprep protein A beads at 4° C. for 50 minutes. Following incubation, the preparations were centrifuged to remove the beads and the extracts were treated again to insure removal of Xatr. For mock depletion, egg extracts were treated under the same conditions with a control rabbit IgG antibody (Zymed Laboratories).

Example 6

Xchk1 is a Direct Target of Xatr

Immunodepletion of Xatr prevents the DNA damage induced phosphorylation of Xchk1. Although such an experiment demonstrates that Xatr is necessary for phosphorylation of Xchk1, it does not demonstrate that Xchk1 is a substrate for the Xatr kinase. By analogy to yeast, it has been thought that Xchk1 is downstream of Xatr, but to our knowledge whether a direct interaction between the proteins exists has not been addressed.

Figure 5:
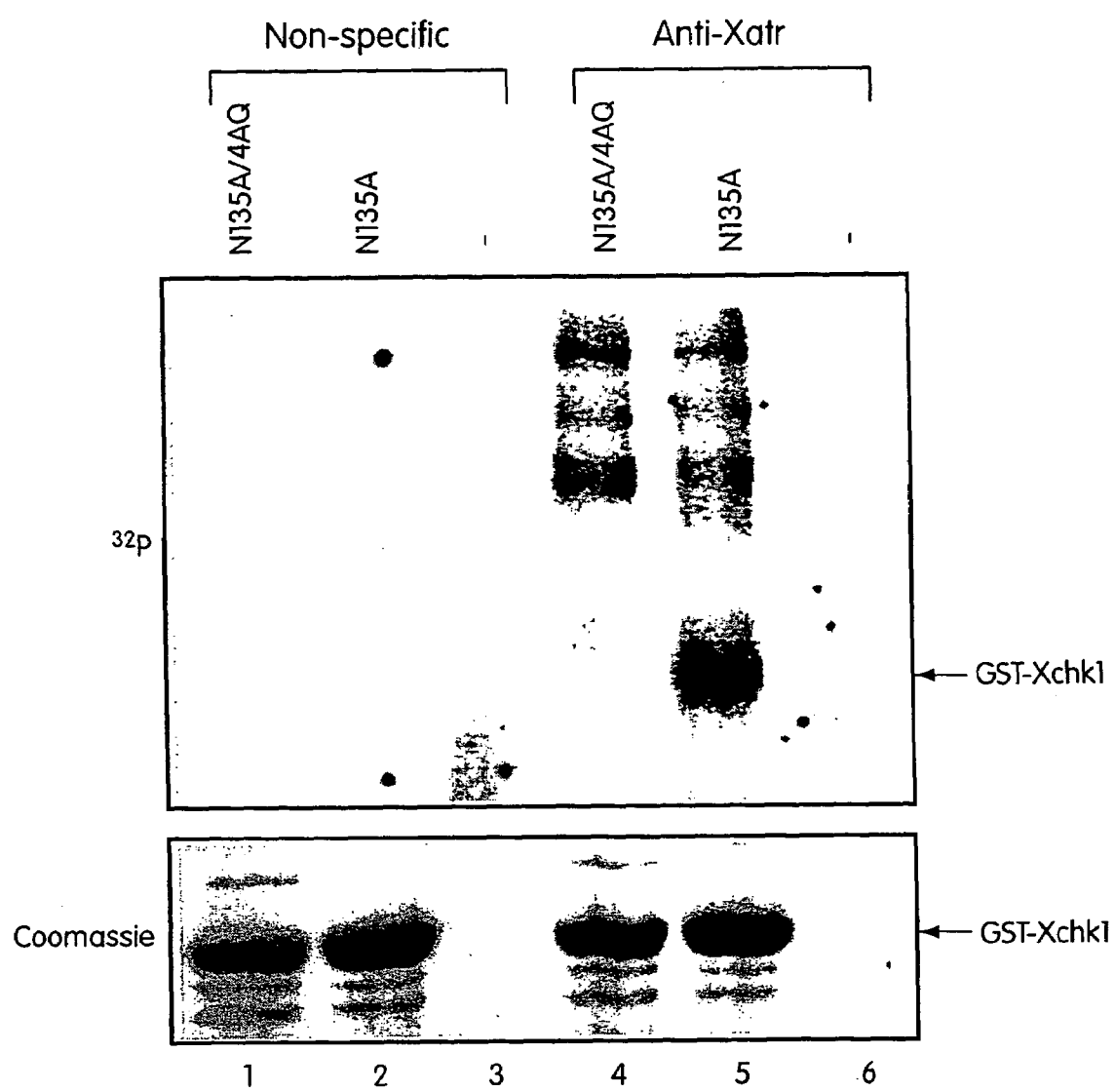
FIG. 5 shows that Xchk1 is a direct target of Xatr in vitro. Immunoprecipitated Xatr was incubated with a kinase inactive Xchk1 (GST-Xchk1-N135A) in the presence of $^{32}P$, and as shown in lane 5, Xatr phosphorylates Xchk1. However, as shown in lane 4, immunoprecipitated Xatr does not phosphorylate a mutated version of Xchk1 where the four likely phosphorylation sites have been changed from a serine or threonine to an alanine (GST-Xchk1-N135A-4AQ).

To address this question, a kinase inactive Xchk1 mutant (GST-Xchk1-N135A) was incubated in vitro with Xatr immunoprecipitated from egg extracts. Since Xchk1 has endogenous kinase activity, the kinase inactive mutant was used to be certain that any phosphorylation observed in vitro was the result of the kinase activity of Xatr. The results summarized in FIG. 5 demonstrate that Xchk1 is a substrate for Xatr—Xatr phosphorylates Xchk1 in vitro (compare lane 5 to lane 6).

Previous analysis of human PIK-kinase family members has indicated that these kinases preferentially phosphorylate their substrates at SQ and TQ motifs (Kim et al. (1999) *Journal of Biological Chemistry* 274: 37538–37543). Consistent with these observations, Xchk1 contains one TQ motif (Thr 314) and three SQ motifs (Ser 344, Ser 356, Ser 365). Accordingly, we constructed a mutant Xchk1 modified not only in the kinase domain (Xchk1-N135A), but also modified at positions 314, 344, 356 and 365 where the threonine or serine residues were mutated to alanine. The results summarized in FIG. 5 demonstrate that the resulting mutant (GST-Xchk1-N135A-4AQ) was not phosphorylated by Xatr (lane 4).

Figure 6A:
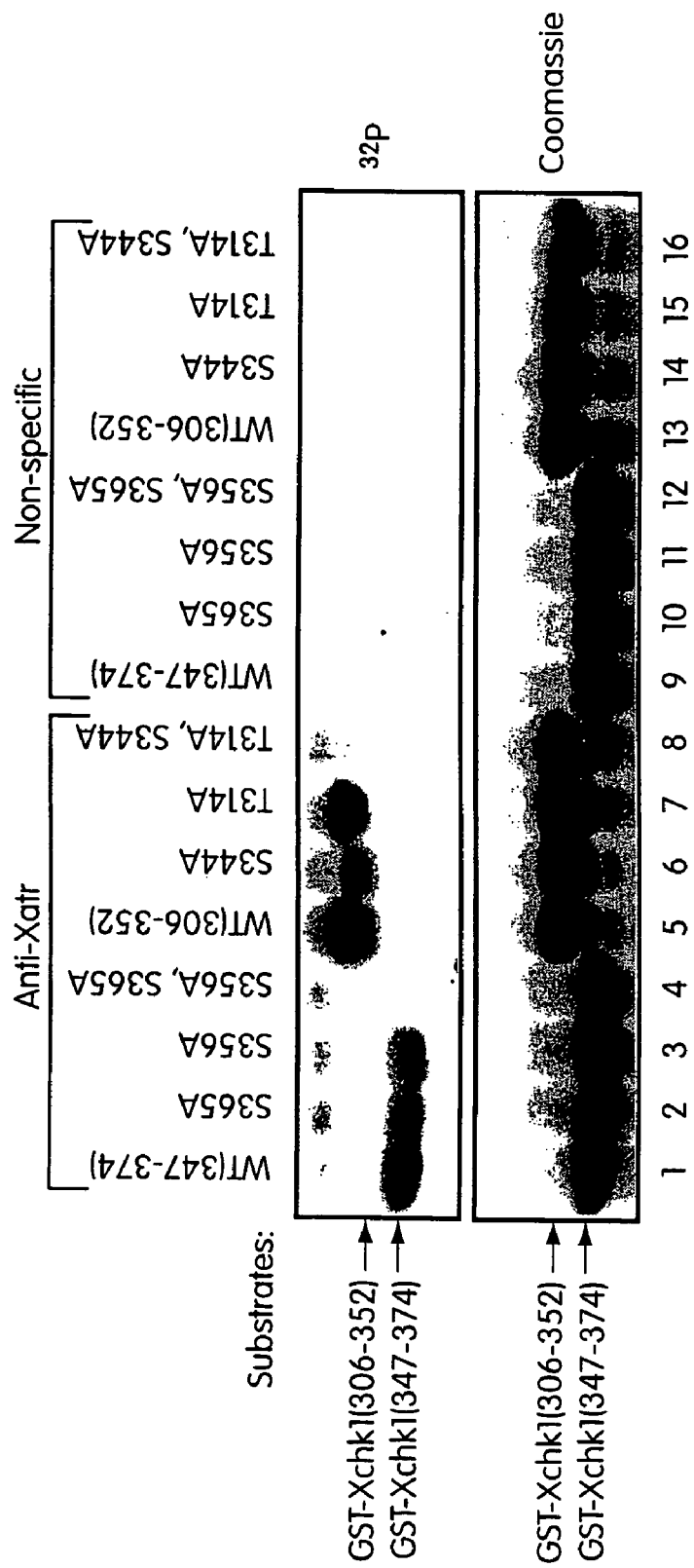
FIG. 6A shows that Xatr can phosphorylate Xchk1 at any one of the TQ or SQ sites. A series of wildtype and mutant Xchk1 peptides were generated. Xchk1(306–352) is a wild type peptide fragment containing a TQ motif at position 314 and an SQ motif at position 344. GST-Xchk1 (347–374) is a wildtype peptide fragment containing an SQ motif at position 356 and an SQ motif at position 365. Mutant fragments were also generated including S365A, S356A, S365A+S356A, S344A, T314A and S344A+T314A. Xatr phosphorylates both of the wildtype peptide fragments (lanes 1 and 5—top panel). Additionally, Xatr phosphorylates Xchk1 when a single SQ or TQ site is mutated although the level of phosphorylation is significantly reduced in comparison to that observed with wildtype peptide (lanes 2, 3, 6 and 7). However, mutation of both sites within each peptide (S365A+S356A or S344A+T314A) abolished phosphorylation by Xatr (lanes 4 and 8).

To better characterize the phosphorylation of Xchk1 by Xatr, we generated a series of Xchk1 peptides containing one or more mutations at the various SQ or TQ motifs described in detail above. GST-Xchk1 (306–352) is a wild type peptide fragment containing a TQ motif at position 314 and an SQ motif at position 344. GST-Xchk1 (347–374) is a wildtype peptide fragment containing an SQ motif at position 356 and an SQ motif at position 365. In addition to the two wildtype peptide fragments, we generated mutant fragments: S365A, S356A, S365A+S356A, S344A, T314A and S344A+T314A. FIG. 6A summarizes the results of experiments which examined the ability of Xatr to phosphorylate each of these Xchk1 peptides in vitro. Xatr phosphorylated both of the wildtype peptide fragments (lanes 1 and 5—top panel). Additionally, Xatr phosphorylated Xchk1 when a single SQ or TQ site is mutated although the level of phosphorylation is significantly reduced in comparison to that observed with wildtype peptide (lanes 2, 3, 6 and 7). However, mutation of both sites within each peptide (S365A+S356A or S344A+T314A) abolished phosphorylation by Xatr (lanes 4 and 8).

METHODS: In vitro phosphorylation of bacterially expressed GST-Xchk1 by Xatr—Xatr was immunoprecipitated from DNA cellulose containing egg extracts and incubated with either bacterially expressed GST-Xchk1-N135A, bacterially expressed GST-Xchk1-N135-4AQ, or no substrate. Incubation was carried out in the presence of $^{32}$P-ATP. Proteins were subjected to SDS-PAGE. Total protein was visualized by Coomassie blue staining, and Xchk1 phosphorylation was detected by autoradiography.

Preparation of recombinant Xchk1 proteins (note the methods described here refer to mutant proteins used in this and in subsequent examples)—Mutant forms of Xchk1 were generated from a pBS-XChk1 plasmid (Kumagai et al. (1998) *Journal of Cell Biology* 142: 1559–1569) by one or more rounds of mutagenesis using the QuikChange kit (Statagene) plus oligonucleotides. Where needed $^{35}$S-labeled wildtype or mutant Xchk1 proteins were generated with the TNT-in vitro transcription/translation kit (Promega). To generate GST fusions, various wild type and mutant Xchk1 proteins were subcloned into pGEX-2T (Amersham Pharmacia Biotech), and the GST fusion proteins were expressed and isolated from *E.coli* using standard protocols (Frangioni and Neel (1993) *Anal Biochem* 210: 179–187).

Example 7

Human ATR Phosphorylates Xchk1

Although the proteins involved in sensing and responding to various forms of DNA damage appear to be conserved across phyla (e.g., ATR, ATM, Chk1, Cds1, etc homologs), it has previously been unclear if the specific mechanisms employed by these proteins to sense and respond to DNA damage are conserved. In fact, although we had previously demonstrated that in *Xenopus* Cds1 and Chk1 respond specifically to different types of DNA damage (Guo and Dunphy (2000) *Mol Biol Cell* 11: 1535–1546; Kumagai et al. (1998) *Journal of Cell Biology* 142: 1559–1569), others have reported that in both humans and mice, the responses to DNA damage may be less restricted (Sanchez et al. (1997) *Science* 277: 1497–1501; Matsuoka et al. (1998) *Science* 282: 1893–1897; Blasina et al. (1999) *Current Biology* 9: 1–10; Brown et al. (1999) *PNAS* 96: 3745–3750; Tominaga et al. (1999) *Journal of Biological Chemistry* 274: 31463–31467; Hirao et al. (2000) *Science* 287: 1824–1827; Takai et al. (2000) *Genes & Development* 14: 1439–1447; Liu et al. (2000) *Genes & Development* 14: 1448–1459). Accordingly, to better assess the extent to which ATR-Chk1 signaling is conserved across phyla, we examined whether human ATR could phosphorylate Xchk1 in vitro.

Figure 6B:
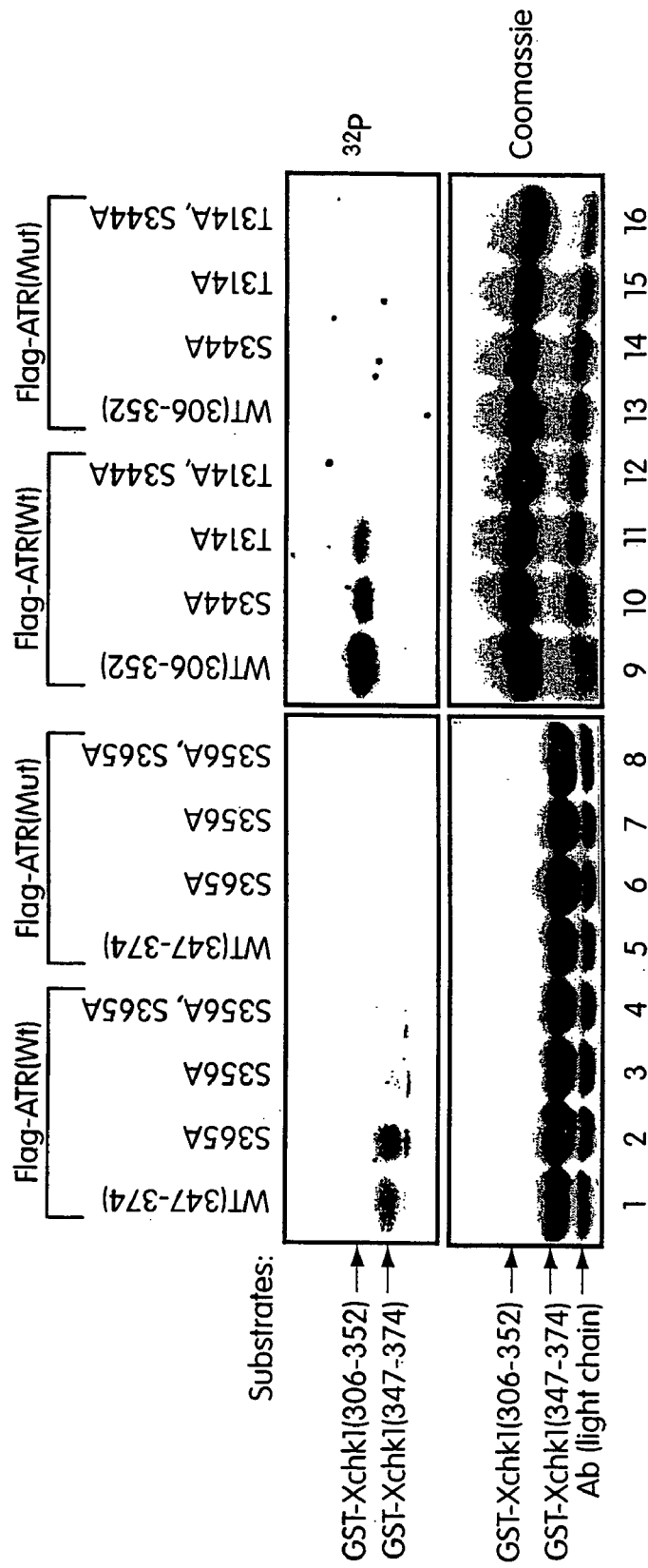
FIG. 6B shows that human ATR phosphorylates Xchk1 in vitro. Wildtype or a kinase-inactive (Mut) human Flag-tagged ATR was isolated from 293T cells. Wildtype ATR phosphorylates the wildtype XChk1 peptides Xchk1 (306–352) and Xchk1(347–374) (lanes 1 and 9). Human ATR phosphorylates each of the single point mutant Chk1 substrates (S365A, S356A, S344A and T314A—as shown in lanes 2, 3, 10, 11), however the level of phosphorylation is reduced in comparison to that observed for the wildtype Xchk1 peptides. However, human ATR does not phosphorylate the double mutant XChk1 substrates (S365A+S356A or S344A+T314A—as shown in lanes 4 and 12). As a control, phosphorylation of the Xchk1 substrates by a kinase-inactive human ATR was measured. As shown in lanes 5–8 and 13–16, the kinase inactive mutant form of human ATR failed to phosphorylate any of the Xchk1 substrates.

FIG. 6B summarizes experiments which demonstrated that human ATR phosphorylates Xchk1 in vitro. Wildtype or a kinase-inactive (Mut) human Flag-tagged ATR was isolated from 293T cells using standard methods and as described (Canman et al. (1998) *Science* 281: 1677–1679). Wildtype human ATR phosphorylated the wildtype XChk1 peptides Xchk1 (306–352) and Xchk1(347–374) (see FIG.

6B, lanes 1 and 9). Additionally, human ATR phosphorylated each of the single point mutant Chk1 substrates (S365A, S356A, S344A and T314A—as shown in lanes 2, 3, 10, 11). We note that consistent with the results seen with Xatr, the level of phosphorylation of the single mutant forms of Xchk1 by human ATR is also reduced. However, as was observed with Xatr, human ATR does not phosphorylate the double mutant XChk1 substrates (S365A+S356A or S344A+T314A—as shown in lanes 4 and 12). We note that the kinase inactive mutant form of human ATR failed to phosphorylate any of the Xchk1 substrates (lanes 5–8 and 13–16). These results demonstrate for the first time that the direct phosphorylation of Chk1 by ATR is a well conserved mechanism.

Example 8

Phosphorylation of SQ/TQ Motifs of Xchk1 In Vivo

Figure 7A:
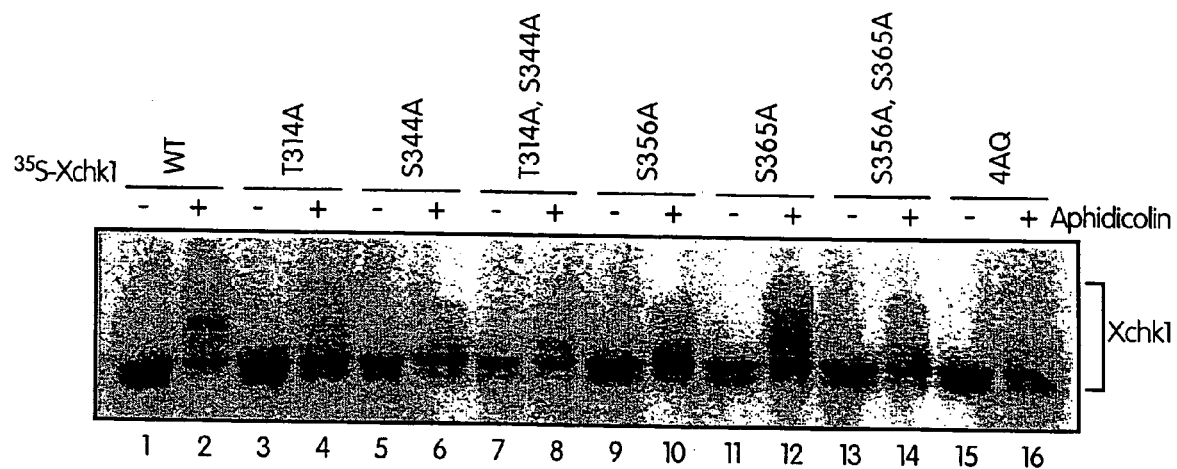
FIG. 7A shows that phosphorylation of Xchk1 on SQ/TQ motifs in response to DNA damage occurs in vivo. $^{35}$S-labeled wildtype or mutant Xchk1 (T314A, S344A, T314A+S344A, S356A, S365A, S356A+S365A, 4AQ) protein was incubated with egg extracts in the presence or absence of aphidicolin. $^{35}$S labeled proteins were isolated and analyzed by gel electrophoresis for a phosphorylation-dependent shift in mobility. The wildtype Xchk1 protein was phosphorylated in response to aphidicolin treatment (compare lane 1 to lane 2). Additionally, each of the single mutants are phosphorylated—although the degree of phosphorylation varies and in some cases was reduced in comparison to the wild-type protein (lanes 4, 6, 10, 12). In the case of the two double mutants, phosphorylation was substantially reduced (lanes 8 and 14). Finally we not that in the quadruple mutant, 4AQ, aphidicolin dependent phosphorylation of Xchk1 was eliminated (lane 16).

The foregoing experiments demonstrated that Xchk1 can be phosphorylated on SQ/TQ motifs. We performed additional analysis to confirm that phospohrylation on these motifs does in fact occur in vivo, and that this phosphorylation specifically occurs in response to DNA damage. To address this question, we first measured phosphorylation of Xchk1 in egg extracts undergoing a checkpoint delay in response to a block to DNA replication. FIG. 7A summarizes results which indicated that Xchk1 is in fact phosphorylated in vivo in response to a DNA replication block induced by administration of aphidicolin. Briefly, $^{35}$S-labeled wildtype or mutant Xchk1 (T314A, S344A, T314A+S344A, S356A, S365A, S356A+S365A, 4AQ) protein was incubated with egg extracts in the presence or absence of aphidicolin. $^{35}$S labeled proteins were isolated and analyzed by gel electrophoresis for a phosphorylation-dependent shift in mobility. As shown in FIG. 7A, the wildtype Xchk1 protein is phosphorylated in response to aphidicolin treatment (compare lane 1 to lane 2). Additionally, each of the single mutants are phosphorylated—although the degree of phosphorylation varies and in some cases is reduced in comparison to the wildtype protein (lanes 4, 6, 10, 12). In the case of the two double mutants, phosphorylation was substantially reduced (lanes 8 and 14). Finally we note that in the quadruple mutant, 4AQ, aphidicolin dependent phosphorylation of Xchk1 was eliminated (lane 16).

Figure 7B:
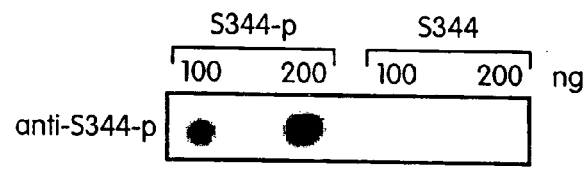
FIG. 7B shows the characterization of anti-S344-p antibodies. Antibodies that recognize phosphorylated Ser 344 were generated, and the ability of these antibodies to recognize a peptide phosphorylated on Ser344 was assessed. Increasing concentrations of phosphorylated (S344-p) or unphosphorylated (S344) peptide were blotted on nitrocellulose. The antibody specifically detects the phosphorylated peptide.

We note that of the single point mutants analyzed, mutation at position 344 (S344A) appeared to have the largest effect on Xchk1 phosphorylation. In order to further analyze phosphorylation specifically at this position, we generated antibodies designed to specifically recognize phosphorylated serines at position 344. Antibodies that recognize phosphorylated Ser 344 were generated, as described below, and the ability of these antibodies to recognize a peptide phosphorylated on Ser344 was assessed. As shown in FIG. 7B, these anti-phospho (S344) antibodies specifically detect peptides phosphorylated at a serine at position 344. Briefly, increasing concentrations of phosphorylated (S344-p) or unphosphorylated (S344) peptide were blotted on nitrocellulose, and the antibody specifically detects the phosphorylated peptide.

Figure 7C:
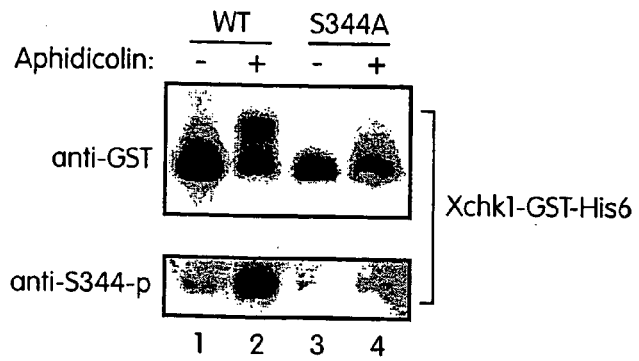
FIG. 7C shows that wildtype Xchk1 was phosphorylated on position 344 in response to an aphidicolin induced DNA replication block (lanes 1 and 2). In contrast, an Xchk1 protein carrying an S to A mutation at position 344 was not phosphorylated, either in the presence or absence of aphidicolin (lanes 3 and 4).

Using the S344-p antibodies, we examined in more detail the phosphorylation of Xchk1 expressed in egg extracts. The results of these experiments are shown in FIG. 7C and demonstrated that wildtype Xchk1, but not Xchk1 bearing a mutation at position 344, was phosphorylated on serine 344 in response to an aphidicolin induced DNA replication block. Briefly, we made recombinant, baculovirus expressed, double-tagged, wildtype and mutant Xchk1 constructs (Xchk1-WT-GST-His6 and Xchk1-S244A-GST-His6). The wildtype (Xchk1-WT-GST-His6) or mutant (Xchk1-S244A-GST-His6) proteins were incubated in egg extracts in the presence or absence of aphidicolin for 90 minutes. Following the incubation, the recombinant proteins were reisolated with glutathione agarose and detected by immunoblot with anti-GST antibodies and anti-S344-p antibodies. As shown in FIG. 7C, the wildtype Xchk1 protein was phosphorylated at position 344 in the presence of aphidicolin. In contrast, the mutant protein was not phosphorylated at position 344 in response to aphidicolin.

METHODS: 200 µL of interphase extract containing 100 µg/mL of cycloheximide and 3 µM tautomycin was incubated with 2 µg of Xchk1-WT-GST-His6 or Xchk1-S344A-GST-His6 in the presence or absence of 100 µg/mL of aphidicolin and sperm nuclei. Following 90 minute incubation, the preparation was diluted in 400 µL of dilution buffer (10 mM HEPES at pH 7.5, 150 mM NaCl, 20 mM β-glycerolphosphate, 2.5 mM EGTA, and 0.1% CHAPS). Recombinant Xchk1 proteins were isolated with glutathione agarose, washed, eluted, subjected to SDS-PAGE, and immunoblotted with either anti-GST antibodies (Santa Cruz Biotechnology) or anti-S344-p antibodies. Anti-S344-p antibodies were raised against a peptide which is phosphorylated on Ser344 (CGKGISFS(p)QPAAPDNM, SEQ ID NO: 12).

Example 9

Phosphorylation of Chk1 at SQ/TQ Motifs is Required for the DNA Replication Checkpoint The foregoing experiments demonstrated that Xchk1 is phosphorylated at SQ/TQ motifs in vivo in response to DNA damage such as an aphidicolin induced DNA replication block. However, these experiments do not address the physiological significance of this damage induced phosphorylation, or the impact of phosphorylation on DNA damage dependent cell cycle delay.

Figure 8A:
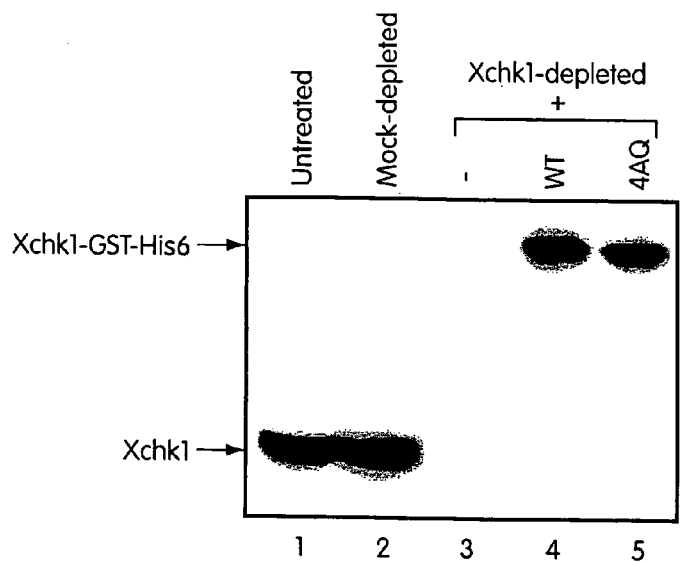
FIG. 8A shows that Xchk1 can be immunodepleted from egg extracts using anti-Xchk1 antibodies (compare the bottom band in lanes 1 and 2 with lanes 3–5).

To address these questions, we wanted to examine aphidicolin induced cell cycle delay in the presence or absence of wildtype Xchk1. In order to assess the effects of mutant forms of Xchk1, egg extracts depleted of endogenous Xchk1 were prepared. Using such immunodepleted egg extracts, the effects of various mutant forms of Xchk1 protein can be specifically assessed without compounding effects due to the presence of endogenous wildtype protein in the egg extracts. FIG. 8A shows that endogenous Xchk1 can be successfully immunodepleted from egg extracts using anti-Xchk1 antibodies (compare the bottom band in lanes 1 and 2 with lanes 3–5). FIG. 8A also shows that recombinantly produced wildtype (Xchk1-GST-His6) or 4AQ mutant (Xchk1-4AQ-GST-His6) protein can be added back to the immunodepleted extracts (compare the top band in lanes 4 and 5 with lanes 1–3).

Figure 8B:
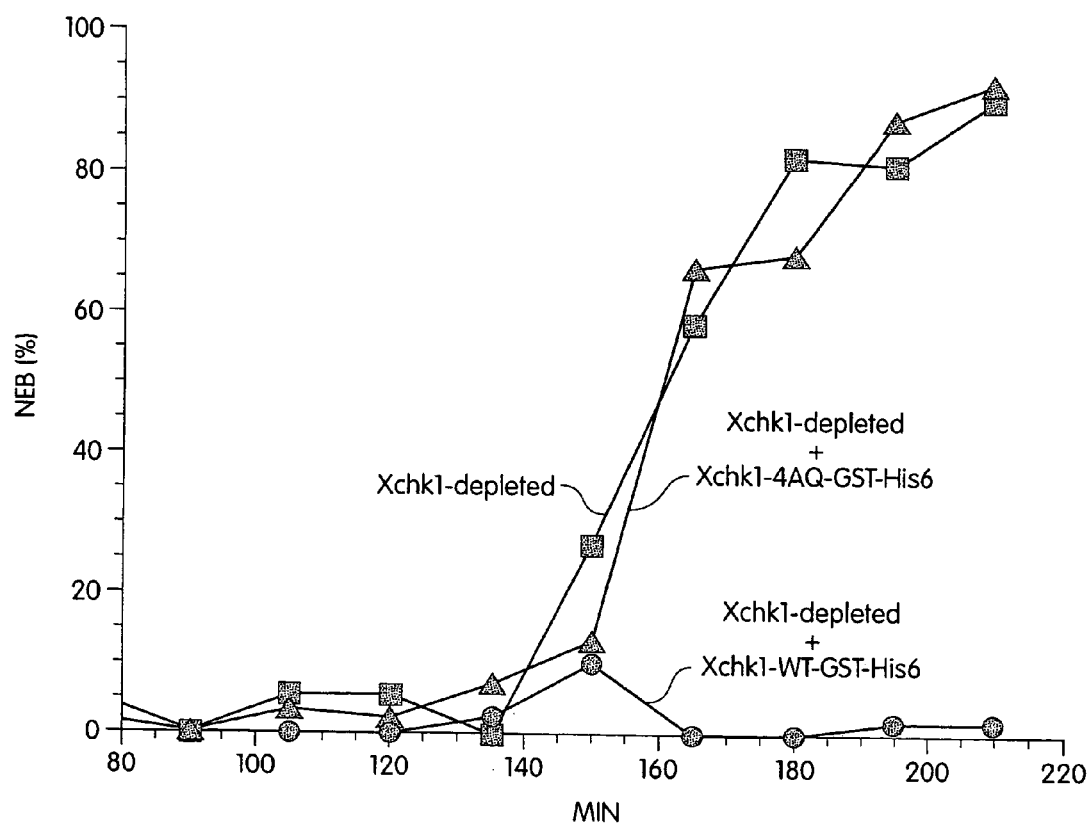
FIG. 8B demonstrates that aphidicolin induced cell cycle delay requires SQ/TQ cites in Xchk1. Egg extracts were treated with aphidicolin, and the timing of mitosis was measured. Xchk1 immunodepleted, aphidicolin treated extracts inappropriately enter the cell cycle (i.e., they have a compromised DNA damage induced cell cycle delay). Appropriate cell cycle delay is rescued when wildtype Xchk1 (Xchk1-WT-GST-His6) is added back to immunodepleted extracts. However, appropriate cell cycle delay is not restored when a non-phosphorylatable mutant form of Xchk1 (Xchk1-4AQ-GST-His6) is added back to immunodepleted extracts.

This system allowed us to address the effects of phosphorylation of Xchk1 on cell cycle delay in response to aphidicolin. FIG. 8B summarizes the results which demonstrated that aphidicolin induced cell cycle delay requires SQ/TQ cites in Xchk1. Briefly, egg extracts were treated with aphidicolin, and the timing of mitosis was measured. As previously observed, in the absence of Xchk1 (Xchk1 immunodepleted extracts) aphidicolin treated extracts inappropriately enter the cell cycle (i.e., they have a compromised DNA damage induced cell cycle delay) (Kumagai et al. (1998) *Journal of Cell Biology* 142: 1559–1569) As expected based on previous reports, appropriate cell cycle delay was rescued when wildtype Xchk1 (Xchk1-WT-GST-His6) was added back to immunodepleted extracts (Kumagai et al. (1998) *Journal of Cell Biology* 142: 1559–1569). However, we observed that appropriate cell cycle delay was not restored when a non-phosphorylatable mutant form of Xchk1 (Xchk1-4AQ-GST-His6) was added back to immunodepleted extracts. These results demonstrated that the phosphorylation of SQ/TQ motifs on Chk1 is important, in vivo, for proper cell cycle delay in response to DNA replication blocks and DNA damage.

ADDITIONAL REFERENCES

U.S. Pat. No. 6,307,015 WO02/33115
WO01/83703 WO97/09433
Scully et al. (2000) *Oncogene* 19: 6176–6183
Cimprich et al. (1996) *PNAS* 93: 2850–2855.
Zhou and Elledge (2000) *Nature* 408: 433–439.
Walworth (2000) *Current Opinion in Cell Biology* 12: 697–704.
Durocher and Jackson (2001) *Current Opinion in Cell Biology* 13: 225–231.
Hoekstra (1997) *Current Opinion in Genetics and Development* 7: 170–175.
Shiloh (2001) *Current Opinion in Genetics and Development* 11: 71–77.
Canman (2001) *Current Biology* 11: R121–R124.
Canman (1998) *Science* 281: 1677–1679.
Brown and Baltimore (2000) *Genes and Development* 14: 397–402.
Banin et al. (1998) *Science* 281: 1674–1677.
Brown et al. (1999) *PNAS* 96: 3745–3750.
Chan et al. (1999) *Nature* 401: 616–620.
Chaturvedi et al. (1999) *Oncogene* 18: 4047–4054.
Cliby et al. (1998) *EMBO J* 17: 159–169.
Cortez et al. (1999) *Science* 286: 1162–1166.
de Klein et al. (2000) *Current Biology* 10: 479–482.
Gatei et al (2000) Nature Genetics All publications, patents and patent applications are herein incorporated by reference in their entirety to the same extent as if each individual publication, patent or patent application was specifically and individually indicated to be incorporated by reference in its entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid encoding a polypeptide comprising an amino acid sequence at least 90% identical to SEQ ID NO: 2, wherein said polypeptide (i) can phosphorylate a Chk1 protein, (ii) can bind to single-stranded DNA, (iii) can bind to double-stranded DNA, (iv) can induce cell cycle delay in response to UV damaged DNA, and/or (v) can induce cell cycle delay in response to a DNA replication block.

2. The nucleic acid of claim 1, wherein said nucleic acid encodes a polypeptide comprising an amino acid sequence at least 95% identical to SEQ ID NO: 2.

3. The nucleic acid of claim 1, wherein said nucleic acid encodes a *Xenopus* polypeptide.

4. The nucleic acid of claim 1, wherein said nucleic acid encodes a polypeptide comprising an amino acid sequence at least 90% identical to residues 2208–2654 of SEQ ID NO: 2 or residues 2351–2654 of SEQ ID NO: 2.

5. An isolated nucleic acid encoding a polypeptide comprising an amino acid sequence identical to SEQ ID NO: 2.

6. The nucleic acid of claim 1, wherein said nucleic acid encodes a polypeptide comprising an amino acid sequence identical to residues 2208–2654 of SEQ ID NO: 2 or residues 2351–2654 of SEQ ID NO: 2.

7. The nucleic acid of claim 1 or 5, further comprising a transcriptional regulatory sequence operably linked to said nucleic acid sequence.

8. An expression vector, capable of replicating in at least one of a prokaryotic cell and eukaryotic cell, comprising the nucleic acid of claim 7.

9. A host cell transfected with the expression vector of claim 8 and expressing said polypeptide.

10. A method of producing a recombinant polypeptide having an amino acid sequence at least 90% identical to SEQ ID NO:2 comprising culturing the cell of claim 9 in a cell culture to express said polypeptide and isolating said polypeptide from said cell culture.

11. The nucleic acid of claim 1, which polypeptide is a fusion protein.

* * * * *